United States Patent
Woltering et al.

(10) Patent No.: US 6,180,082 B1
(45) Date of Patent: Jan. 30, 2001

(54) METHOD TO ENHANCE TISSUE ACCUMULATION OF RADIOLABELED COMPOUNDS

(75) Inventors: Eugene A. Woltering, Kenner; Gregory D. Espenan, Metairie, both of LA (US)

(73) Assignee: Board of Supervisors of Louisiana State University and Agricultural and Mechanical College, Baton Rouge, LA (US)

(*) Notice: Under 35 U.S.C. 154(b), the term of this patent shall be extended for 0 days.

(21) Appl. No.: 09/198,562

(22) Filed: Nov. 23, 1998

Related U.S. Application Data

(60) Provisional application No. 60/160,087, filed on Nov. 24, 1997.

(51) Int. Cl.[7] .......................... A61K 51/00; A61M 36/14

(52) U.S. Cl. ...................... 424/1.69; 424/1.65; 424/1.11; 530/300; 530/311; 530/317

(58) Field of Search .................................. 424/1.11, 1.65, 424/1.69, 9.1; 530/300, 311, 317, 324–330

(56) References Cited

U.S. PATENT DOCUMENTS

| | | | |
|---|---|---|---|
| 5,590,656 | 1/1997 | O'Dorisio et al. | 128/654 |
| 5,597,894 | 1/1997 | Coy et al. | 530/311 |

FOREIGN PATENT DOCUMENTS

| | | |
|---|---|---|
| 9101144 | 2/1991 | (WO). |

OTHER PUBLICATIONS

R. B. Hochberg, "Iodine–125–Labeled Estradiol: A Gamma–Emitting Analog of Estradiol That Binds to the Estrogen Receptor," Science, vol. 205, pp. 1138–1140, (1979).

S.W.J. Lamberts et al., "Somatostatin–Receptor Imaging in the Localization of Endocrine Tumors," The New England Journal of Medicine, vol. 323, pp. 1246–1249 (1990).

E.P. Krenning et al., "Somatostatin Receptor Scintigraphy with Indium–111–DTPA–D–Phe–1–Octreotide in Man: Metabolism, Dosimetry and Comparison with Iodine–123–Tyr–3–Octreotide," The Journal of Nuclear Medicine, vol. 33, pp. 652–658 (1992).

E.P. Krenning et al., "Localisation of Endocrine–Related Tumours with Radioiodinated Analogue of Somatostatin," The Lancet, vol. 1989, No. 1, pp. 242–244 (1989).

J.A. Carrasquillo et al., "Indium–111 T101 Monoclonal Antibody is Superior to Iodine–131 T101 in Imaging of Cutaneous T–Cell Lymphoma," The Journal of Nuclear Medicine, vol. 28, pp. 281–287 (1987).

R.M. Kessler et al., "High Affinity Dopamine D2 Receptor Radioligands. 1. Regional Rat Brain Distribution of Iodinated Benzamides," The Journal of Nuclear Medicine, vol. 32, pp. 1593–1600 (1991).

H. Zhu et al., "Potential and Limitations of Radioimmunodetection and Radioimmunotherapy with Monoclonal Antibodies," The Journal of Nuclear Medicine, vol. 38, No. 5, pp. 731–741 (1997).

W.V. Welshons et al., "Nuclear Localization of Unoccupied Oestrogen Receptors," Nature, vol. 307, pp. 747–749 (1984).

A. Kurtaran, et al., "Vasoactive Intestinal Peptide and Somatostatin Receptor Scintigraphy for Differential Diagnosis of Hepatic Carcinoid Metastasis," The Journal of Nuclear Medicine, vol. 38, pp. 880–881 (1997).

G.A. Wiseman et al., "Therapy of Neuroendocrine Tumors with Radiolabeled MIBG and Somatostatin Analogues," Seminars in Nuclear Medicine, vol. XXV, No. 3, pp. 272–278 (1995).

R.K. Rippley et al., "Effects of Cellular Pharmacology on Drug Distribution in Tissues," Biophysical Journal, vol. 69, pp. 825–839 (1995).

H.P. Kalofonos et al., "Antibody Guided Diagnosis and Therapy of Brain Gliomas using Radiolabeled Monoclonal Antibodies Against Epidermal Growth Factor Receptor and Placental Alkaline Phosphatase," The Journal of Nuclear Medicine, vol. 30, pp. 1636–1645 (1989).

I. Virgolini et al., "Vasoactive Intestinal Peptide–Receptor Imaging for the Localization of Intestinal Adenocarcinomas and Endocrine Tumors," The New England Journal of Medicine, vol. 331, pp. 1116–1121 (1994).

E.A. Woltering et al., "Somatostatin Analogs: Angiogenesis Inhibitors with Novel Mechanisms of Action," Investigational New Drugs, vol. 15, pp. 77–86 (1997).

E.A. Woltering et al., "The Role of Radiolabeled Somatostatin Analogs in the Management of Cancer Patients," Principles & Practice of Oncology, vol. 9, pp. 1–15 (1995).

I. Virgolini et al., "'Mauritius': Biodistribution, Safety and Tumor Dose in Patients Evaluated for Somatostatin Receptor–Mediated Radiotherapy," Paper Submitted to Journal of Nuclear Medicine (1997).

(List continued on next page.)

*Primary Examiner*—Damcron Jones
(74) *Attorney, Agent, or Firm*—Bonnie J. Davis; John H. Runnels

(57) ABSTRACT

Administration of a radioisotopic compound by infusion over a period of time greater than two hours, preferably greater than twelve hours, greatly increases the maximum radioactivity that accumulates in the target cell. The efficacy of the administration of the radiolabeled compound can be increased about five times higher than prior bolus injection or short infusion methods. This method enhances the tumor to background ratio by increasing the actual radioligand accumulated inside the target cells. This technique works for any radiolabeled compound whose cellular uptake is limited by a cellular process of either binding to a cellular receptor or to a transport protein. Once the radiolabeled compound is bound and internalized, the ability of an unlabeled compound to compete with the radioligand is markedly decreased. The primary factor governing residence time after internalization is the physical half-life of the radioisotope, not biologic half-life.

57 Claims, 28 Drawing Sheets

OTHER PUBLICATIONS

L.J. Hofland et al., "Internalization of the Radioiodinated Somatostatin Analog [$^{125}$I-Tyr$^3$] Octreotide by Mouse and Human Pituitary Tumor Cells: Increase by Unlabeled Octreotide," Endocrinology, vol. 136, pp. 3698–3706 (1995).

E.P. Krenning et al., "Radiotherapy with a radiolabeled somatostatin analogue, [$^{111}$In–DTPA–D–Phe1]–octreotide. A Case History," Annals of the New York Academy of Sciences, vol. 733, pp. 496–506 (1996).

M. Fjalling et al., "Systemic radionuclide therapy using indium–111–DTPA–D–Phe–1–octreotide in midgut carcinoid syndrome," Journal of Nuclear Medicine, vol. 37, pp. 1519–1521 (1996).

E.P. Krenning et al., "Somatostatin Receptor Scintigraphy with [$^{111}$In–DTPA–D–Phe$^1$]– and [$^{123}$I–Tyr$^3$]–octreotide: the Rotterdam Experience with More than 1000 Patients," European Journal of Nuclear Medicine, vol. 20, pp. 716–731 (1993).

P.M. Laduron, "From Receptor Internalization to Nuclear Translocation—New Targets for Long–Term Pharmacology," Biochemical Pharmacology, vol. 47, pp. 3–13 (1994).

J.C. Watson et al., "Breast Cancer Increases Initiation of Angiogenesis Without Accelerating Neovessel Growth Rate," Surgery, vol. 122, pp. 508–514 (1997).

J.C. Watson et al., "SST–2 Gene Expression Appears During Human Angiogenesis," Regulatory Peptides, vol. 64, p. 206 (Abstract) (1996).

G. Morel, "Internalization and Nuclear Localization of Peptide Hormones," Biochemical Pharmacology, vol. 47(1), pp. 63–76 (1994).

D. Nouel et al., "Differential Internalization of Somatostatin in COS–7 Cells Transfected with SST$_1$ and SST$_2$ Receptor Subtypes: A Confocal Microscopic Study Using Novel Fluorescent Somatostatin Derivatives," Endocrinology, vol. 138, pp. 296–306 (1997).

L.H. Wang et al., "Ligand Binding, Internalization, Degradation and Regulation by Guanine Nucleotides of Bombesin Receptor Subtypes: A Comparative Study," Biochimica et Biophysica Acta, vol. 1175, pp. 232–242 (1993).

O.W. Press et al., "Comparative Metabolism and Retention of Iodine–125, Yttrium–90, and Indium–111 Radioimmunoconjugates by Cancer Cells," Cancer Research, vol. 56, pp. 2123–2129 (1996).

S.E. Strand et al., "Pharmacokinetic Modeling," Medical Physics, vol. 20(2), Pt. 2, pp. 515–527 (1993).

D.J. Sutherland et al., "Hormones and Cancer," The Basic Science of Oncology, 2d Ed. (I.F. Tannock and R.P. Hill, eds.), Chapter 13, pp. 207–231 (1992).

H. Kolan et al., "Sandostatin® Labeled with $^{99m}$Tc: In Vitro Stability, In Vivo Validity and Comparison with $^{111}$In–DTPA–Octreotide," Peptide Research, vol. 9, No. 3, pp. 144–150 (1996).

M.S. O'Reilly, "Angiostatin: An Endogenous Inhibitor of Angiogenesis and of Tumor Growth," in Regulation of Angiogenesis, ed. by I.D. Goldberg & E.M. Rosen, pp. 273–294 (1997).

M.L. Thakur et al., "Radiolabeled Somatostatin Analogs in Prostate Cancer," Nuclear Medicine & Biology, vol. 24, pp. 105–113 (1997).

M. de Jong et al., "Yttrium–90 and Indium–111 Labelling, Receptor Binding and Biodistribution of [DOTA$^0$, D–Phe$^1$, Tyr$^3$]octreotide, a Promising Somatostatin Analogue for Radionuclide Therapy," European Journal of Nuclear Medicine, vol. 24, pp. 368–371 (1997).

W.A.P. Breeman et al., "A New Radiolabelled Somatostatin Analogue [$^{111}$In–DTPA–D–Phe$^1$]RC–160: Preparation, Biological Activity, Receptor Scintigraphy in Rats and Comparison with [$^{111}$In–DTPA–D–Phen$^1$]octreotide," European Journal of Nuclear Medicine, vol. 21, No. 4, pp. 328–335 (1994).

G. Hildebrandt et al., "Results of Continuous Long Term Intravenous Application of Octreotide via an Implantable Pump System in Acromegaly Resistent to Operative and X–ray Therapy," Acta Neurochirurgica, vol. 117, pp. 160–165 (1992).

C.S. Dence et al., "Carbon–11–Labeled Estrogens as Potential Imaging Agents for Breast Tumors," Nuclear Medicine & Biology, vol. 23, pp. 491–496 (1996).

J.C. Watson et al., "Up–Regulation of Somatostatin Receptor Subtype 2 (SST–2) mRNA Occurs During the Transformation of Human Endothelium to the Angiogenic Phenotype," Paper Presented at the 12th International Symposium on Regulatory Peptides, Copenhagen, Denmark, Sep. 1996.

P.C. Patel et al., "Postreceptor Signal Transduction Mechanisms Involved in Octreotide–Induced Inhibition of Angiogenesis," Surgery, vol. 116, pp. 1148–1152 (1994).

R. Barrie et al., "Inhibition of Angiogenesis by Somatostatin and Somatostatin–like Compounds Is Structurally Dependent," Journal of Surgical Research, vol. 55, pp. 446–450 (1993).

J.C. Reubi et al., "High Density of Somatostatin Receptors in Veins Surrounding Human Cancer Tissue: Role in Tumor–Host Interaction?," International Journal of Cancer, vol. 56, pp. 681–688 (1994).

P.M. Vanhagen et al., "Somatostatin Receptor Imaging: The Presence of Somatostatin Receptors in Rheumatoid Arthritis," Arthritis & Rheumatism, vol. 37, No. 10, pp. 1521–1527 (1994).

E.A. Woltering et al., "Somatostatin Analogues Inhibit Angiogenesis in the Chick Chorioallantoic Membrane," Journal of Surgical Research, vol. 50, pp. 245–251 (1991).

J.C. Watson et al., "Initiation of kdr Gene Transcription is Associated wth Conversion of Human Vascular Endothelium to an Angiogenic Phenotype," Surgical Forum, vol. 47, pp. 462–464 (1996).

M.O. Meyers et al., "Gene Upregulation of PDGF in Human Angiogenesis," Paper Presented at the Association for Academic Surgery, Seattle, Washington, Nov. 19–22, 1998.

W.D. Bloomer et al., "Therapeutic Application of Iodine–125 Labeled Iododeoxyuridine in an Early Ascites Tumor Model," Current Topics in Radiation Research Quarterly, vol. 12, pp. 513–525 (1977).

W.A.P. Breeman et al., "Studies on Radiolabeled Somatostatin Analogues in Rats and in Patients," Quarterly Journal of Nuclear Medicine, vol. 40, pp. 209–220 (1996).

P.L. Roberson et al., "Dosimetric Comparison of Bolus and Continuous Injections of CC49 Monoclonal Antibody in a Colon Cancer Xenograft Model," Supplement to Cancer, vol. 80, pp. 2567–2575 (1997).

Y. Nakabeppu, et al., "Radionuclide therapy of malignant pheochromocytoma with $^{131}$I–MIBG," Annals of Nuclear Medicine, vol. 8, No. 4, pp. 259–268 (1994).

W. Kaplan, et al., "Pulmonary Uptake to Technetium 99m Macroaggregated Albumin: A Predictor of Gastrointestinal Toxicity During Hepatic Artery Perfusion," Journal of Clinical Oncology, vol. 2, No. 11, pp. 1266–1269 (1984).

FIG. 6

METHOD TO ENHANCE TISSUE ACCUMULATION OF RADIOLABELED COMPOUNDS

The benefit of the Nov. 24, 1997 filing date of provisional application 60/160,087 (which was a conversion of nonprovisional application Ser. No. 08/977,520), now abandoned, is claimed under 35 U.S.C. §119(e).

Development of this invention was supported in part by the Department of Veterans Affairs. The Government may have certain rights in this invention.

This invention pertains to a method of increasing tissue accumulation and retention of radiolabeled compounds (radioligands), thus improving their therapeutic and diagnostic value.

Radiolabelled compounds are used for both tumor detection and tumor therapy. Many tumor cells have a higher density of cell receptors for various circulating compounds than do non-tumor cells; e.g., endocrine tumors show a high density of cell surface receptors for somatostatin, and brain gliomas show a high density of receptors for epidermal growth factor. Thus a radiolabeled compound that binds to these cellular receptors preferentially binds to the tumor cells. Additionally, angiogenesis, the formation of new blood vessels from established microvasculature, is a critical process for tumor growth. Primary tumors and metastases will not grow beyond 2 mm in diameter without an enhanced vascular supply. Angiogenic cells also have a higher density of cell receptors for various circulating compounds than do non-angiogenic vascular tissue; e.g., receptors for both somatostatin and vascular endothelial growth factor are higher in angiogenic tissue. Thus a tumor can also be detected by radiolabeled compounds binding to the angiogenic cells that are closely associated with the tumor cells.

An ideal tumor imaging agent would maximize the radioactivity at the target cells, and minimize the background signal, resulting in a well-defined image of the tumor foci. For example, $^{111}$In-DTPA-D-Phe-1-octreotide and $^{123}$I-vasoactive intestinal peptide, two receptor-based radioligands, have been used to localize primary endocrine tumors as well as metastatic liver lesions. See A. Kurtaran, et al., "Vasoactive Intestinal Peptide and Somatostatin Receptor Scintigraphy for Differential Diagnosis of Hepatic Carcinoid Metastasis," The Journal of Nuclear Medicine, vol. 38, pp. 880–881 (1997).

An ideal radioligand therapy agent would accumulate selectively in target cells. The effectiveness of radiotherapy is due to the destruction of dividing cells resulting from radiation-induced damage to cellular DNA. See W. D. Bloomer et al., "Therapeutic Application of Iodine-125 Labeled Iododeoxyuridine in an Early Ascites Tumour Model," Current Topics in Radiation Research Quarterly, vol. 12, pp. 513–25 (1977). In both therapeutic and imaging applications, any unbound, circulating radioligand is rapidly cleared by excretory systems, which helps protect normal organs and tissues. The radioligand may also be degraded by body processes which will increase the clearance of the free radioisotope. See G. A. Wiseman et al., "Therapy of Neuroendocrine Tumors with Radiolabelled MIBG and Somatostatin Analogues," Seminars in Nuclear Medicine, vol. XXV, No. 3, pp. 272–278 (1995).

In both tumor imaging and therapy, a clinical goal is to maximize the amount of radiolabeled compound taken up by the tumor. The amount of radioligand that accumulates in target cells depends on many factors, for example: (1) the concentration gradient of the radioligand between the blood and the targeted tissue; (2) the number of cellular receptors, membrane or intracellular, and the affinity of those receptors for the radioligand; (3) the relative concentrations of labeled and unlabeled ligand competing for a given receptor; (4) the recycling rate for the cellular receptors; (5) the capacity of the cell to store the radioligand; and (6) the degradation of the radioligand inside the cell. See R. K. Rippley et al., "Effects of Cellular Pharmacology on Drug Distribution in Tissues," Biophysical Journal, vol. 69, pp. 825–839 (1995).

Radiolabeled compounds have typically been administered by intravenous, bolus injection. In a few instances, radiolabeled compounds have been given as infusions over 30 to 60 min, usually to limit side effects of the drug, not to increase efficacy. See e.g., H. P. Kalofonos et al., "Antibody Guided Diagnosis and Therapy of Brain Gliomas using Radiolabeled Monoclonal Antibodies Against Epidermal Growth Factor Receptor and Placental Alkaline Phosphatase," The Journal of Nuclear Medicine, vol. 30, pp. 1636–45 (1989); I. Virgolini et al., "Vasoactive Intestinal Peptide-Receptor Imaging for the Localization of Intestinal Adenocarcinomas and Endocrine Tumors," The New England Journal of Medicine, vol. 331, pp. 1116–21 (1994); G. A. Wiseman et al., "Therapy of Neuroendocrine Tumors with Radiolabelled MIBG and Somatostatin Analogues," Seminars in Nuclear Medicine, vol. XXV, no. 3, pp. 272–78 (1995); S. W. J. Lamberts et al., "Somatostatin-Receptor Imaging in the Localization of Endocrine Tumors," The New England Journal of Medicine, vol. 323, pp. 1246–49 (1990); E. P. Krenning et al., "Somatostatin Receptor Scintigraphy with Indium-111-DTPA-D-Phe-1-Octreotide in Man: Metabolism, Dosimetry and Comparison with Iodine-123-Tyr-3-Octreotide," The Journal of Nuclear Medicine, vol. 33, pp. 652–58 (1992); E. P. Krenning et al., "Localisation of Endocrine-Related Tumours with Radioiodinated Analogue of Somatostatin," The Lancet, vol. 1989, no. 1, pp. 242–244 (1989). There is one report of an infusion duration of two (2) hours. See J. A. Carrasquillo et al., "Indium-111 T101 Monoclonal Antibody is Superior to Iodine-131 T101 in Imaging of Cutaneous T-Cell Lymphoma," The Journal of Nuclear Medicine, vol. 28, pp. 281–87 (1987).

The ability of a cell to take up a radiolabeled compound in the short term is limited by the number of cellular receptors or transport proteins for the compound on the cell membrane or within the cell. When the radioligand is administered by bolus injection, the binding pharmocokinetics dictate that uptake of the radioligand is linearly related to the amount injected only at low concentrations of the radioligand. At higher concentrations, the receptors for the radioligand become saturated. See H. Zhu et al., "Potential and Limitations of Radioimmunodetection and Radioimmunotherapy with Monoclonal Antibodies," The Journal of Nuclear Medicine, vol. 38, no. 5, pp. 731–41 (1997); and R. M. Kessler et al., "High Affinity Dopamine D2 Receptor Radioligands. 1. Regional Rat Brain Distribution of Iodinated Benzamides," The Journal of Nuclear Medicine, vol. 32, pp. 1593–1600 (1991). These saturated receptors are not able to bind more radioligand until either the receptor releases the radioligand, or the receptor-radioligand complex has been transported to another part of the cell and the receptor has been recycled to again bind a new molecule of the radioligand. Because the circulating unbound radioligand is rapidly eliminated, by the time the receptors are free to accept another molecule of the radioligand, the radioligand may no longer be present. Thus, the accumulation of radioligand depends on the availability of unbound radioligand, and on the recycling time of the cellular receptors and transport proteins.

The recycling of the cellular receptors depends on the fate of the ligand-receptor complex. Many, if not most, peptide compounds (including peptide and protein hormones) that bind to surface receptors are internalized as a ligand-receptor complex by endocytosis, i.e., invagination of the plasma membrane. Examples of peptides that have been shown to be internalized as part of a ligand-receptor complex include nerve growth factor, fibroblast growth factor, epidermal growth factor, platelet-derived growth factor, cholecystokinin, vascular endothelial growth factor, vasoactive intestinal peptide, gastrin-releasing peptide, leukemia inhibitory factor, somatostatin, oxytocin, bombesin, calcitonin, arginine vasopressin, angiotensin II, atrial natriuretic peptide, insulin, glucagon, prolactin, growth hormone, gonadotropin, thyrotropin-releasing hormone, growth hormone-releasing hormone, gonadotropin-releasing hormone, corticotropin-releasing hormone, interleukins, interferons, transferrin, substance P, neuromedin, neurotensin, neuropeptide Y, and various opioids. This internalization takes time—minutes or even hours. See G. Morel, "Internalization and Nuclear Localization of Peptide Hormones," Biochemical Pharmacology, vol. 47(1), pp. 63–76 (1994); D. Nouel et al., "Differential Internalization of Somatostatin in COS-7 Cells Transfected with $SST_1$ and $SST_2$ Receptor Subtypes: A Confocal Microscopic Study Using Novel Fluorescent Somatostatin Derivatives," Endocrinology, vol. 138, pp. 296–306 (1997); L.-H. Wang et al., "Ligand Binding, Internalization, Degradation and Regulation by Guanine Nucleotides of Bombesin Receptor Subtypes: A Comparative Study," Biochimica et Biophysica Acta, vol. 1175, pp. 232–242 (1993). Even monoclonal antibodies have been shown to be internalized into the cell. See O. W. Press et al., "Comparative Metabolism and Retention of Iodine-125, Yttrium-90, and Indium-111 Radioimmunoconjugates by Cancer Cells," Cancer Research, vol. 56, pp. 2123–29 (1996).

After internalization, many peptides translocate into the nucleus and even bind DNA. Peptides that been shown to accumulate in the nuclei of target cells include insulin, growth hormone, prolactin, nerve growth factor, somatostatin, epidermal growth factor, fibroblast growth factor, platelet-derived growth factor, and interferons. Nuclear binding sites have been described for gonadotropin-releasing hormone, gonadotropin, growth hormone, angiotensin II, prolactin, transferrin, insulin, various interleukins, glucagon, various opioids, and growth factors (including epidermal growth factor, nerve growth factor, platelet-derived growth factor and fibroblast growth factor). Insulin and epidermal growth factor have been shown to cause specific nuclear effects. See G. Morel, "Internalization and Nuclear Localization of Peptide Hormones," Biochemical Pharmacology, vol. 47(1), pp. 63–76 (1994); and P. M. Laduron, "From Receptor Internalization to Nuclear Translocation—New Targets for Long-Term Pharmacology," Biochemical Pharmacology, vol. 47, pp. 3–13 (1994).

Steroid hormones are known to diffuse through the plasma membrane and then either bind intracellular receptors and translocate to the nucleus, or directly bind receptors in the nucleus. See W. V. Welshons et al., "Nuclear Localization of Unoccupied Oestrogen Receptors," Nature, vol. 307, pp. 747–49 (1984). Classes of steroid hormones known to bind to intracellular receptors include progestins (e.g., progesterone), androgens (e.g., testosterone), glucocorticosteriods (e.g., hydrocortisone), mineralocorticoids (e.g., aldosterone), and estrogens (e.g., estradiol). See D. J. Sutherland et al., "Hormones and Cancer," The Basic Science of Oncology, 2d Ed. (I. F. Tannock and R. P. Hill, eds.), Chapter 13, pp. 207–231 (1992). Breast and prostate tumor cells are known to possess increased numbers of steroid hormone receptors.

One method that has been used to increase the tumor-to-background ratio of radioligand for therapy or imaging is to decrease the uptake of radioactivity by the background tissue by altering the rapidity of degradation or excretion. When the background radiation level decreases, the tumor-to-background ratio increases; however, the amount of radioligand accumulated by the tumor cell remains the same. Thus the actual therapeutic dose (the dose inside the cell) does not change, even though the tumor image will show more contrast against the background.

Methods that have been used to increase tumor cell uptake of the radioligand, and thus increase the therapeutic or diagnostic dose, include the following: using a radioligand more targeted to the tumor cells, using a radioligand with a higher diffusion rate into the tissue, changing the elimination rate of the radioligand, using a radioligand with a longer biologic half-life, using a radioisotope with a longer physical half-life, and using a higher dose of the radioligand. The radioligand has been administered either by a single bolus dose or by short infusion of up to 2 hours. Models have been developed to try to identify parameters that can be optimized to make the uptake more efficient. These models share the basic assumption that the radiolabeled compound is given in a single bolus dose. See Rippley et al. (1995); S.-E. Strand et al., "Pharmacokinetic Modeling," Medical Physics, vol. 20(2), Pt. 2, pp. 515–27 (1993); and H. Zhu et al., "Potential and Limitations of Radioimmnunodetection and Radioimmunotherapy with Monoclonal Antibodies," The Journal of Nuclear Medicine, vol. 38, no. 5, pp. 731–41 (1997). There is a need for a method to increase the accumulation of the radioligand by the target cells without an increase in destruction of normal cells.

Radiolabeled analogs of the peptide somatostatin have been studied for their effectiveness in tumor imaging and therapy. See E. A. Woltering et al., "The Role of Radiolabelled Somatostatin Analogs in the Management of Cancer Patients," Principles & Practice of Oncology, Vol. 9, pp. 1–15 (1995); U.S. Pat. No. 5,590,656; and U.S. Pat. No. 5,597,894. Endogenously produced somatostatin, a tetradecapeptide, inhibits release of several pituitary and intestinal factors that regulate cell proliferation, cell motility, or cellular secretion, including growth hormone, adrenocorticotropin hormone, prolactin, thyroid stimulating hormone, insulin, glucagon, motilin, gastric inhibitory peptide (GIP), vasoactive intestinal peptide (VIP), secretin, cholecystokinin, bombesin, gastrin releasing peptide (GRP), gastrin adrenocorticotropic hormone (ACTH), thyroid releasing hormone (TRH), cholecystokinin (CCK), aldosterone, pancreatic polypeptide (PP), various cytokines (e.g., interleukins, interferons), various growth factors (e.g., epidermal growth factor, nerve growth factor), and various vasoactive amines (e.g., serotonin).

Because somatostatin has a short biologic half-life (1 to 2 min), a variety of somatostatin peptide analogs have been produced by elimination of amino acids, by substitution of native L-amino acids with the corresponding D-amino acid isomers, by addition of an alcohol to the carboxy terminus of the molecule, or by various combinations of these approaches. See U.S. Pat. No. 5,597,894. Examples of somatostatin analogs include octreotide acetate, lanreotide, vapreotide ("RC-160"), and pentetreotide, all which have a longer biologic half-life. Multi-tyrosinated somatostatin analogues have been produced and shown to bind somatostatin cellular receptors. See U.S. Pat. No. 5,597,894.

Somatostatin receptors are found throughout the cell, including the cell membrane, Golgi apparatus, endoplasmic reticulum, vesicles, and nucleus. Somatostatin and its analogs are internalized by endocytosis of the ligand-receptor complex. See L. J. Hofland et al., "Internalization of the Radioiodinated Somatostatin Analog [$^{125}$I-Tyr$^3$] Octreotide by Mouse and Human Pituitary Tumor Cells: Increase by Unlabeled Octreotide," Endocrinology, vol. 136, pp. 3698–3706 (1995); Wiseman et al., (1995).

High densities of somatostatin receptors, especially somatostatin receptor subtype 2 (SST-2), have been found on cells from a wide variety of tumors, including endocrine tumors, melanomas, breast carcinomas, Merkel cell tumors, lymphomas, small cell lung carcinomas, gastrointestinal tumors, astrocytomas, gliomas, meningiomas, carcinoid tumors, islet cell tumors, renal cell carcinomas, neuroblastomas, and pheochromocytomas. See E. A. Woltering et al., "The Role of Radiolabeled Somatostatin Analogs in the Management of Cancer Patients," Principles & Practice of Oncology, Vol. 9, pp. 1–15 (1995); and E. A. Woltering et al., "Somatostatin Analogs: Angiogenesis Inhibitors with Novel Mechanisms of Action," Investigational New Drugs, vol. 15, pp. 77–86 (1997). The radiolabeled somatostatin analog $^{111}$In-Pentetreotide, known to bind SST-2 receptors on cell membranes, has been shown to bind to pituitary tumors, endocrine pancreatic tumors, carcinoids, paragangliomas, pheochromocytomas, medullary thyroid carcinomas, small-cell-lung cancers, neuroblastomas, meningiomas, breast carcinomas, renal cell carcinomas, gliomas, astrocytomas, melanomas, and lymphomas. $^{111}$In-Pentetreotide has also been used to treat metastatic glucagonoma and carcinoid tumors. See Wiseman et al., 1995; Krenning et al., "Radiotherapy with a radiabelled somatostatin analogue, [$^{111}$In-DTPA-D-Phe1]-octreotide. A Case History," Annals of the New York Academy of Sciences, vol. 733, pp. 496–506 (1996); and M. Fjalling et al., "Systemic radionuclide therapy using indium-111-DTPA-D-Phe-1-octreotide in midgut carcinoid syndrome," Journal of Nuclear Medicine, vol. 37, pp. 1519–21 (1996).

Radiolabeled somatostatin or somatostatin analogs have been used for tumor imaging and therapy, but have previously been administered either by bolus injection or by short infusion (up to 2 hours). See S. W. J. Lamberts et al., "Somatostatin-Receptor Imaging in the Localization of Endocrine Tumors," The New England Journal of Medicine, vol. 323, pp. 1246–49 (1990); E. P. Krenning et al., "Somatostatin Receptor Scintigraphy with Indium-111-DTPA-D-Phe-1-Octreotide in Man: Metabolism, Dosimetry and Comparison with Iodine-123-Tyr-3-Octreotide," The Journal of Nuclear Medicine, vol. 33, pp. 652–58 (1992); E. P. Krenning et al., "Localisation of Endocrine-Related Tumours with Radioiodinated Analogue of Somatostatin," The Lancet, vol. 1989, no. 1, pp. 242–244 (1989); W. A. P. Breeman et al., "Studies on Radiolabelled Somatostatin Analogues in Rats and in Patients," The Quarterly Journal of Nuclear Medicine, vol. 40, pp. 209–220 (1996); and E. P. Krenning et al., "Somatostatin Receptor Scintigraphy with [$^{111}$In-DTPA-D-Phe$^1$]- and [$^{123}$I-Tyr$^3$]-octreotide: the Rotterdam Experience with More than 1000 Patients," European Journal of Nuclear Medicine, vol. 20, pp. 716–31 (1993).

Radiolabeled somatostatin analogs that have been used for tumor imaging or therapy include $^{111}$In-pentetreotide (($^{111}$In-DTPA-D-Phe$^1$)-octreotide), ($^{111}$In-DOTA$^0$-D-Phe$^1$-Tyr$^3$)-octreotide, ($^{90}$Y-DOTA$^0$-D-Phe$^1$-Tyr$^3$)-octreotide, ($^{86}$Y-DOTA$^0$-D-Phe$^1$-Tyr$^3$)-octreotide,($^{111}$In-DTPA-D-Phe$^1$)-RC-160, $^{99m}$Tc-RC-160, $^{99m}$Tc-octreotide, $^{188}$Re-RC-160, $^{123}$I-tyr$^3$-octreotide, $^{125}$I-tyr$^3$-octreotide, $^{125}$I-lanreotide, $^{90}$Y-DOTA-lanreotide, and $^{131}$I-WOC-3. See, e.g., Woltering et al., 1995; M. L. Thakur et al., "Radiolabeled Somatostatin Analogs in Prostate Cancer," Nuclear Medicine & Biology, Vol. 24, pp. 105–113 (1997); M. de Jong et al., "Yttrium-90 and Indium-111 Labelling, Receptor Binding and Biodistribution of [DOTA$^0$, D-Phe$^1$. Tyr$^3$] octreotide, a Promising Somatostatin Analogue for Radionuclide Therapy," European Journal of Nuclear Medicine, vol. 24, pp. 368–371 (1997); W. A. P. Breeman et al., "A New Radiolabelled Somatostatin Analogue [$^{111}$In-DTPA-D-Phe$^1$]RC-160: Preparation, Biological Activity, Receptor Scintigraphy in Rats and Comparison with [$^{111}$In-DTPA-D-Phe$^1$]octreotide," European Journal of Nuclear Medicine, vol. 21, no. 4, pp. 323–335 (1994); W. A. P. Breeman et al., "Studies on Radiolabeled Somatostatin Analogues in Rats and in Patients," The Quarterly Journal of Nuclear Medicine, vol. 40, no. 3, pp. 209–219 (1996); M. Fjailing et al., "Systemic Radionuclide Therapy Using Indium-111-DTPA-D-Phe$^1$-Octreotide in Midgut Carcinoid Syndrome," Journal of Nuclear Medicine, vol. 37, pp. 1519–1521 (1996); H. Kolan et al., "Sandostatin® Labeled with $^{99m}$Tc: In Vitro Stability, In Vivo Validity and Comparison with $^{111}$In-DTPA-Octreotide," Peptide Research, vol. 9, no. 3, pp. 144–150 (1996); I. Virgolini et al., "'MAURITIUS': Biodistribution, Safety and Tumor Dose in Patients Evaluated for Somatostatin Receptor-Mediated Radiotherapy," Paper Submitted to Journal of Nuclear Medicine (1997); and U.S. Pat. No. 5,597,894.

Somatostatin analogs have also been demonstrated to inhibit angiogenesis in tumors. A primary tumor initiates neovascularization by angiogenic stimulation. See M. S. O'Reilly, "Angiostatin: An Endogenous Inhibitor of Angiogenesis and of Tumor Growth," in I. Goldberg et al. (eds.), Regulation of Angiogenesis, pp. 273–294 (1997). The growth of a solid tumor is dependent on neovascularization. This angiogenic tissue has been shown to be rich in somatostatin receptors subtype 2 (SST-2), and to be inhibited by somatostatin analogs known to bind SST-2 receptors, e.g., octreotide acetate, RC-160, and lanreotide. See E. A. Woltering et al., "The Role of Radiolabeled Somatostatin Analogs in the Management of Cancer Patients," Principles & Practice of Oncology, Vol. 9, pp. 1–15 (1995); E. A. Woltering et al., "Somatostatin Analogs: Angiogenesis Inhibitors with Novel Mechanisms of Action," Investigational New Drugs, vol. 15, pp. 77–86 (1997); P. C. Patel et al., "Postreceptor Signal Transduction Mechanisms Involved in Octreotide-Induced Inhibition of Angiogenesis," Surgery, vol. 116, pp. 1148–52 (1994); R. Barrie et al., "Inhibition of Angiogenesis by Somatostatin and Somatostatin-like Compounds Is Structurally Dependent," Journal of Surgical Research, vol. 55, pp. 446–450 (1993); and E. A. Woltering et al., "Somatostatin Analogues Inhibit Angiogenesis in the Chick Chorioallantoic Membrane," Journal of Surgical Research, vol. 50, pp. 245–251 (1991).

Angiogenic blood vessels have SST-2 receptors at a higher density than vessels from normal tissues. See J. C. Watson et al., "Up-Regulation of Somatostatin Receptor Subtype 2 (SST-2) mRNA Occurs During the Transformation of Human Endothelium to the Angiogenic Phenotype," Paper Presented at the 12th International Symposium on Regulatory Peptides, Copenhagen, Denmark, September 1996; and J. C. Watson et al., "SST-2 Gene Expression Appears During Human Angiogenesis," Regulatory Peptides, vol. 64, p. 206 (Abstract) (1996). Radiolabeled somatostatin analogs binding to SST-2 receptors on tumor vessels have been used for radioimaging and radiotherapy. The tumor's size deceases because blood vessel growth is inhibited by the radiolabeled compound. See J. C. Reubi et al., "High Density of Somatostatin Receptors in Veins Surrounding Human Cancer Tissue: Role in Tumor-Host Interaction?," International Journal of Cancer, vol. 56, pp. 681–88 (1994). Pathologic blood vessel growth has also been implicated in several other disease conditions, including retinopathy of prematurity, diabetic retinopathy, glaucoma, tumor growth, rheumatoid arthritis, and inflammation. See Barrie et al., 1993. In fact, $^{111}$In-pentetreotide has been used to localize areas of joints affected by rheumatoid arthritis. See P. M. Vanhagen et al., "Somatostatin Receptor Imaging: The Presence of Somatostatin Receptors in Rheumatoid Arthritis," Arthritis & Rheumatism, vol. 37, no. 10, pp. 1521–27 (1994).

Angiogenic cells have also been shown to express the vascular endothelial growth factor (VEGF) receptor gene, kdr, while quiescent vascular cells did not express this receptor gene. Both angiogenic and quiescent cells expressed the VEGF receptor gene, flt-1. See J. C. Watson et al., "Initiation of kdr Gene Transcription is Associated with Conversion of Human Vascular Endothelium to an Angiogenic Phenotype," Surgical Forum, vol. 47, pp. 462–64 (1996).

Non-radiolabeled somatostatin analogs have been used to inhibit growth hormone secretion by infusion from an implantable pump system to avoid intermittent growth hormone release between injections, and to avoid the inconvenience to the patient of frequent subcutaneous injections. See G. Hildebrandt et al., "Results of Continuous Long Term Intravenous Application of Octreotide via an Implantable Pump System in Acromegaly Resistent to Operative and X-ray Therapy," Acta Neurochirurgica, vol. 117, pp. 160–65 (1992). Thus the administration of the hormone by infusion allowed the concentration of the hormone to remain at a constant level in the blood stream. The objective was not to increase accumulation of the hormone inside the cells.

Infusion has also been suggested for uptake of a radiolabeled pyrimidine analog for incorporation into the DNA during DNA synthesis when the cell is in a growth phase. Pyrimidine does not bind to a cellular receptor, but instead is used as a building block for synthesizing new DNA. Because the radiolabeled pyrimidine in the general circulation was rapidly dehalogenated, infusion was suggested for increased uptake by solid tumors (e.g., breast cancer), which are known to have a slower growth rate and thus a lower percentage of cells in a growth phase at any one time than liquid tumors (e.g., leukemia). Infusion was suggested to maintain a level of radiolabeled compound in the circulation, so cells dividing at different cycles would have access to the radioligand for incorporation into DNA during DNA synthesis. No corresponding experimental data were given. No reference was made to radiolabeled compounds that bind to a cellular receptor. See Bloomer et al., 1977.

U.S. Pat. No. 5,590,656 discloses using a bolus injection of radiolabeled somatostatin to detect and differentiate neoplastic tissues.

U.S. Pat. No. 5,597,894 discloses using multi-tyrosinated somatostatin analogs given by bolus injection or short infusion (up to 60 min) to diagnose and treat tumors with peptide-specific surface receptors.

International Application (PCT) No. WO 91/01144 discloses using labeled polypeptide derivatives delivered by a single bolus injection or by a short infusion up to about 60 min for in vivo imaging of target tissues or therapy.

Radioimaging and radiotherapy are increasingly important in identifying and killing unwanted tumor cells. The effectiveness of the radioligand depends on the concentration that is accumulated in the target cells. Although methods have been developed to increase the tumor to background ratio, few methods have actually increased the concentration of the radioligand inside either the tumor cells or closely associated angiogenic cells. Thus, there is a need for a method to increase the accumulation and retention of radioligand inside the target cells without an increase in the destruction of normal body cells.

We have discovered that administering a radioisotopic compound by infusion over a period of time greater than two hours, preferably greater than twelve hours, greatly increases the maximum radioactivity that accumulates in the target cell. Accumulation of the radiolabeled compound in target tissues can be about five times higher than that resulting from bolus injection or short infusion methods. This method enhances the tumor-to-background radioactivity ratio by increasing the amount of radioligand accumulated inside the target cells. This method may be used with any radiolabeled compound whose cellular uptake rate is limited by binding to a cellular receptor or to a transport protein. Once the radiolabeled compound is internalized, the biological half-life plays no more than a minor role in the residence time. The primary factor governing residence time after internalization is the physical half-life of the radioisotope.

BRIEF DESCRIPTION OF THE DRAWINGS

FIG. 3 illustrates the binding and internalization of $^{125}$I-WOC-4a.

FIG. 4 illustrates the binding and internalization of $^{131}$I-WOC-4a.

Figure 6:
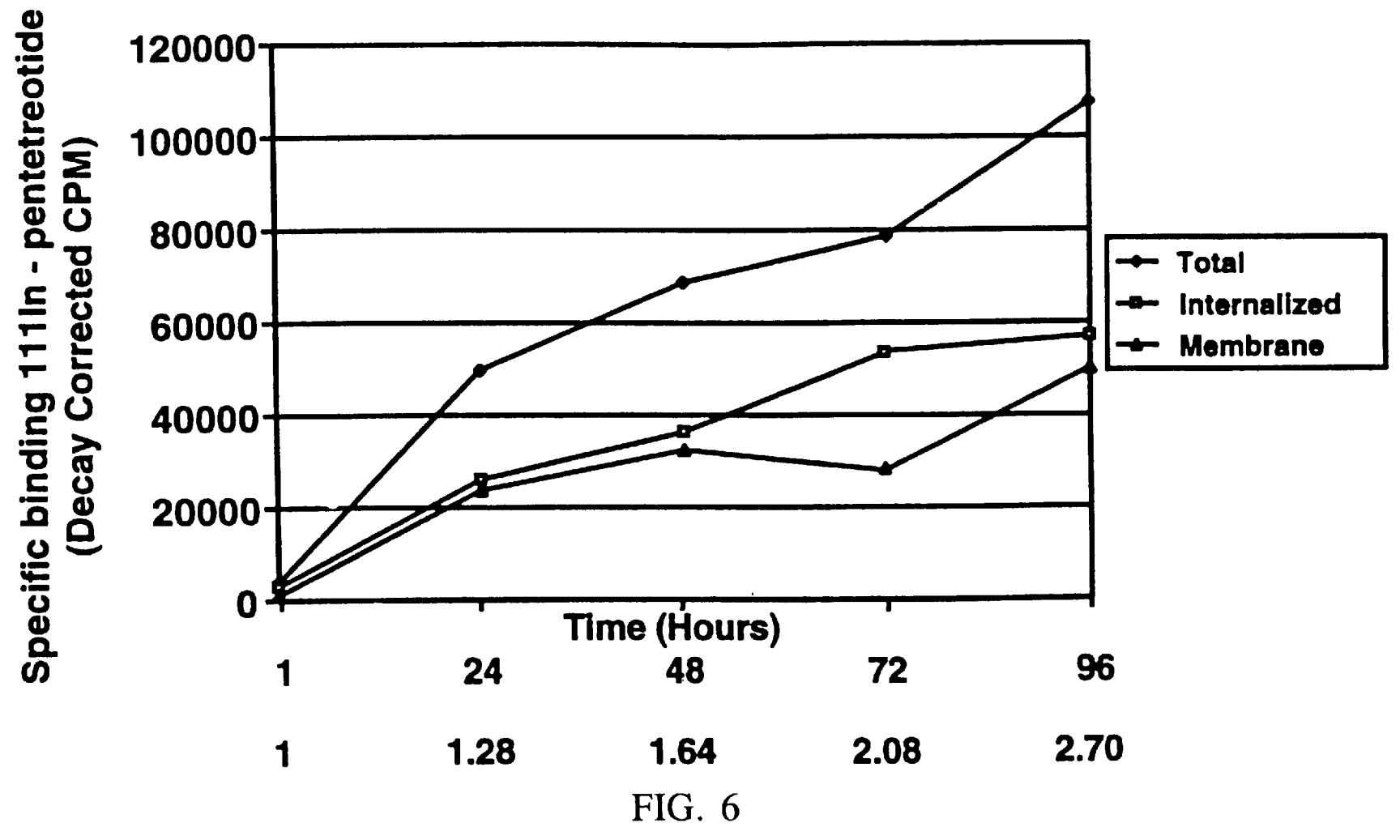

FIG. 6 illustrates the binding and internalization of $^{111}$In-pentetreotide.

FIG. 7 illustrates the rate of loss of radioactivity from cells exposed to $^{123}$I-WOC-4a.

Figure 1:
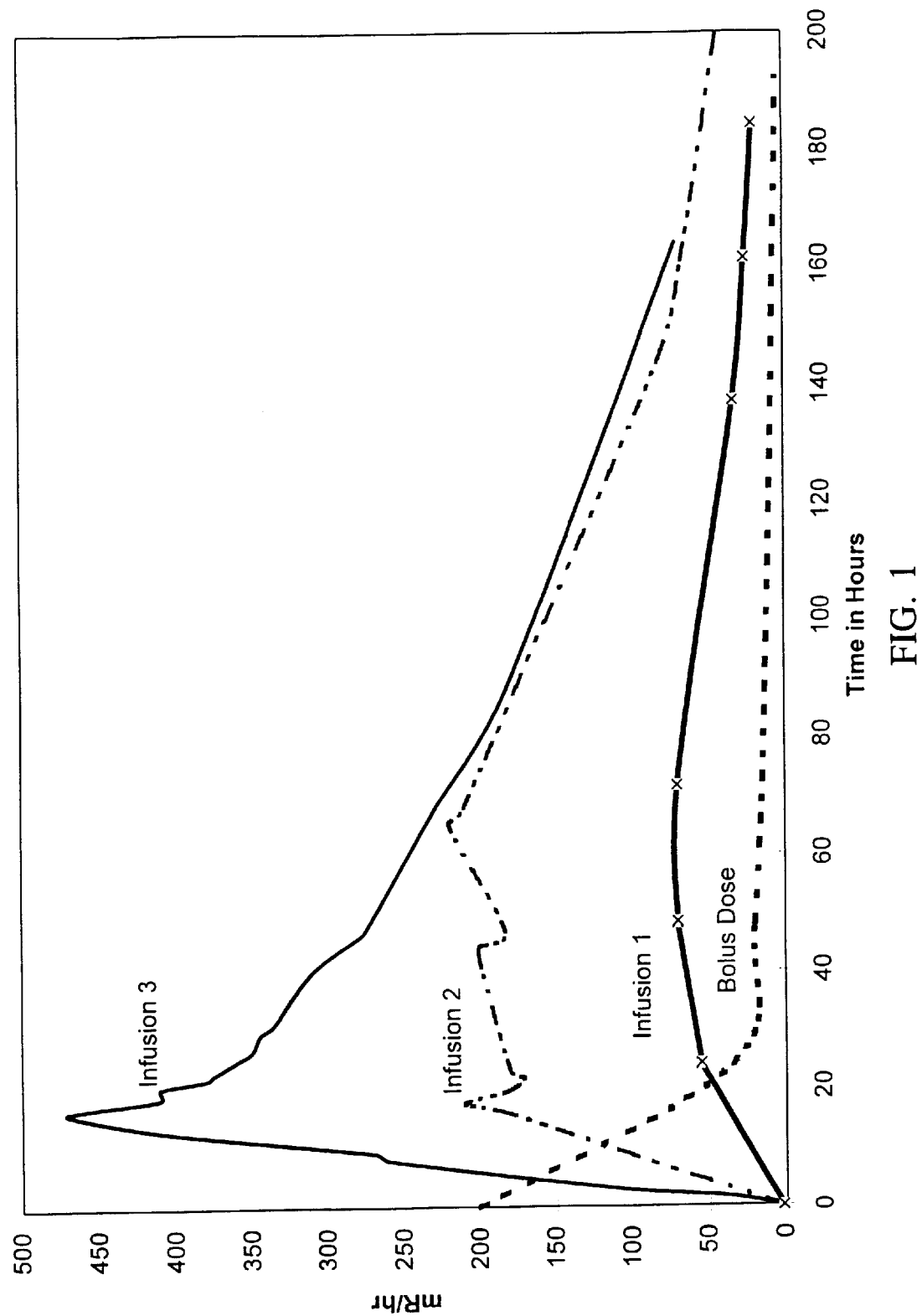
FIG. 1 illustrates the uptake of $^{111}$In-pentetreotide as a function of time in a single patient for different methods of administration.

We have shown that infusion over a period greater than 2 hr, preferably greater than about 12 hr, more preferably 24 hr, greatly increases the measured radioactivity inside the target cells. The infusion method increases the accumulated radioactivity in tumor or angiogenic cells for almost all radiolabeled receptor-dependent peptides and steroids. Without wishing to be bound by this theory, the underlying mechanism is believed to be as follows. Binding to a cellular receptor (whether membrane, cytoplasmic, or nuclear) or to a transport protein, which is necessary for peptides and steroids to affect cellular processes, occurs over a finite period of time. If an excess of radiolabeled compound (more than the receptor or the transport protein can bind at any one moment) is administered, the cell's take-up of that compound is limited by the number of available receptors or transport protein molecules. The remaining unbound compound is subject to degradation or excretion. By the time the receptor is free to bind another molecule, the circulating radiolabeled compound has been partially or completely eliminated. However, if the rate of receptor binding and subsequent transport of the radiolabeled compound is matched with the rate of administration of the radiolabeled compound, then circulating unbound radioligand will be available to bind to the recycled receptors. Thus, the effective dose of the drug, i.e., its intracellular accumulation, is optimized.

This theory is consistent with the observation that compounds that are internalized (e.g., peptides, hormones, cytokines, growth factors, and steroids) are resistant to competition or have a lower rate of competition than compounds that bind only on the cell surface. Experiments that have monitored the rate of internalization or translocation of radioligands have all considered short binding periods (0 to 4 hr). We have demonstrated in vitro that, for radiolabeled somatostatin analogs for a time up to at least 120 hr, there is a progressive translocation of membrane-bound receptors and cytoplasmic receptors to the nucleus. Since the radiolabeled compounds bind not only to nuclear receptors but also specifically to the DNA, effective radiotherapies may use radiolabeled compounds labeled with low-energy emitters, such as Auger electrons, which have a short radius of emitted radioactivity. These electrons must be incorporated into the nucleus to damage the DNA. Auger emitters inhibit cell division with minimal effect on neighboring cells.

To optimize cellular accumulation of a radiolabeled compound, its rate of infusion is matched with its rate of cellular uptake and translocation, preferentially into the nucleus, more preferentially onto the DNA. Matching the rate of binding, internalization, and translocation results in more efficient accumulation within the cell than is possible by bolus or short-term infusion therapy. The novel long-term infusion technique allows receptors to be recycled over and over again, resulting in increased internalization, translocation, and ultimately, deposition in the cytoplasm, its organelles, the nucleus, or DNA. This increase in accumulation of radioactivity provides optimal imaging and optimal in situ radiation therapy.

More efficient uptake of the radiolabeled compound by the cell provides more efficient utilization of the compound, i.e., more compound bound in target cells, and less exposure of a toxic compound to normal cells.

We have demonstrated that once a compound is internalized in the cell, it is less available for competition or degradation. Thus, the biologic half-life of the compound becomes less important, and the physical half-life of the radioisotope becomes the rate-limiting step. Many peptides, growth factors, and hormones have very short biologic half-lives. If radiolabeled peptides, growth factors, or hormones are given by infusion, and are translocated into the cell where they are no longer subject to active competition with unlabeled hormones, and are protected from degradation and excretion, the physical half-life of the isotope becomes more important in determining the amount of radioactivity accumulated in the cell than the biologic half-life.

The uptake of the radiolabeled compound for either radioimaging or radiotherapy can be monitored using nuclear medicine scintigraphy procedures known in the field, for example a nuclear medicine camera. Regions of interest can be displayed as computer images to assess uptake of the radiolabeled compound. Radioactivity and its duration in the tumor or angiogenic cells may be calculated. Infusional therapy provides higher effective doses that remain for a longer time in the tumor or angiogenic cells.

The novel method enhances the tumor-to-background ratio by increasing the level of radioactivity accumulated in the target cells, not by merely decreasing the background signal.

The term "target cells" refers to tumor cells or angiogenic cells that contain a higher concentration of membrane or internal receptors or transport proteins that bind a receptor-dependent peptide or receptor-dependent steroid than the concentration of the same receptor or transport protein found in non-target cells.

The term "radiolabeled compound" or "radioligand" includes a receptor-dependent peptide or receptor-dependent steroid that is complexed with a radioisotope, and is useful as a pharmaceutical, e.g. a radiopharmaceutical for in vivo imaging of target tissues or for therapy. The term "radiolabeled compound" also includes a compound with a chelator linked to the receptor-dependent peptide to bind the radioisotope.

The term "receptor-dependent" refers to compounds whose effect on a cell depends on binding to a cellular receptor, including both membrane-bound and intracellular receptors. The term "receptor-dependent peptides" includes natural peptides or proteins isolated from nature or fermentation of cells, e.g. produced through genetic engineering, or synthesized, as well as derivatives or analogs. While not limiting the scope of this invention, examples of receptor-dependent peptides that may be used include antibodies, growth factors, peptide and protein hormones, interferons, cytokines, and analogs and derivatives thereof. While not limiting the scope of this invention, specific examples of receptor-dependent peptides include nerve growth factor, fibroblast growth factor, epidermal growth factor, platelet-derived growth factor, cholecystokinin, vascular endothelial growth factor, vasoactive intestinal peptide, gastrin-releasing peptide, leukemia inhibitory factor, somatostatin, oxytocin, bombesin, calcitonin, arginine vasopressin, angiotensin II, atrial natriuretic peptide, insulin, glucagon, prolactin, growth hormone, gonadotropin, thyrotropin-releasing hormone, growth hormone-releasing hormone, gonadotropin-releasing hormone, corticotropin-releasing hormone, interleukins, interferons, transferrin, substance P, neuromedin, neurotensin, neuropeptide Y, opioids, and their derivatives and analogs.

The terms "derivatives" and "analogs" are understood to be particular peptides or proteins, wherein one or more amino acid units have been omitted or replaced by one or more different amino acid units, or wherein one or more functional groups have been replaced by one or more other functional groups, or wherein one or more groups have been replaced by one or several other isosteric groups. In general, the term covers all derivatives of a receptor-dependent peptide that exhibit a qualitatively similar effect to that of the unmodified peptide. For example, they may be more or less potent than the naturally occurring peptide, bind to a different receptor subtype, or have a longer biologic half-life. The term also covers agonists and antagonists to the naturally occurring peptide that bind the same receptor. Radiolabeled peptides may be purchased from a commercial supplier (e.g., New England Nuclear or ICN Pharmaceuticals, Inc.), or prepared by techniques known in the art (see, for instance, U.S. Pat. No. 5,597,894 and PCT/WO 91/01144).

The term "receptor-dependent steroid" includes natural steroids or steroids isolated from nature or synthesized, as well as derivatives or analogs. While not limiting the scope of this invention, examples of receptor-dependent steroids that may be used include the steroid hormones, such as estrogen, progesterone, testosterone, glucocorticosteroids, mineralocorticoids, and their analogs.

Radiolabeled steroids may be prepared by techniques known in the art (see, for example, C. S. Dence et al., "Carbon-11-Labeled Estrogens as Potential Imaging Agents for Breast Tumors," Nuclear Medicine & Biology, vol. 23, pp. 491–496 (1996) and R. B. Hochberg, "Iodine-125-Labeled Estradiol: A Gamma-Emitting Analog of Estradiol That Binds to the Estrogen Receptor," Science, vol. 205, pp. 1138–1140, (1979)), or purchased from a commercial supplier.

Suitable radioisotopes include radioisotopes that emit alpha, beta, or gamma radiation, preferably gamma radiation which is easier to image using current technology. Examples are radioisotopes derived from Gallium, Indium, Technetium, Yttrium, Ytterbium, Rhenium, Platinum, Thallium, and Astatine, e.g., $^{67}$Ga, $^{111}$In, $^{99m}$Tc, $^{90}$Y, $^{86}$Y, $^{169}$Yb, $^{188}$Re, $^{195m}$Pt, $^{201}$Ti, $^{211}$At. Radioisotopes suitable for therapeutic treatment include Auger-electron-emitting radioisotopes, e.g. $^{125}$I, $^{123}$I, $^{124}$I, $^{129}$I, $^{131}$I, $^{111}$In, $^{77}$Br, and other radiolabeled halogens. The choice of a suitable radioisotope depends on a variety of factors including the type of radiation emitted, the emission energies, the distance over which energy is deposited, and the physical half-life of the radioisotope. Preferred radioisotopes are those having a radioactive half-life corresponding to, or longer than, the biological half-life of the receptor-dependent compound. Preferably the radioisotope has a half-life between about 1 hour and 60 days, preferably between 5 hours and 60 days, more preferably between 12 hours and 60 days. $^{125}$I has an advantage over other emitters that produce high-energy gammna rays (i.e., $^{111}$In and $^{113}$I) which require inpatient hospitalization and isolation. $^{125}$I will allow the development of outpatient-based treatments due to the limited amounts of radiation that escapes the body.

The term "radiolabeled somatostatin" includes, for example, $^{111}$In-DPTA-somatostatin, $^{90}$Y-DOTA-somatostatin, and $^{125}$I-somatostatin.

The term "radiolabeled somatostatin analog" includes, for example, $^{111}$In-pentetreotide ($^{111}$In-DTPA-D-Phe$^{1}$-octreotide), ($^{111}$In-DOTA$^{0}$-D-Phe$^{1}$-Tyr$^{3}$)-octreotide, ($^{90}$Y-DOTA$^{0}$-D-Phe$^{1}$-Tyr$^{3}$)-octreotide, ($^{86}$Y-DOTA$^{0}$-D-Phe$^{1}$-Tyr$^{3}$)-octreotide, $^{111}$In-DTPA-D-Phe$^{1}$-RC-160, $^{99m}$Tc-RC-160, $^{99m}$Tc-CPTA-RC-160, $^{123}$I-RC-160, $^{125}$I-RC-160, $^{131}$I-RC-160, $^{99m}$Tc-octreotide, $^{188}$Re-RC-160, $^{123}$I-tyr$^{3}$-octreotide, $^{125}$I-tyr$^{3}$-octreotide, $^{131}$I-tyr-$^{3}$-octreotide, $^{125}$I-lanreotide, $^{123}$I-lanreotide, $^{131}$I-lanreotide, $^{90}$Y-DOTA-lanreotide, $^{86}$Y-DOTA-lanreotide, $^{111}$In-DPTA-lanreotide, $^{111}$In-DOTA-lanreotide, $^{111}$In-DPTA-somatostatin, $^{90}$Y-DOTA-somatostatin, $^{86}$Y-DOTA-somatostatin, $^{125}$I-somatostatin, $^{131}$I-WOC-3b, $^{125}$I-WOC-3b, $^{131}$I-WOC-4a, $^{125}$I-WOC-4a, $^{125}$I-JIC-2D, $^{123}$-JIC-2D, and $^{131}$I-JIC-2D.

The term "cellular receptor" includes membrane-bound receptors, intracellular receptors, and binding sites inside organelles, including endosomes, ribosomes, lysosomes, mitochondria, nuclei, vesicles, endoplasmic reticulum, sarcoplasmic reticulum, and Golgi bodies.

Infusion may be performed by any convenient route, including intravenous, oral, intraperitoneal, intratumoral, subcutaneous, intraarterial, intramuscular, or by slow-release formulation. The term "infusion" includes the use of repeated short interval bolus doses of compounds with physical or biologic half-lives that render multiple short-interval bolus doses physiologically equivalent to continuous infusion. The radiolabeled compound may be infused in free form or together with one or more pharmaceutically acceptable carriers or diluents.

The term "residence time" refers to the accumulation of radiolabeled compound by the target cell per dose of radiolabeled compound given over time. Accumulated radiolabeled compound is measured by the area under a curve when the measured radioactivity in the target cell is plotted as a function of time.

The amount of radiolabeled compound to be administered in radioimaging is an amount effective to enable imaging by nuclear medicine scintigraphic procedures known in the art, e.g., single photon emission computerized tomography (SPECT), or positron emission tomography (PET), or detected by an ion chamber survey meter, or a gamma probe, or a solid state detector. The amount is determined by the biologic and physical half-life of the radiolabeled compound, the type and location of the tumor, and patient-dependent variables including size, weight, and tumor load.

The amount of radiolabeled compound to be administered in radiotherapy is determined by the specific condition to be treated, the radiolabeled compound used, and patient-dependent variables, including size, weight, receptor density in the target cells, and the severity of disease. The efficacy of the therapy can be assessed by monitoring techniques well known in the art, including radioimaging and monitoring as described above.

EXAMPLE 1

A 36-year-old white female patient with metastatic small cell carcinoma received a high dose of $^{111}$In-pentetreotide in ten separate sessions, the initial two occasions before monitoring of tissue accumulation began. During and after each administration of the last eight doses, a tumor in the left side of the neck was monitored for radioligand uptake with an ion chamber survey meter, a Victoreen 450P ion chamber, which measures external gamma dose rates. Administration of the initial seven doses were by bolus injection. The last three doses were delivered by infusion with various activities of radioligand.

In each of five successive months, a bolus injection of about 180 mCi of $^{111}$In-pentetreotide (OctreoScan®, Mallinckrodt Medical, Inc., St. Louis, Mo.) was given. The external gamma dose rates from radioligand accumulation in the neck tumor area were measured immediately and 24 hr after injection. After the treatment of the fifth month, the patient was monitored for radioligand uptake for an extended period—at 2, 4, and 8 days after the injection. These data are shown below in Table 1 and are also presented in FIG. 1 as the lower curve labeled "Bolus Dose."

TABLE 1

Bolus Injections

| Month of Bolus Dose | Amount of Radioligand Injected (mCi) | Time After Injection (hr) | External Dose Accumulation (mR/hr) | Ratio (mR/hr/mCi) |
|---|---|---|---|---|
| Month 1 | 179.9 | 24 | 80 | 0.444691 |
| Month 2 | 160.6 | 24 | 28 | 0.174346 |
| Month 3 | 182.6 | 24 | 33.20 | 0.181818 |
| Month 4 | 169.5 | 24 | 27.2 | 0.160472 |
| Month 5 | 178.8 | 24 | 34.4 | 0.192394 |
| Month 5 |  | 72 | 19.85 |  |
| Month 5 |  | 120 | 11.46 |  |
| Month 5 |  | 216 | 3.82 |  |

Four months after the final bolus dose, the first dose by infusion ("Infusion 1") was administered. A dose equivalent to the previous bolus dose (175.9 mCi) was given, but the radioligand was administered by infusion over 72 hr at a constant rate of 2.5 mCi/hr. These data are given in Table 2. The data are also presented as a curve marked "Infusion 1" in FIG. 1.

TABLE 2

Infusion Dose 1

| Infusion Duration (hr) | Amount Radioligand Delivered* (mCi) | Time from Initial Infusion (hr) | External Dose Accumulation (mR/hr) | Maximal Ratio (mR/hr/mCi) |
|---|---|---|---|---|
| 24 | 53.52 | 0 | 2.0 | 1.027729 |
|  |  | 24 | 55 |  |
| 24 | 52.62 | 24.5 | 54.8 | 0.659505 |
|  |  | 48 | 70 |  |
| 24 | 50.75 | 49 | 69.7 | 0.446169 |
|  |  | 72 | 70 |  |
|  |  | 137 | 32.9 |  |
|  |  | 161 | 25 |  |
|  |  | 185 | 20 |  |
|  |  | 214 | 15.4 |  |
| 72 | 156.89 |  |  |  |

*Adjusted for Radioactive Decay.

One month later, in "Infusion 2," the total dose was increased to 389.2 mCi. By infusion, 189.8 mCi of the radioligand was given over the first 24 hr, 108.6 mCi over the second 24 hr, and 90.8 mCi over the third 24 hr. For each 24 hr period, the infusion rate was kept constant. These data are shown in Table 3 and are represented in FIG. 1 as the curve labeled "Infusion 2."

TABLE 3

Infusion Dose 2

| Infusion Duration (hr) | Amount Radioligand Delivered* (mCi) | Time from Initial Infusion (hr) | External Dose Accumulation (mR/hr) | Maximal Ratio (mR/hr/mCi) |
|---|---|---|---|---|
| 20 | 189.76 | 0 | 2 | 1.106654 |
|  |  | 16 | 180 |  |
|  |  | 17 | 210 |  |
|  |  | 20 | 181 |  |
| 22 | 108.62 | 22 | 171 | 0.670287 |
|  |  | 23 | 180 |  |
|  |  | 42 | 200 |  |
| 24 | 90.84 | 44 | 200 | 0.565236 |
|  |  | 47 | 183 |  |
|  |  | 65 | 220 |  |
|  |  | 68 | 210 |  |
|  |  | 144 | 81 |  |
|  |  | 161 | 66 |  |
| 66 | 389.22 |  |  |  |

*Adjusted for Radioactive Decay.

One month later, a third dose was administered by infusion ("Infusion 3"). A dose of 301 mCi was infused the first 24 hr period. In two subsequent 24 hr periods, 25 and 21 mCi were infused. The data are presented in Table 4 and are represented in FIG. 1 by the line labeled "Infusion 3".

TABLE 4

Infusion Dose 3

| Infusion Duration (hr) | Amount Radioligand Delivered* (mCi) | Time from Initial Infusion (hr) | External Dose Accumulation (mR/hr) | Maximal Ratio (mR/hr/mCi) |
|---|---|---|---|---|
| 17 | 301.07 | 0 | 0.68 | 1.561 |
|  |  | 2 | 36 |  |
|  |  | 3 | 90 |  |
|  |  | 4 | 144 |  |
|  |  | 8 | 260 |  |
|  |  | 9 | 270 |  |
|  |  | 13 | 400 |  |
|  |  | 16 | 470 |  |
|  |  | 17 | 460 |  |
|  |  | 19 | 410 |  |
| 24 | 29.93 | 20 | 410 |  |
|  |  | 22 | 380 |  |
|  |  | 23 | 375 |  |
|  |  | 25 | 360 |  |
|  |  | 26 | 350 |  |
|  |  | 29 | 345 |  |
|  |  | 30 | 340 |  |
|  |  | 31 | 335 |  |
|  |  | 40 | 310 |  |
| 24 | 20.48 | 46 | 280 |  |
|  |  | 47 | 275 |  |
|  |  | 67 | 230 |  |
|  |  | 90 | 179 |  |
|  |  | 164 | 70 |  |
| 65 | 346.49 |  |  |  |

*Adjusted for Radioactive Decay.

Based on the observations from the final bolus dose and the first two infusion doses, it is evident that an equivalent dose administered by the different methods accumulated at very different rates. With a bolus injection of 178.8 mCi, the maximum external gamma dose rate occurred soon after the injection, and decreased to about 34 mR/hr at 24 hr post injection, a 24 hr ratio of 0.19 mR/hr measured external dose for each mCi delivered. For Infusion Dose 1, with an infusion rate of 2.5 mCi per hour for 3 days, an increase was seen both in the area under the accumulation curve (the total amount of radiation absorbed by the tumor) and in the peak external radiation dose rate (mR/hr surface contact). The dose rate measured about 55 mR/hr after only one-third of the radioligand had been infused, and this rate was maintained or exceeded for the next three days. The highest mR/mCi ratio of 1.03 occurred after the first 24 hr infusion, and was almost five times higher than the highest ratio from the bolus injection. The slope of the dose accumulation curve was maximal during the first 24 hr, and then flattened over the next 48 to 72 hr, implying that the system had reached a limit with minimal subsequent uptake. After 24 hr, the cellular "feedback" mechanisms slowed uptake.

When the bulk of the dose was infused in the first 24 hr as in Infusions 2 and 3, 189.8 and 301 mCi respectively, and the infusion rate was then lowered for subsequent 24 hr periods, a greater area under the curve and a higher peak activity (220 and 470 mR/hour) were achieved. These data indicate the importance of administering a large dose during the first 24 hr before the internal "feedback" mechanisms slow the rate of uptake.

The differences among the four curves are not intuitive. The data suggest that the radioligand was protected from removal by degradation, competition, or excretion once it was incorporated into the cell, and that the cellular transport machinery continued to import radioligand despite higher concentrations inside the cell until "feedback" mechanisms slowed uptake at 16 to 24 hr.

Figure 2:
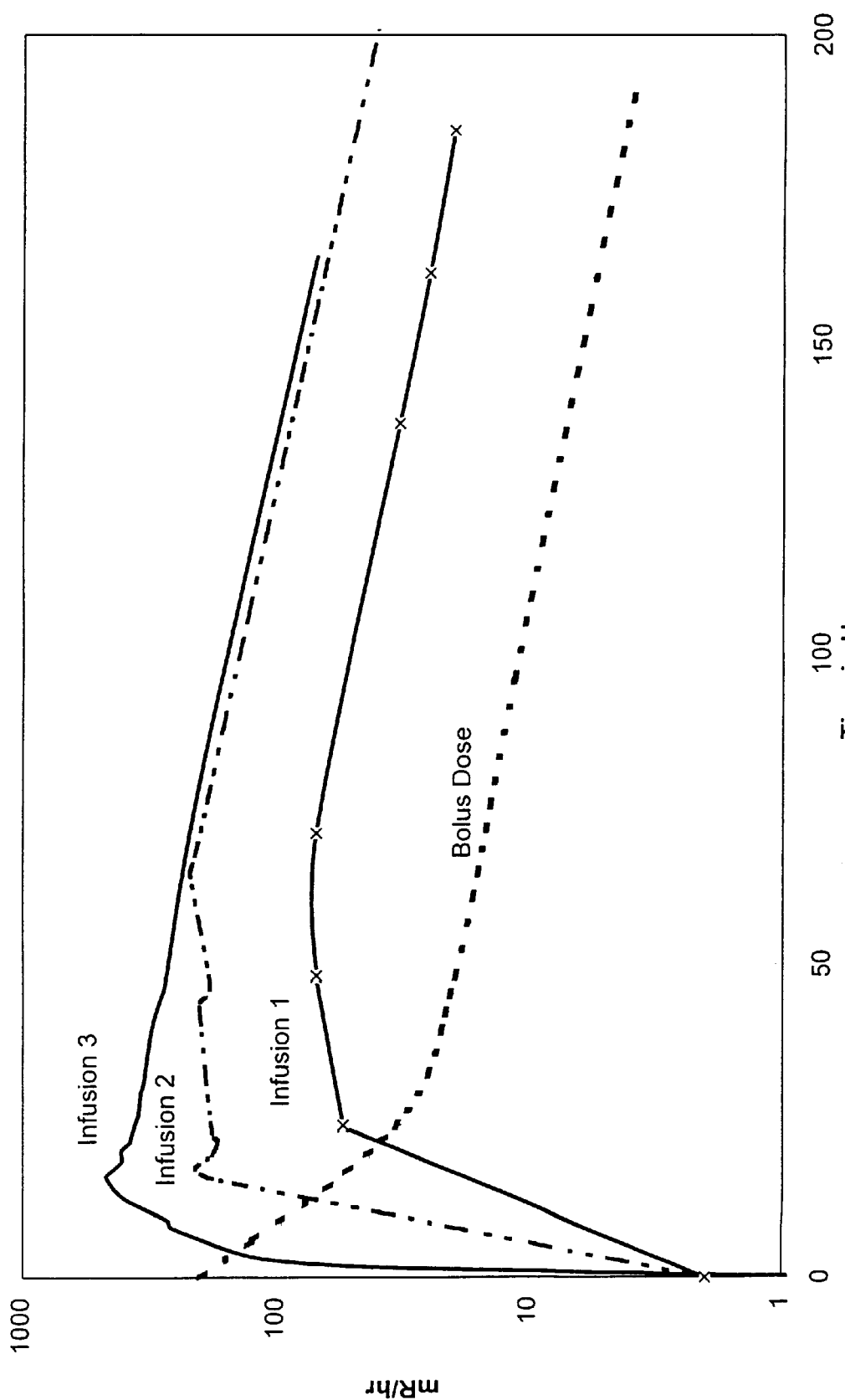
FIG. 2 illustrates the data of FIG. 1 plotted on a logarithmic scale.
Figure 3:
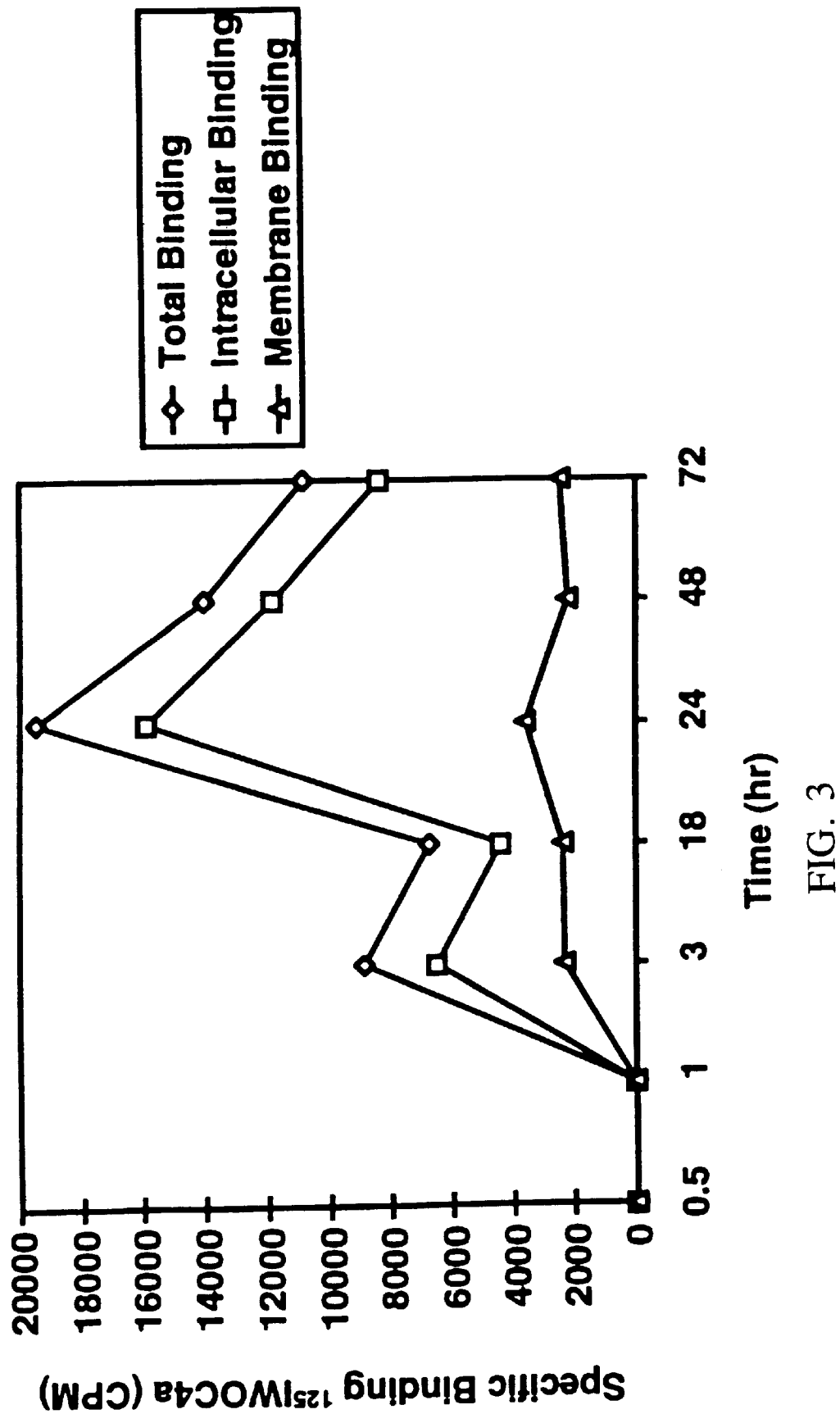
Figure 4:
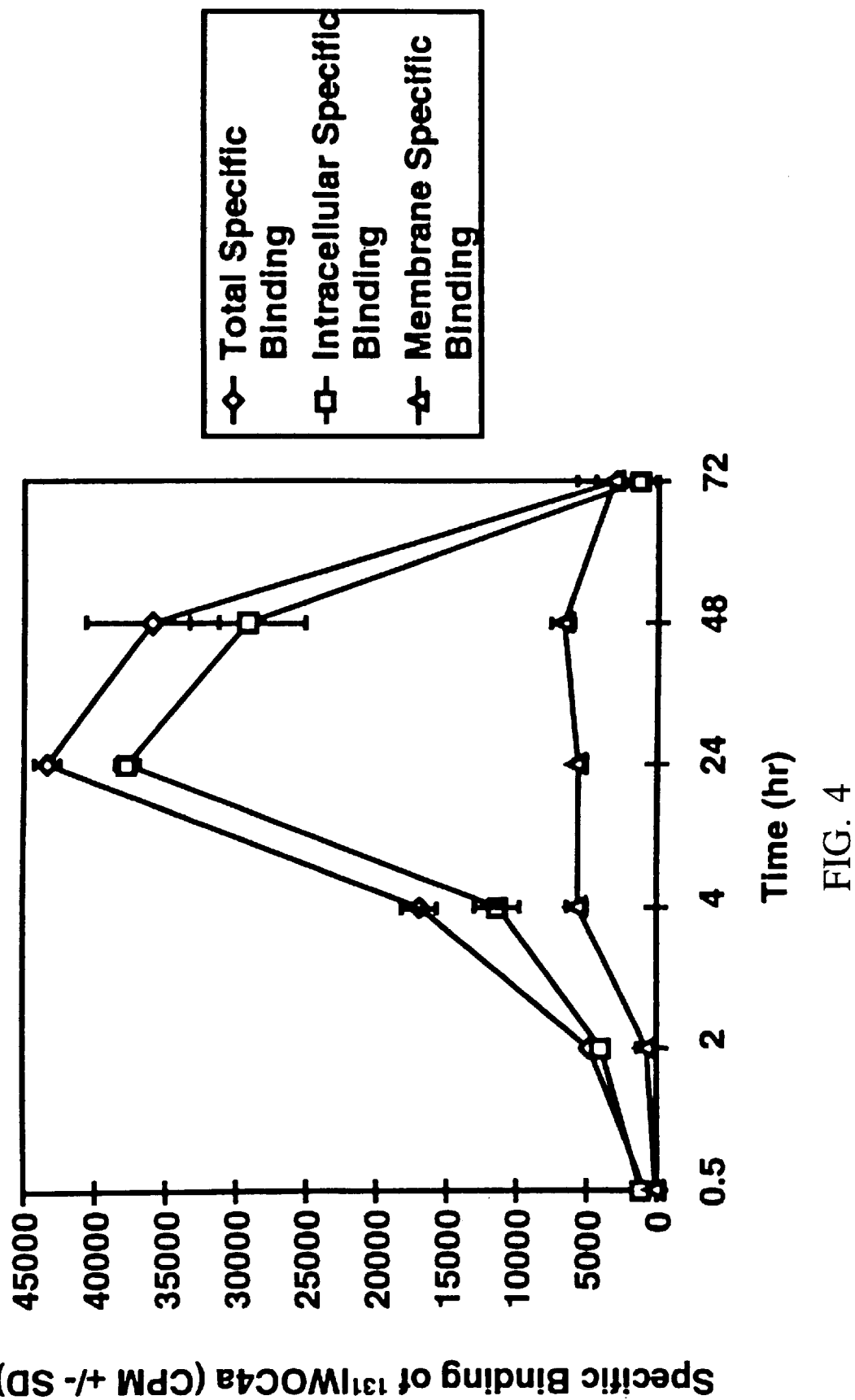
Figure 5:
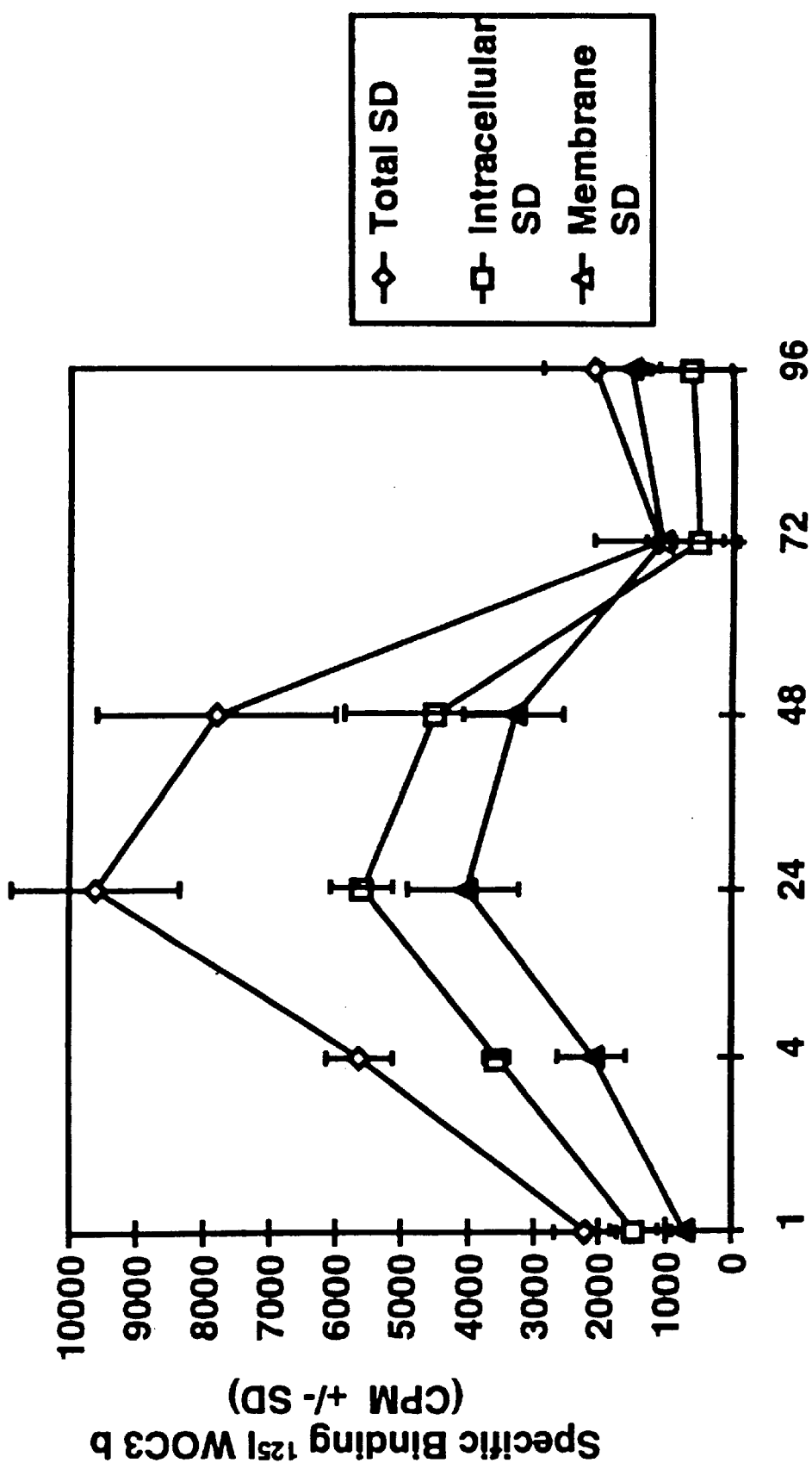
FIG. 5 illustrates the binding and internalization of $^{125}$I-WOC-3b.

By plotting the data on a semi-logarithmic scale, as shown in FIG. 2, and evaluating the total area under the curves, two important concepts are evident:

(1) Initial removal of peptide was far more substantial for bolus administration, leaving less peptide for cellular incorporation. The incorporation of radioligand by the cells was demonstrated by exponential decay, in which the half-life approached the physical half-life of the radioligand (67.3 hr). The slope of this decay line was remarkably consistent, regardless of dose sequencing.

(2) When normalized for the dose administered, the area under the curve (or residence time) increased up to five-fold simply by adjusting when and how the dose was administered. For the bolus injection, the area under the curve in FIG. 1 is 4,030 mR, corresponding to a ratio of 23 mR accumulated per mCi delivered. The comparable areas for the infusion experiments are 10,398 mR, 37,370 mR, and 41,993 mR. These data correspond to ratios of radioligand accumulated per mCi delivered of 66 mR/mCi, 96 mR/mCi, and 121 mR/mCi respectively. Thus the infusion ratios were 3, 4, and 5 fold higher than the bolus ratio. Infusion allowed more of the available radioligand to be incorporated into the tumor cell.

For Infusion Dose 3, this same patient was monitored with gamma camera scintigraphy. The photographs indicated not only an increase in uptake of the radiolabeled compound, but also more tumor foci could be identified. Additionally, the radioactivity remained in the tumor area for a longer period of time than was seen earlier in the bolus administration. In this patient, the tumor foci were still identifiable by gamma scintigraphy thirteen days after completion of the last infusion dose.

EXAMPLE 2

In vitro experiments using radiolabeled somatostatin analogs and human cell lines were performed to follow the uptake of a radiolabeled peptide over time in multiple cell types.

Cell Lines

The cells included: (1) IMR-32 (ATCC No. CCL-127), a human neuroblastoma cell line with a very high expression level of somatostatin receptors (SST), predominantly SST-2; (2) SKNSH (ATCC No. HTB-11), a human neuroblastoma bone marrow metastatic cell that lacks somatostatin receptors as defined by either a binding assay or reverse transcriptase-polymerase chain reaction (RTPCR); and (3) SK-R2, a SKNSH-derived cell line transfected with the gene for the SST-2 receptor. The IMR-32 and the SK-R2 cells express somatostatin receptors type 2 (SST-2). The SKNSH cells do not express somatostatin receptors and served as a negative control. Cell lines were obtained from the ATCC (IMR-32 and SKNSH) or from Ohio State University (Columbus, Ohio) (SK-R2). All cells lines were maintained in 5% $CO_2$ at 37° C. in media defined by the suppliers of the cell lines.

Peptide Binding and Internalization Assay

Cells were harvested, counted with a hemocytometer, and resuspended in binding buffer (Minimum Essential Medium (MEM), 10 mM Hepes, 0.01% BSA). A standard assay used 500,000 cells in 1 ml of binding buffer. Radioactive ligand alone (500,000 cpm), or in combination with at least 1,000-fold molar excess ($10^{-6}$ M) non-radioactive compound (to calculate specific binding), was added to a final volume of 1 ml. At the termination of the experiment, the incubation medium was removed, the cells were rinsed twice with Hanks balanced salt solution (HBSS), and the radioactivity in the cells determined using a gamma counter. This level of radioactivity represents total binding, which includes both membrane-bound and internalized fractions. Specific binding was determined by calculating the difference in the levels of measured radioactivity without the unlabeled competitor minus the radioactivity with the unlabeled competitor.

To differentiate between membrane and intracellular binding, cells were subsequently incubated for 10 min at 4° C. with acidified HBSS (pH=4–5), rinsed in HBSS, and the radioactivity again determined using the gamma counter. Since the acid wash preferentially released the radioactive ligand from the external surface of the cell, remaining radioactivity was attributed to internalized fractions. Membrane-associated binding was then calculated as the difference between the total binding and internalized fractions.

Ligand Binding and Internalization as a Function of Time

The times for ligand binding and internalization were analyzed using the standard assay methods described above. All radioactive ligands and competitors used were somatostatin analogs that preferentially bind to SST-2 cell receptors. The first series of experiments used IMR-32 cells that were exposed to a radioligand for varying periods of time (up to 72 hr). The incubation media was replaced at least every 48 hr. The radioligands included $^{125}$I-WOC-4a, $^{131}$I-WOC-4a, $^{125}$I-WOC-3b, and $^{111}$In-pentetreotide. The unlabeled competitor was octreotide acetate. WOC-4a and WOC-3b are multi-tyrosinated, SST-2-preferring somatostatin analogs that can be labeled to a high specific activity (8,800 Ci/mmol) and still retain high biologic activity and receptor binding affinity (Kd=1 nM). WOC-3b and WOC-4a have the same structures and synthesis as WOC-3B and WOC-4 described in U.S. Pat. No. 5,597,894.

The specific binding and internalization data for $^{125}$I-WOC-4a, $^{131}$I-WOC-4a, $^{125}$I-WOC-3b, and $^{111}$In-pentetreotide radiolabeled compounds are presented in FIGS. 3, 4, 5, and 6, respectively. The data indicate that the binding of somatostatin analogs to their cellular receptors increased over time with maximal binding occurring at 48–72 hours. Significant fractions of total radioactivity (40–75%) were incorporated into the cell.

EXAMPLE 3

Determination of Rate of Loss of Radioactivity

Figure 7:
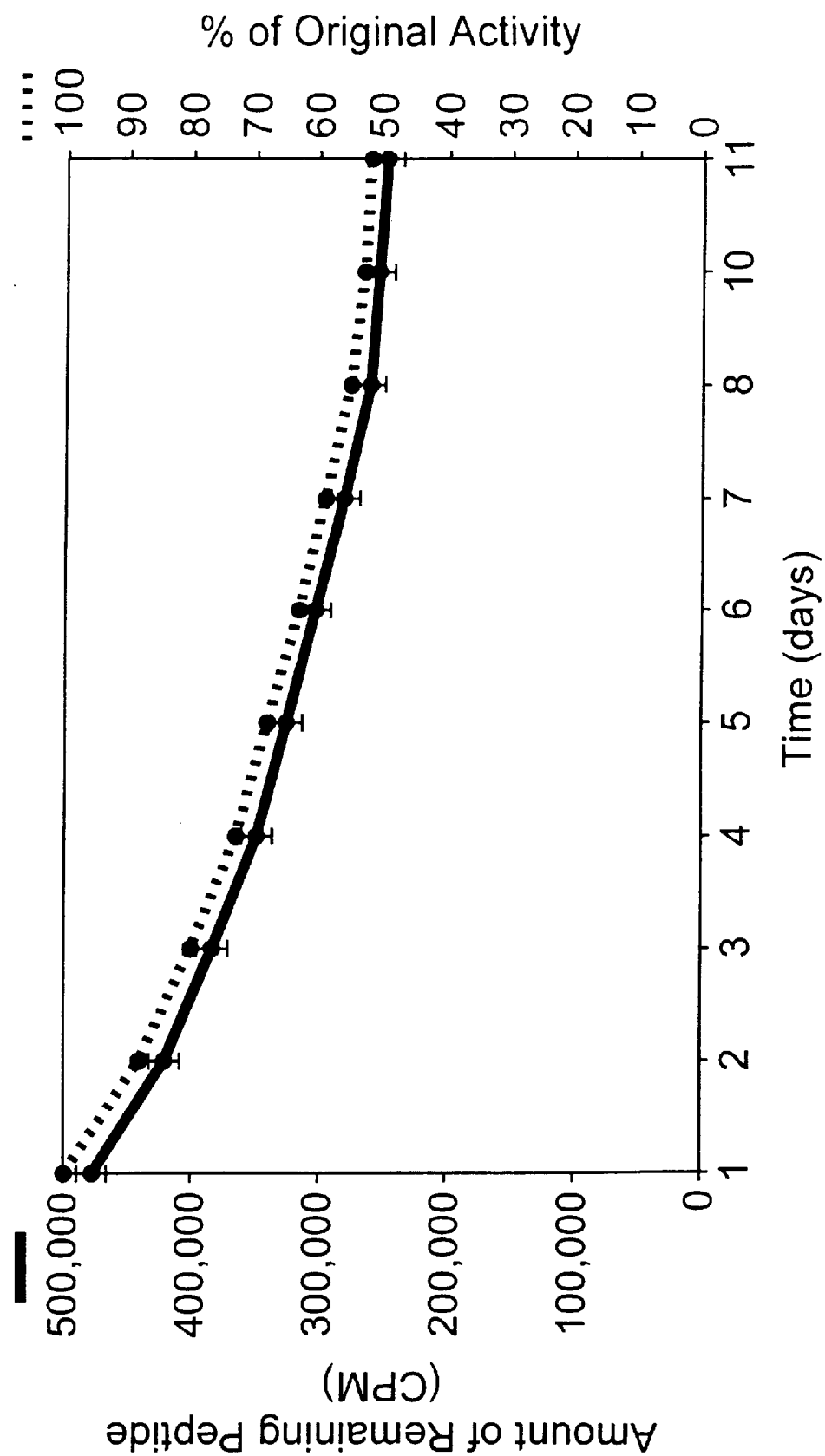

Cell lines and assay techniques were as described in Example 2. IMR-32 cells were incubated for 48 hr in $^{125}$I-WOC-4a (1 CPM/cell) and washed three times in HBSS. Cells were counted to determine baseline radioactivity. Cells were maintained in MEM with 10% fetal bovine serum (FBS), and the media was replaced daily. Radioactivity of the replaced media was counted, and the percent loss of radioactivity from the cells was calculated over time. These results are shown in FIG. 7, which shows that the retention time of $^{125}$I-WOC-4a was about 11 days. This result is highly surprising since the described biologic half-life of somatostatin is measured in minutes, and all known somatostatin analog half-lives are measured in hours (octreotide acetate, 90–120 min; lanreotide, 60–90 min).

This experiment demonstrated that once a radiolabeled compound is internalized into the cell, its retention time and thus its ability to deliver radiation to the cell are markedly extended. The internalized peptide is protected from degradation, and the physical half-life of the isotope becomes the critical determinant of radiation dose. Because the measured loss of radioactivity included any loss due to cell death and subsequent loss of membrane integrity, the actual retention time of the radioligand inside an intact cell might be somewhat longer than the measured 11 days.

The results of Examples 2 and 3 provided three important observations that support the use of this method in radioimaging and radiotherapy: (a) a substantial proportion of the receptor and its associated radioligand were sequestered within the cell; (b) progressive receptor-mediated internalization occurred over an extended period of time (at least 48 hr); and (c) internalization increased the retention time substantially.

EXAMPLE 4

Binding to Cells With and Without Somatostatin Receptors

To determine that the radioligand in fact bound to the SST-2 receptor, experiments were conducted with cell lines IMR-32, SK-R2, and SKNSH. $^{111}$In-pentetreotide (1 CPM/cell) was used as the radioligand and octreotide acetate as a competitor. The assay methods were as described in Example 2. The data are presented in Table 5.

TABLE 5

$^{111}$In-Pentetreotide Binding to Cells with and Without Somatostatin Receptors

| | TOTAL | INTRACELLULAR | MEMBRANE |
|---|---|---|---|
| IMR-32 | | | |
| Total Binding (CPM ± SD) | 4,780 ± 928 | 2,408 ± 511 | 2,373 ± 417 |
| Specific Binding (CPM) | 3,908 | 1,536 | 2,372 |
| Kd = 4 × 10$^{-9}$M | | | |
| SKR-2 | | | |
| Total Binding (CPM ± SD) | 36,261 ± 2,085 | 2,607 ± 672 | 33,655 ± 2,728 |
| Specific Binding (CPM) | 35,475 | 1,792 | 33,683 |
| Kd = 1 × 10$^{-9}$M | | | |
| SKNSH | | | |
| Total Binding (CPM ± SD) | 861 ± 30 | 775 ± 107 | 87 ± 114 |
| Specific Binding (CPM) | 0 | 0 | 0 |

As seen in Table 5, no specific binding was detected with the SKNSH cells, which lack somatostatin receptors. However, in the IMR-32 cells, significant levels of specific binding were observed on the cell membrane and inside the cells. Specific membrane binding was also observed in the SK-R2 cells (genetically engineered to overproduce the SST-2 membrane receptor). In the SK-R2 cell line, 95% of binding was associated with the plasma membrane, and relatively less internalization of ligand occurred. Scatchard plot analysis revealed an apparent dissociation constant (a measure of the affinity of the binding between the ligand and the receptor) of $1\times10^{-9}$ M to $4\times10^{-9}$ M for the SK-R2 and IMR-32 cells respectively, which is in the range expected for these receptor-ligand interactions.

This experiment demonstrated that (a) the binding of somatostatin analogs to their receptors and subsequent internalization is specific for cells expressing the somatostatin receptor; and (b) internalization requires other cellular components (probably signal transduction elements not seen in the genetically engineered cells), and is not an intrinsic function of the membrane receptor alone.

EXAMPLE 5

Pulse-Chase Studies

Figure 8:
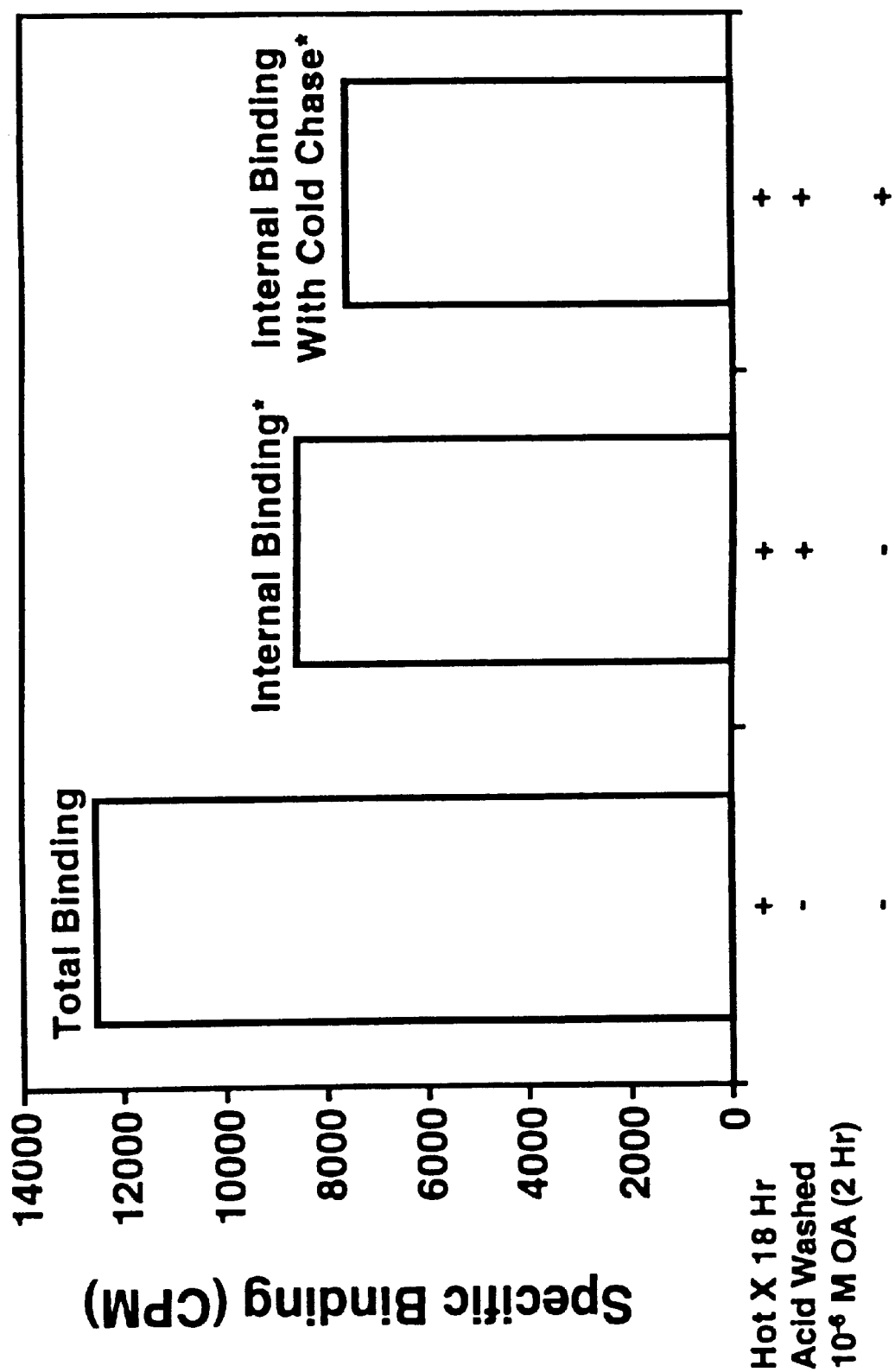
FIG. 8 illustrates the effect of a competitor on internalized $^{111}$In-pentetreotide.

To ascertain the role of competition after internalization, IMR-32 cells were incubated with a radioligand for a time sufficient for internalization to occur, and were then incubated with unlabeled radioligand. The IMR-32 cells were incubated overnight with $^{111}$In-pentetreotide to load the cells with radioactive ligand as described in Example 2. One set of culture tubes was subsequently acid-washed and then incubated for 2 hours with an excess of unlabeled octreotide acetate (a cold chase). The levels of radioactivity were then compared to those for tubes that did not undergo the cold chase. As indicated in FIG. 8, the levels of radioactivity remaining in the cells were similar for both the control and the cold-chase tubes, indicating that once internalized the radioligand was not competed by a unlabeled compound. These observations have significant implications for the use of somatostatin analogs as radiotherapy: intracellular radioactive ligand can not be competed out by an unlabeled competitor, and thus will be retained in the cell.

EXAMPLE 6

Nuclear Translocation Experiments

To determine the intracellular movement of the labeled somatostatin analogs, IMR-32 cells were incubated in T-150 cell culture flasks containing Minimum Essential Medium with L-glutamine and non-essential amino acids for varying periods of time with the radioligands $^{125}$I-WOC-4a, $^{125}$-somatostatin, and $^{111}$In-pentetreotide. The cells were washed twice in media at 4° C. and resuspended in cold isotonic sucrose. The labeled cells were passed through a ball-bearing homogenizer three times to disrupt cell membranes while leaving approximately 95% of the cell nuclei intact, according to the method of Balch et al., Arch. Biochem. Biophys., vol. 240, p. 413 (1985). The cell homogenate was mixed with Percoll to give a final concentration of 0.292% Percoll and spun at 20,400 rpm in a Beckman 40.2 rotor for 45 min to generate a density gradient. Density marker beads (Pharmacia) were used to indicate density levels in the tube. The contents of the tube were fractionated in an ISCO Density Gradient Fractionator. The resulting tubes were assayed for content of radiolabeled somatostatin or analogs, DNA to indicate nuclei, protein, the plasma membrane marker 5'-nucleotidase, and the lysosome marker N-acetylglucosaminidase. The usual assumption was made that the radioactivity measured in fractions rich in a certain cell component was in fact associated with that component; e.g., the radioactivity measured in a fraction rich in plasma membrane was due to association of the radiolabeled compound with the plasma membrane.

Figure 9A:
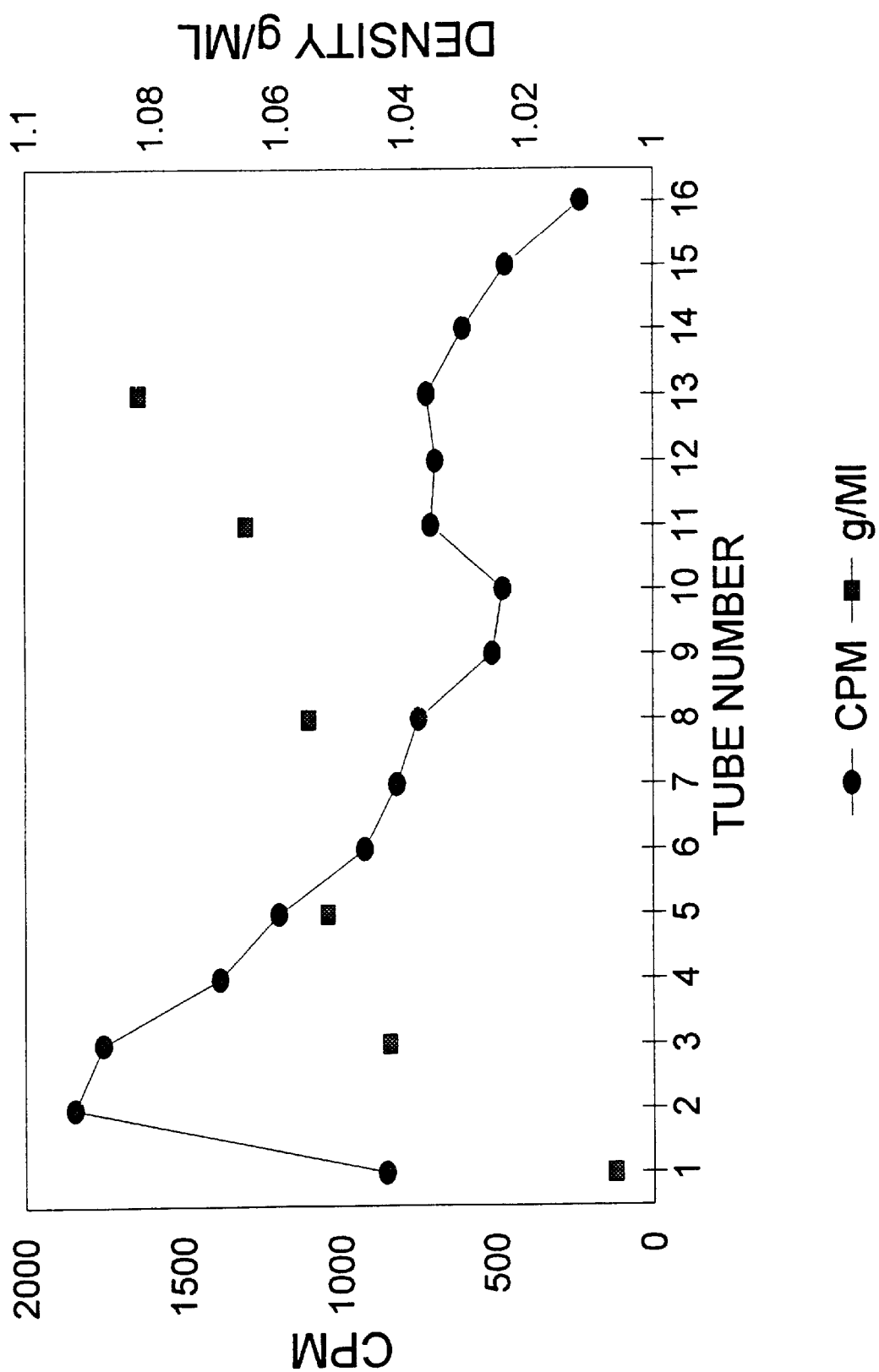
FIG. 9A illustrates the degree of internalization and translocation of $^{125}$I-WOC-4a at 1 hr.
Figure 9B:
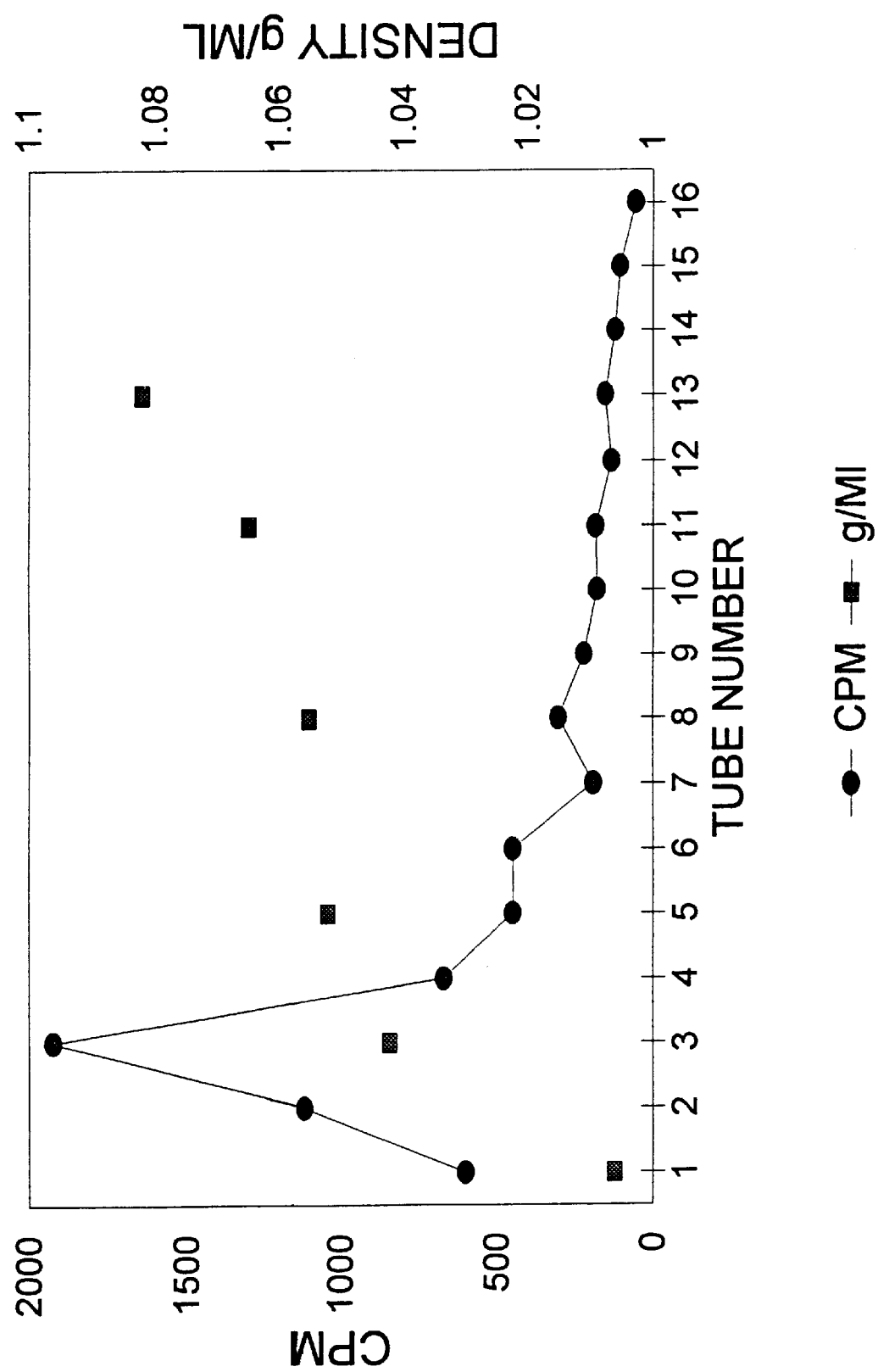
FIG. 9B illustrates the degree of internalization and translocation of $^{125}$I-WOC-4a at 4 hr.
Figure 9C:
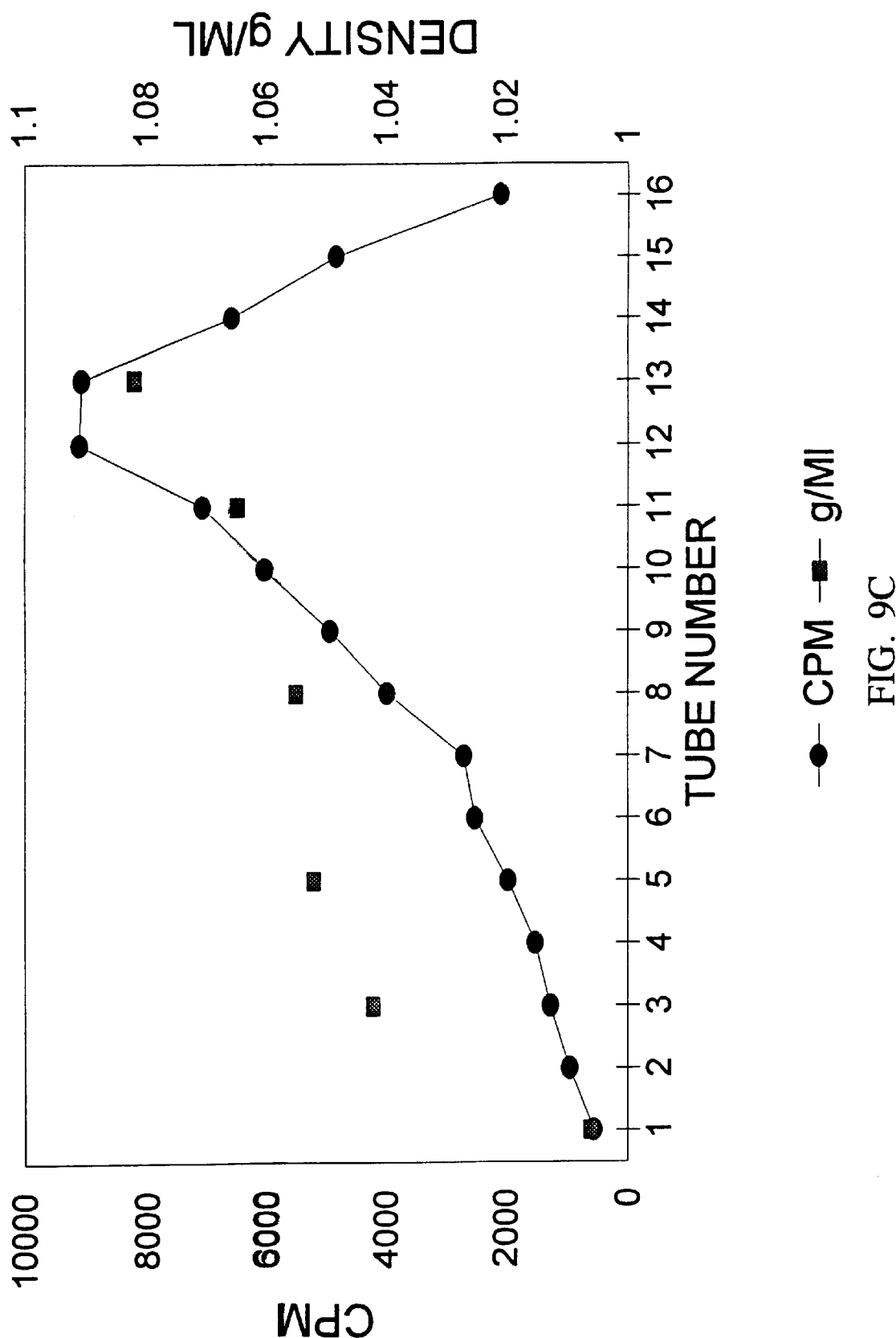
FIG. 9C illustrates the degree of internalization and translocation of $^{125}$I-WOC-4a at 24 hr.
Figure 10A:
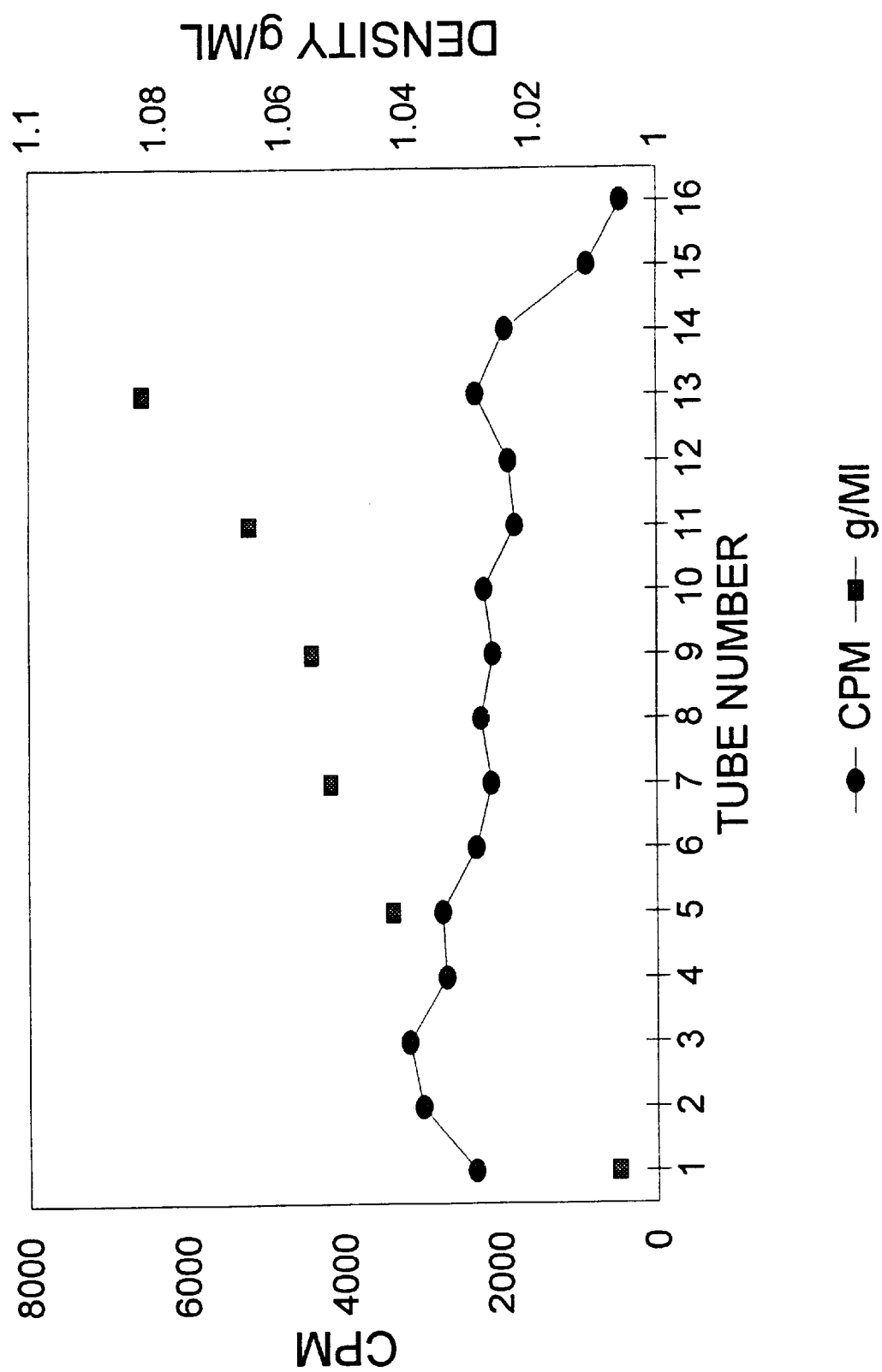
FIG. 10A illustrates the degree of internalization and translocation of $^{125}$I-somatostatin at 1 hr.
Figure 10B:
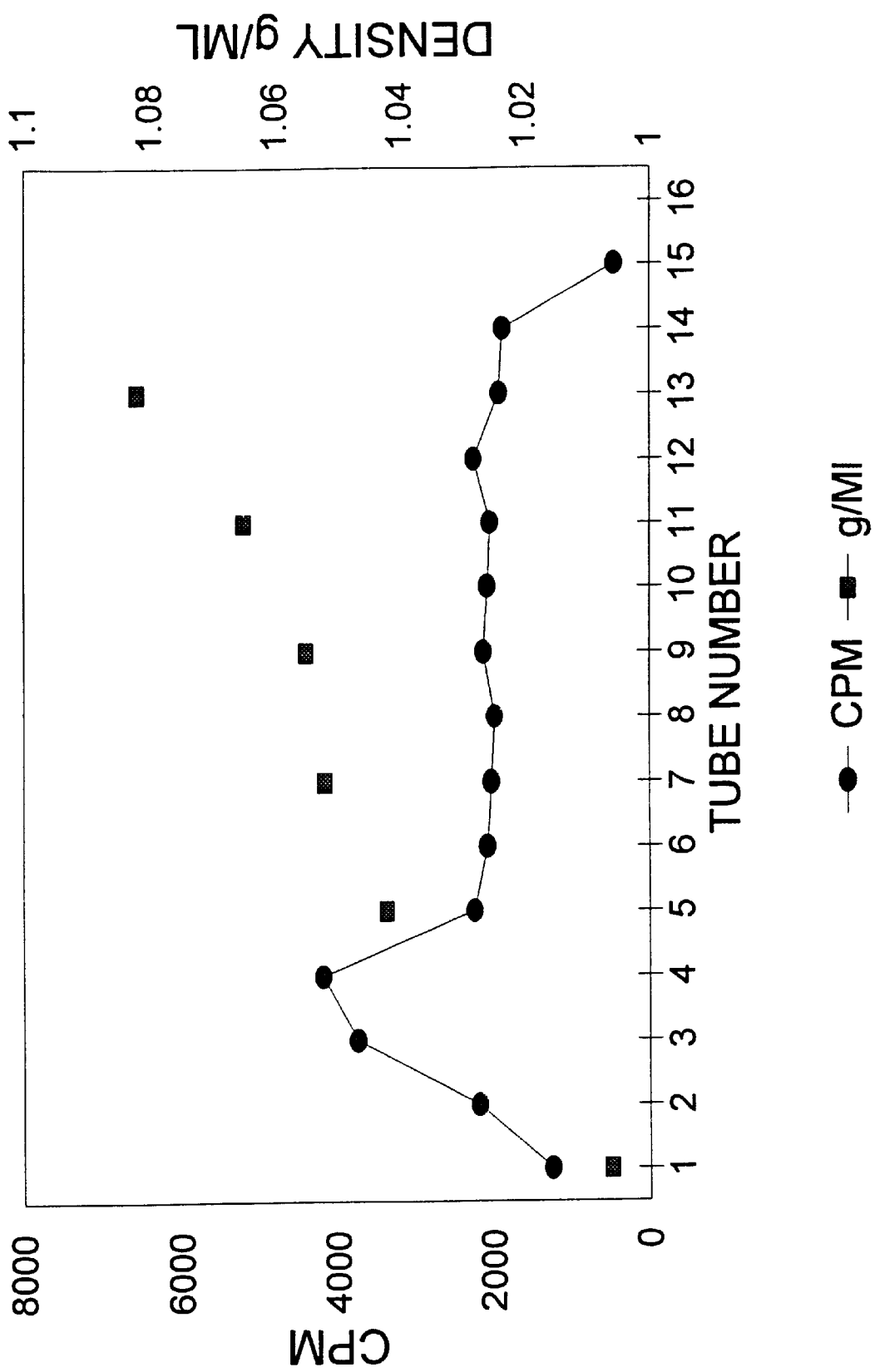
FIG. 10B illustrates the degree of internalization and translocation of $^{125}$I-somatostatin at 4 hr.
Figure 10C:
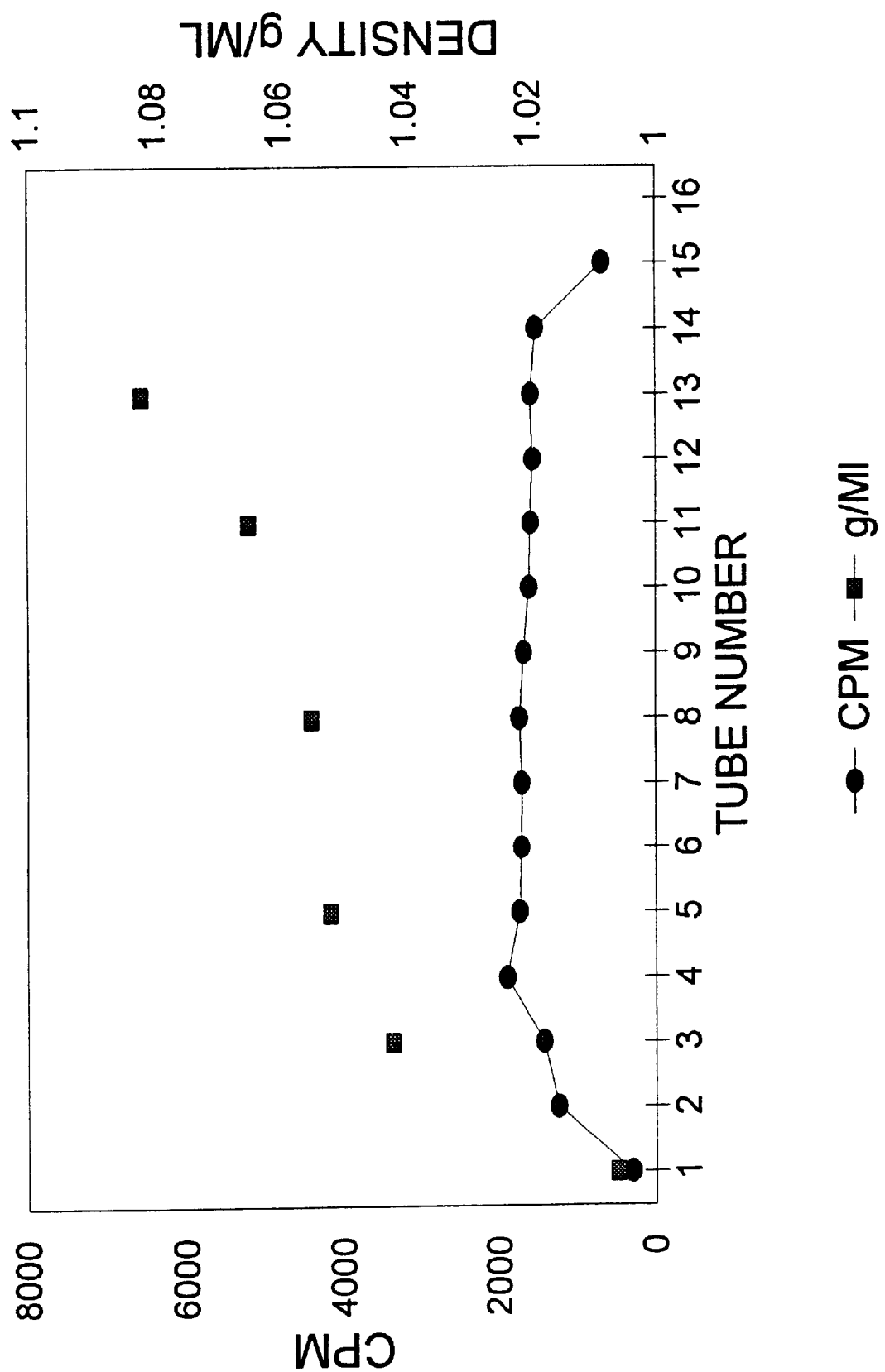
FIG. 10C illustrates the degree of internalization and translocation of $^{125}$I-somatostatin at 24 hr.
Figure 11A:
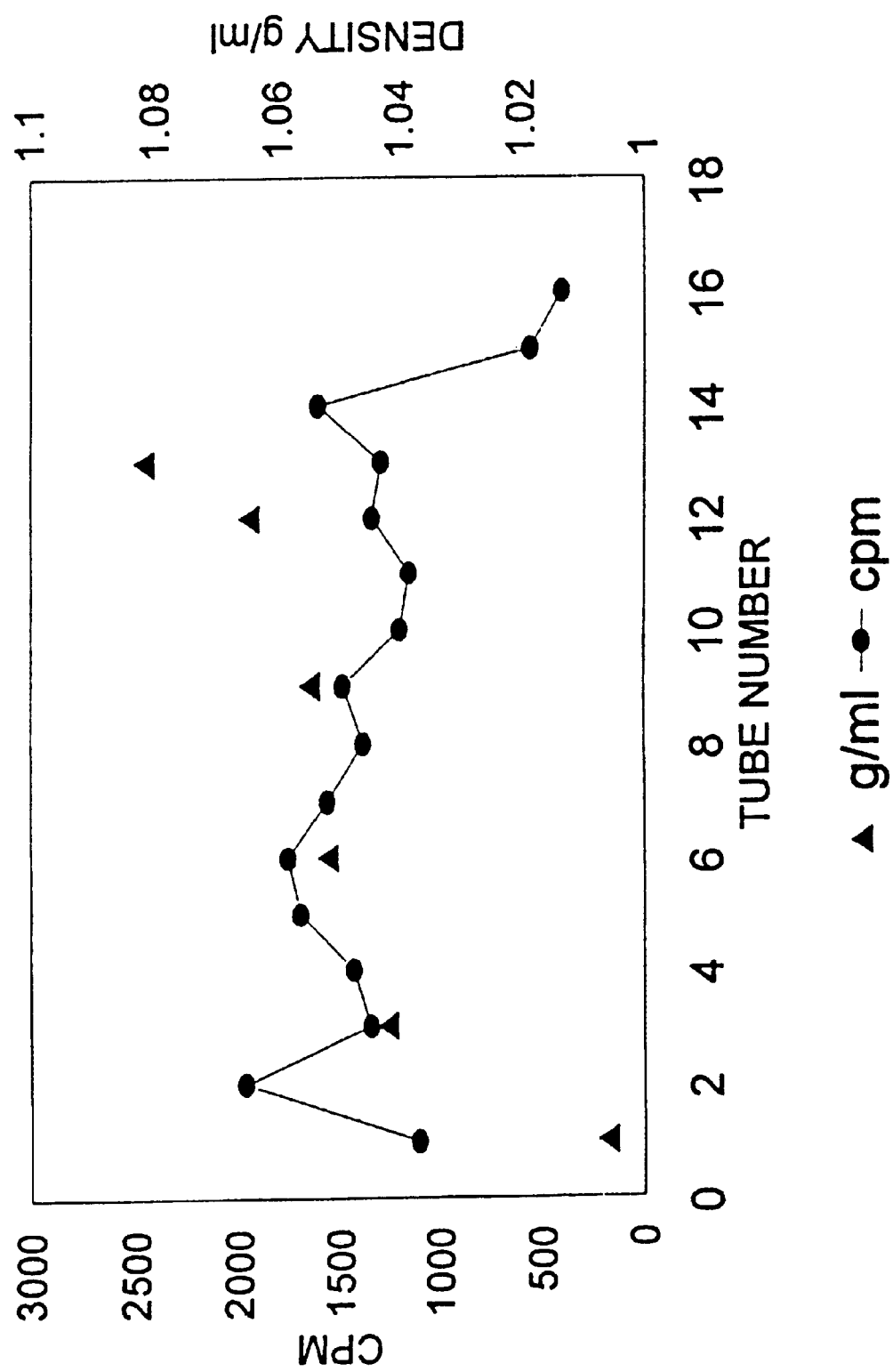
FIG. 11A illustrates the rate of internalization and translocation of $^{111}$In-pentetreotide at 1 hr.
Figure 11B:
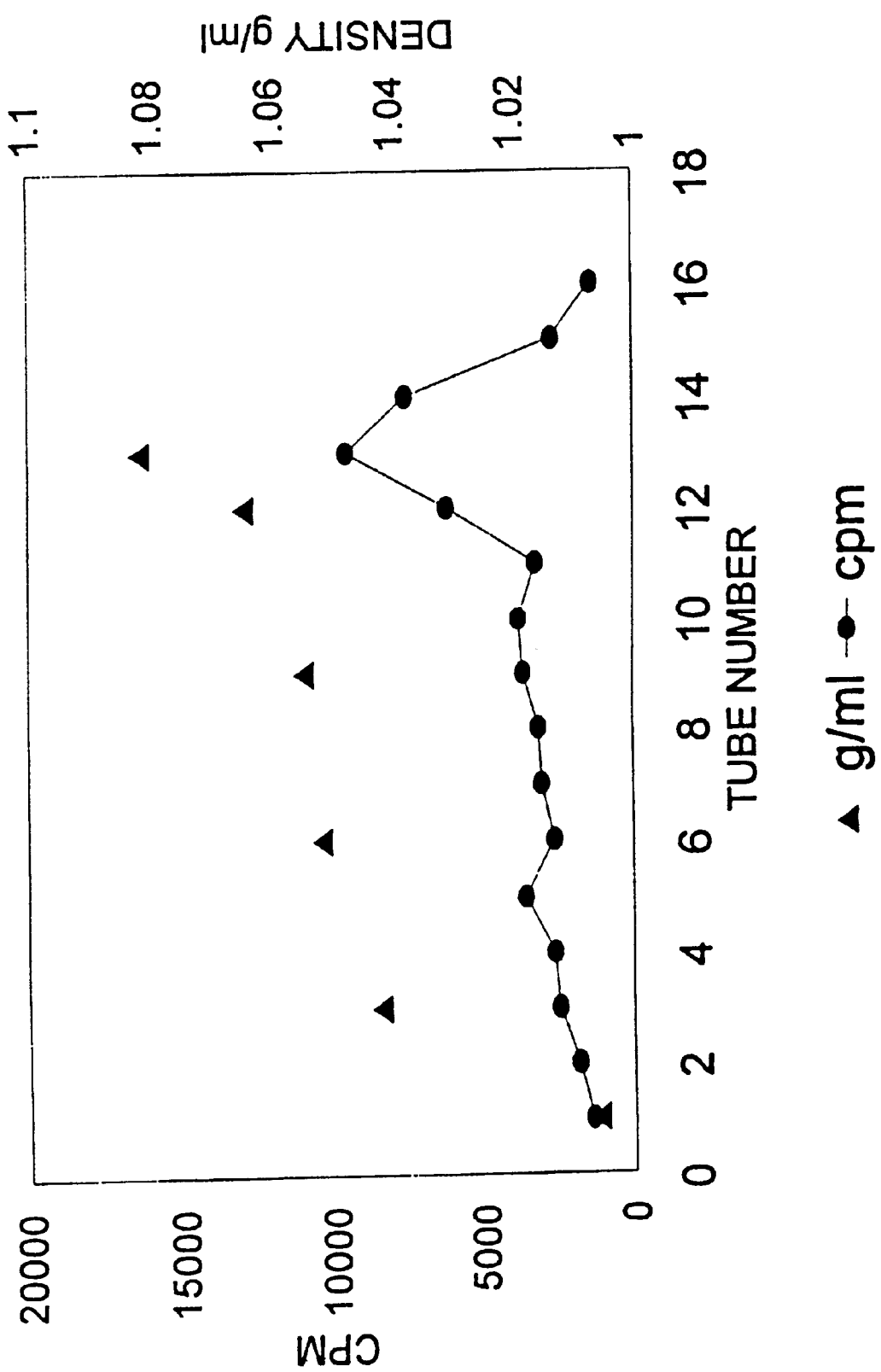
FIG. 11B illustrates the rate of internalization and translocation of $^{111}$In-pentetreotide at 4 hr.
Figure 11C:
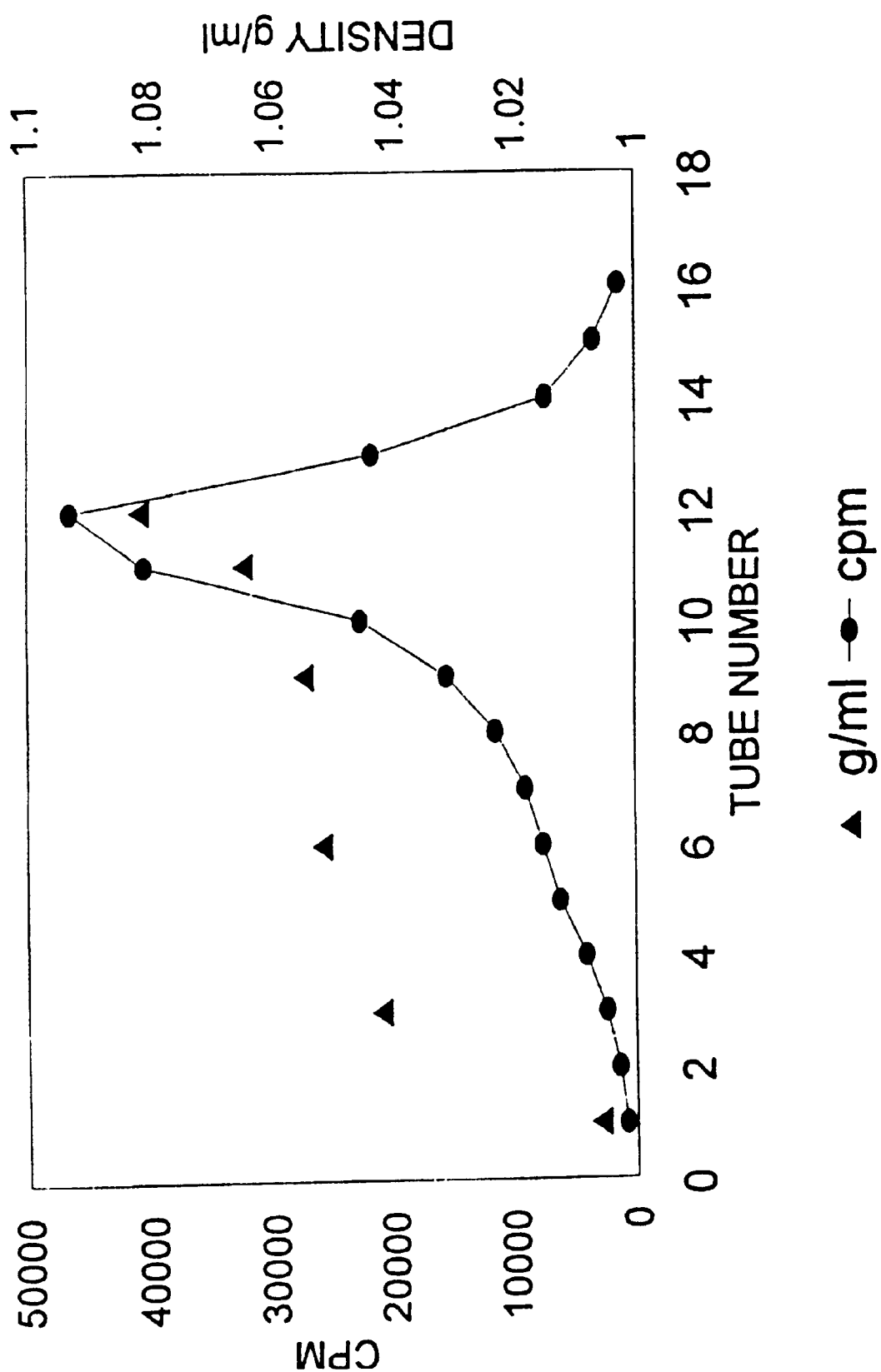
FIG. 11C illustrates the rate of internalization and translocation of $^{111}$In-pentetreotide at 24 hr.

The data are presented in FIGS. 9A–C, 10A–C, and 11A–C. The density distribution is represented by the triangles in the figures. Nuclear fractions were found in the density gradient represented by Tubes 12–15, and membrane fractions by Tubes 0–6. FIG. 9 demonstrates that early cellular distribution of $^{125}$I-WOC-4a was principally on the plasma membrane (Tubes 1–5). FIG. 9A shows that very little nuclear activity was seen at 1 hr. By 4 hr, FIG. 9B, membrane binding was still indicated, but the nuclear fraction began to show an increase in activity. At 24 hr, FIG. 9C, almost all activity was seen in the nuclear fractions, indicating that the $^{125}$I-WOC-4a had been translocated to the nucleus. Thus, the data indicated that several hours were required for this radiolabeled compound to bind to membrane receptors, for those receptors to be internalized into the cell, and for the radioligand to be translocated to the nucleus. Radiodecaying nuclei will then ionize DNA, resulting in cellular damage. FIGS. 11A (1 hr data), 11B (4 hr data), and 11C (24 hr data) indicate that the timing for internalization and translocation for $^{111}$In-pentetreotide was similar to that of $^{125}$I-WOC-4a.

FIG. 10, however, indicates that timing for the movement of native $^{125}$I-somatostatin was different. As early as 1 hr, FIG. 10A, there was both membrane binding and small amounts of nuclear binding. By 4 hr, FIG. 10B, the plasma membrane binding appeared to have peaked and the nuclear fraction was dissipating. By 24 hr, FIG. 10C, this very short-lived radiolabeled peptide (biologic half-life of 1 to 2 min) was completely gone from the cultured cells, and essentially no plasma membrane or nuclear binding was seen.

The time for a radiolabeled compound to become internalized is a function of the cell-receptor type, the particular compound, and the particular radioisotope.

EXAMPLE 7

Binding of Somatostatin to Nuclear DNA

To demonstrate that somatostatin or an analog binds to genetic material, DNA was extracted from cells that had been incubated with the radioligand $^{111}$In-pentetreotide, and analyzed for radioactivity.

Figure 12:
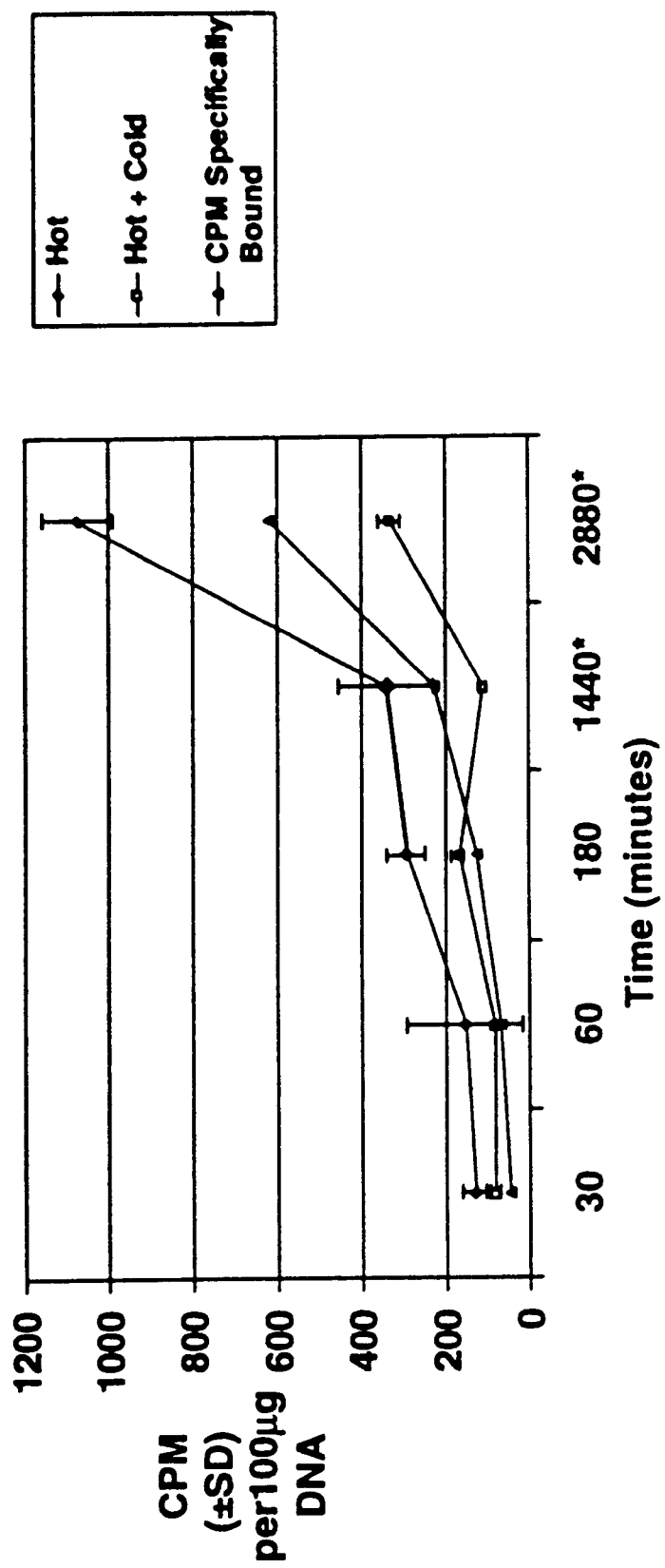
FIG. 12 illustrates the rate of binding of $^{111}$In-pentetreotide to DNA from IMR-32 cells.

Triplicate T-75 flasks containing IMR-32 and SKNSH cells which had been incubated overnight with $^{111}$In-pentetreotide as in Example 2 were used for DNA extraction. Cells were removed from the culture surface using a sterile rubber policeman. The suspended cells were washed three times in cold Dulbecco's phosphate buffered saline and processed through a DNA extraction procedure according to the vendor's directions (GenomicPrep® cells and Tissue DNA Isolation Kit, Pharmacia Biotech, Piscataway, N.J.). The cells were incubated in the Cell Lysis Solution of the DNA isolation kit at 37° C. for 10 minutes. Next, 3 µl of the Rnase Solution was added to the cell lysate, followed by thorough mixing and incubation at 37° C. for 1 hour. The samples were cooled to room temperature, and 200 µl of the Protein Precipitation Solution were added. Following vortexing, the contents of each tube were centrifuged at 14,000×g for 1 min, and the DNA pellet was washed with 70% ethanol. Following drying the DNA was hydrated in a DNA Hydration Solution, and the concentration of DNA determined by spectrometry at 260 nm. One hundred microgram (100 µg) quantities of each treatment were transferred to radioactive counting vials, and the amount of radioactivity associated with each was measured in a Beckman 5500 gamma counter. The data, as presented in Table 6, were obtained as counts per minute (cpm). The differences between radioactivity measured in cells incubated solely with radioligand and in cells incubated with both radioligand and unlabeled ligand were statistically analyzed using ANOVA. The rate of accumulation of $^{111}$In-pentetreotide on DNA of IMR-32 cells is shown in FIG. 12.

TABLE 6

Incorporation of $^{111}$In-pentetreotide ± Octreotide Acetate into
The DNA of SST-2-Positive or SST-2-Negative Cells

| | IMR - 32 Cells (SST-2 positive) | | | | | | | |
|---|---|---|---|---|---|---|---|---|
| | Non-Decay Corrected | | | Decay Corrected Values | | | | |
| Time (mins.) | Radioligand (CPM ± SD) | Radioligand + Unlabeled Ligand (CPM ± SD) | CPM Specifically Bound (Difference) | Radioligand (CPM ± SD) | Radioligand + Unlabeled Ligand (CPM ± SD) | SPM Specifically Bound (Difference) | % Specifically Bound | p[1] |
| 30 | 128 ± 28 | 83 ± 12 | 45 | 128 ± 28 | 83 ± 12 | 45 | 35 | 0.06 |
| 60 | 152 ± 165 | 83 ± 1 | 69 | 157 ± 165 | 83 ± 1 | 69 | 45 | 0.002 |

TABLE 6-continued

Incorporation of $^{111}$In-pentetreotide ± Octreotide Acetate into
The DNA of SST-2-Positive or SST-2-Negative Cells

| 180  | 291 ± 44  | 165 ± 15 | 126 | 291 ± 44  | 165 ± 15 | 126 | 43 | 0.009  |
|------|-----------|----------|-----|-----------|----------|-----|-----|--------|
| 1440 | 264 ± 104 | 87 ± 6   | 177 | 338 ± 133 | 112 ± 8  | 226 | 67 | 0.04   |
| 2880 | 624 ± 59  | 203 ± 20 | 421 | 1023 ± 97 | 332 ± 33 | 690 | 67 | 0.0001 |

SKNSH Cells (SST-2 negative) Non-Decay Corrected

| Time (minutes) | Radioligand (CPM ± SD) | Radioligand + Unlabeled Ligand (CPM ± SD) | CPM Specifically Bound (Difference) | % Specifically Bound | p[1] |
|---|---|---|---|---|---|
| 60   | 85 ± 8  | 91 ± 25 | -6  | 0  | NS |
| 1440 | 87 ± 1  | 80 ± 2  | +7  | 8  | NS |
| 4320 | 232 ± 10 | 174 ± 41 | +58 | 25 | NS |

[1]Differences between CPM of radioligand by itself and radioligand plus unlabeled ligand as determined by ANOVA.
NS = not significant.

Figure 13:
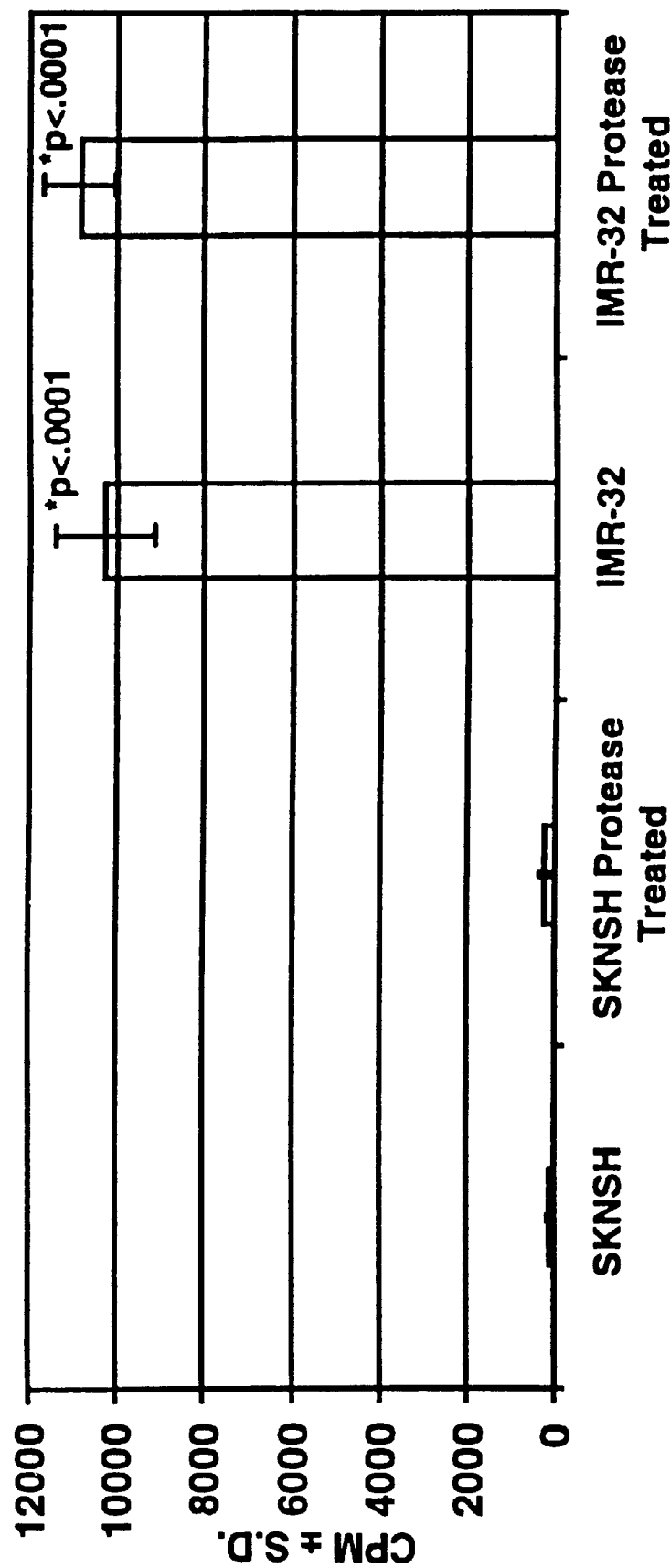
FIG. 13 illustrates the effect of a protease on the binding of $^{111}$In-pentetreotide to DNA from IMR-32 and SKNSH cells.

Additionally, the DNA from each flask was divided in half, and 1 mg of DNA from each flask was treated with proteinase-K (Lite Technologies, Gaithersburg, Md.) for 1 hour at 37° C. The enzyme-treated DNA was then reprecipitated with ethanol and sodium acetate, washed with cold ethanol, and redissolved in DNA hydration solution. The concentration was determined by spectrophotometry at 260 nm. One hundred microgram (100 μg) of protease-treated DNA and an equal quantity of untreated DNA were transferred to radioactive counting vials and the amount of radioactivity measured in a Beckman 5500 gamma counter, as described above. The data, as presented in Table 7 and FIG. 13, were obtained as counts per minute (cpm).

TABLE 7

$^{111}$In-Pentetreotide Binding to Cellular DNA[1]

|  | IMR-32 CELLS | | SKNSH CELLS | |
|---|---|---|---|---|
| Experiment | Protease Treated (CPM) | Untreated (CPM) | Protease Treated (CPM) | Untreated (CPM) |
| 1 | 10,276 | 11,512 | 122 | 316 |
| 2 | 9,564 | 10,122 | 412 | 319 |
| 3 | 12,648 | 14,566 | 208 | 220 |
| Mean + S.D. | 10,829 ± 1614 | 12,066 ± 2273 | 247 ± 149 | 285 ± 56 |

[1]Numbers represent the counts per minute (CPM) for 100 μg samples of DNA for each cell type in three replicate experiments.

As shown by Tables 6 and 7, a substantial amount of $^{111}$In-pentetreotide associated with the cellular DNA of IMR-32 cells, whereas virtually none bound to the DNA of the SKNSH cells. As discussed above in Example 4, the SKNSH cells do not have somatostatin receptors type 2, and did not internalize the radiolabeled somatostatin analogs.

Surprisingly, the $^{111}$In-pentetreotide bound to the DNA of IMR-32 cells was resistant to the effects of the nonspecific proteinase-K. Overall, the protease treatment removed only 10–13% of total bound CPM, showing that the association of the radioligand with DNA was not due to binding to nonspecific proteins such as histones.

The kinetics of radioligand binding to the DNA was comparable to that seen for the intracellular movement in IMR-32. Thus, the rate of intracellular transduction of the radioligand was roughly equal to the rate of DNA binding.

EXAMPLE 8

Cytotoxicity of $^{125}$I-WOC-4a

WOC-4a was synthesized by solid-phase synthesis techniques as described previously in Example 2 and U.S. Pat. No. 5,597,894. IMR-32 human neuroblastoma cells (ATCC #CCL-127, American Type Culture Collection, Rockville, Md.), which have been previously shown to express SST-2 receptors, and PANC-1 human pancreatic epithelial carcinoma cells (ATCC #CRL-1469), which are SST-2-negative, were maintained in culture at 37° C. in humidified air with 5% $CO_2$. IMR-32 cells were cultured in Eagle's Minimum Essential Medium (MEM) with Earle's salts (Gibco, Grand Island, N.Y.) and supplemented with non-essential amino acids, 15% fetal bovine serum (Gibco, Grand Island, N.Y.), and an antibiotic-antimycotic agent (Gibco, Grand Island, N.Y.). PANC-1 cells were cultured in Dulbecco's modified Eagle's medium (Gibco, Grand Island, N.Y.), which was supplemented with 10% fetal calf serum and an antibiotic-antimycotic solution. Both cell lines were passaged once a week using 0.25% trypsin and 1 mM EDTA.

For short-term cytotoxicity experiments, cells were harvested, washed, and seeded in 96-well cell culture clusters (Costar, Cambridge, Mass.) at a density of 5×10$^3$ cells/well. In the short-term, dose-ranging experiments, cells were incubated in binding buffer (MEM, 10 mM HEPES, 0.01% BSA). $^{125}$I-WOC-4a was added to the appropriate wells in concentrations ranging from 0.1–100 CPM/cell. After exposure, the radioactive medium was replaced with culture medium and the cells were maintained for an additional five days. Viability was analyzed by a 3-(4,5-dimethylthiazole-2-yl)-2,5-diphenyltetrazolium bromide (MTT) enzymatic cell viability assay as described in R. F. Hussain et al., "A New Approach for Measurement of Cytotoxicity Using Colorimetric Assay," Journal of Immunological Methods, vol. 160, p. 89 (1993). Colorimetric results were then analyzed using a microplate reader (Dynatech MR 500, Dynatech Labs, Chantilly, Va.). Results were expressed in optical density (OD).

In the long-term exposure experiments, seven T75 flasks (Corning, Cambridge, Mass.) were seeded with 25 million IMR-32 cells. The cells were incubated for 48 hr at 37° C. in a 5% $CO_2$/95% air humidified atmosphere and exposed to one of the following: control media (binding buffer); 1 CPM/cell $^{125}$I-WOC-4a; 1 CPM/cell $^{125}$I-WOC-4a with 10$^{-6}$ M octreotide acetate (Novartis Pharmaceuticals, East Hanover, N.J.); 1 CPM/cell $^{125}$I alone; 1 CPM/cell $^{125}$I with $10^{-6}$ M octreotide acetate; or $10^{-6}$ M octreotide acetate alone. Cells were then harvested, washed three times with fresh culture medium, and cryopreserved for 4 weeks at $-85°$ C. in 1 ml of 90% culture medium and 10% DMSO (Sigma, St. Louis, Mo.). After cryopreservation, cells were rapidly thawed, and viability was assessed with trypan blue exclusion (n=3/group). The remainder of the cells were replated in 96-well plates (n=21/group) (Costar, Cambridge, Mass.) and grown under standard conditions for 24 hr. Viability of these cells was then confirmed by MTT assay.

Following short-term drug exposure, the effect of each dose of $^{125}$I-WOC-4a on viability of IMR-32 and PANC-1 cells was determined. Mean cell viability (±SD) was calculated and the dose effect analyzed by analysis of variance (ANOVA). Student's t-tests were used when viability was compared for a single drug concentration between the two cell types. In the long-term exposure group, mean cell viability (±SD) was calculated for each treatment group and compared to those of the control group by ANOVA ($p<0.05$).

Figure 14:
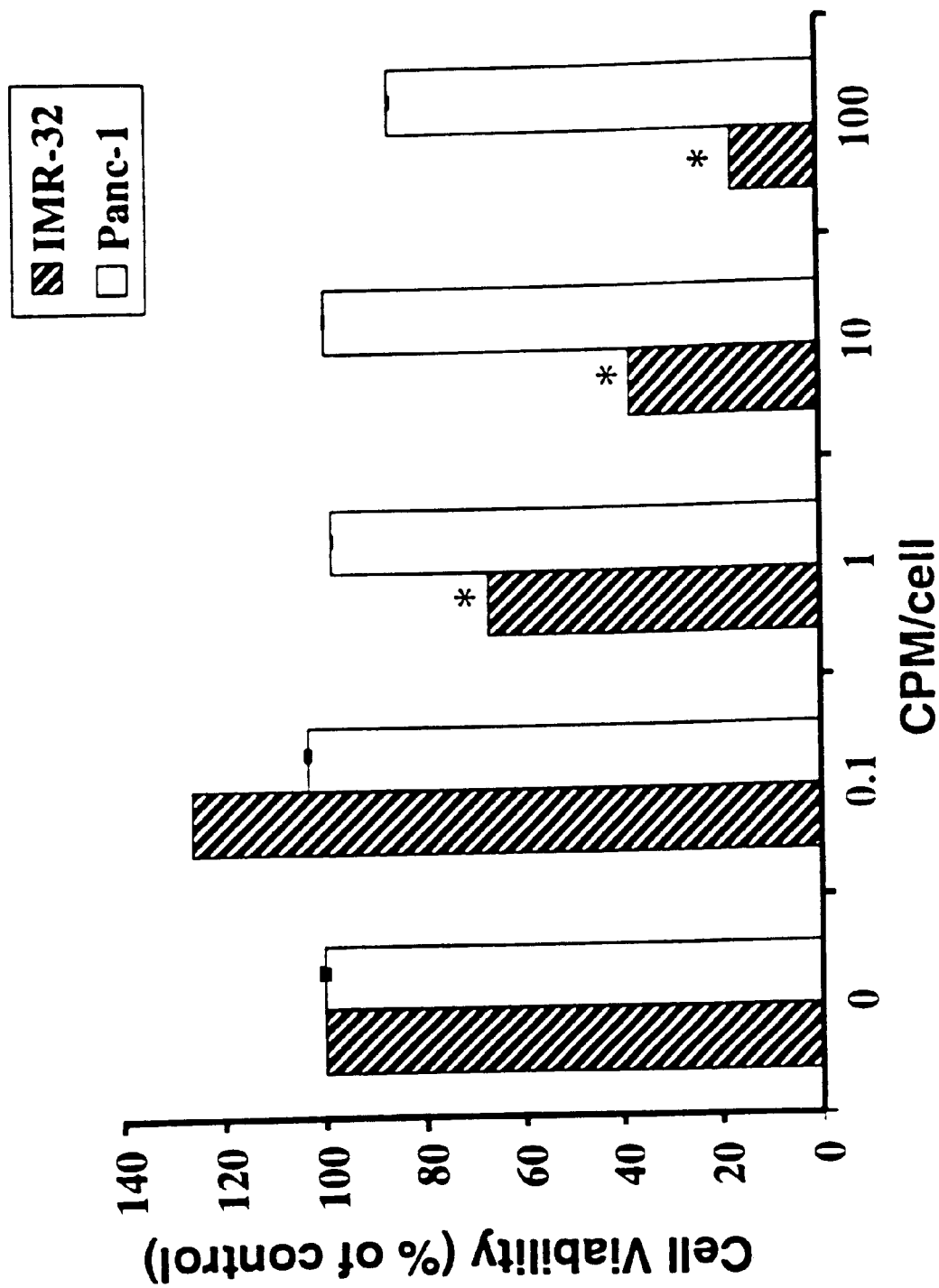
FIG. 14 illustrates the effect of various concentrations of $^{125}$I-WOC-4a on the viability of IMR-32 cells.

When IMR-32 cells were incubated for 48 hr with $^{125}$I-WOC-4a at doses ranging from 0.1–100 CPM/cell, there was a dose-dependent decrease in cell viability, as measured by the MTT assay. $^{125}$I-WOC-4a induced a 33% decrease in cell viability at a dose of 1 CPM/cell and an 87% decrease in cell viability at a dose of 100 CPM/cell (FIG. 14). These differences were statistically different by ANOVA ($p<0.05$). However, when the SST-2 negative cell line (PANC-1) was exposed to the same concentrations of $^{125}$I-WOC-4a, no statistically significant difference in cell viability between control and any treatment group (n=21 per group) was found as shown in FIG. 14. These results indicate that following a short-term (48hr) exposure, $^{125}$I-WOC-4a induces SST-2-dependent cytotoxicity.

Figure 15:
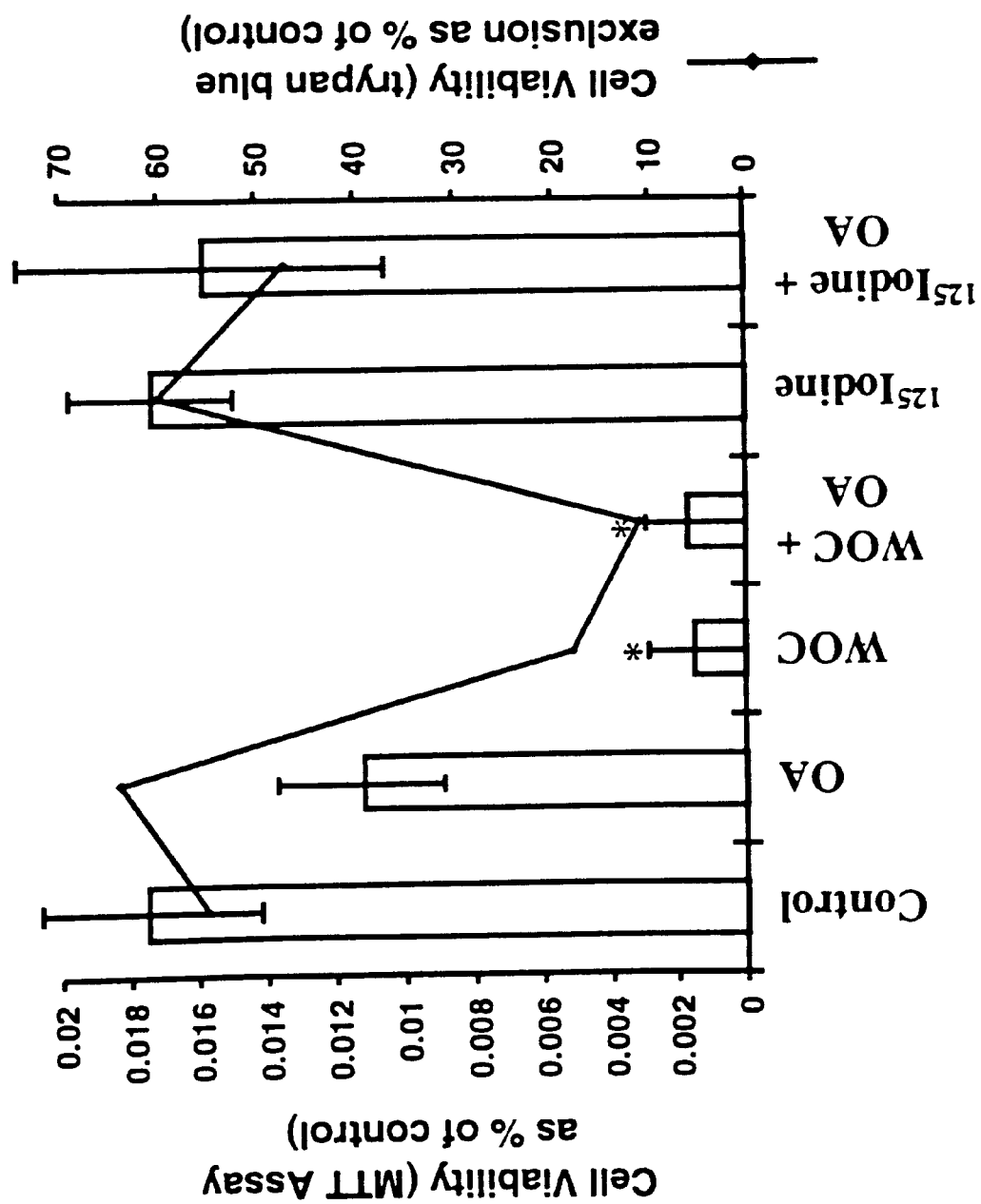
FIG. 15 illustrates the long-term effect of $^{125}$I-WOC-4a on IMR-32 cell viability.

For evaluating the effect of a long-term (4-week) exposure to $^{125}$I-WOC-4a on SST-2 expressing cells, IMR-32 cells were exposed to either 1 CPM/cell $^{125}$I-WOC-4a, 1 CPM/cell $^{125}$I-WOC-4a with $10^6$ M octreotide acetate, $10^6$ M octreotide acetate alone, $^{125}$I alone, or $^{125}$I with octreotide acetate. Cell viability of each treatment group was compared to control values after a four-week, cryopreserved exposure. These data are shown in FIG. 15. $^{125}$I-WOC-4a induced statistically significant cytotoxicity; however, no cytotoxicity was seen following exposure to similar doses of $^{125}$I alone or $^{125}$I with octreotide acetate. In addition, $^{125}$I-WOC-4a cytotoxicity was not inhibited by the addition of a 10,000-fold excess of octreotide acetate, implying that intracellular incorporation of small amounts of $^{125}$I-WOC-4a may be cytotoxic to SST-2-positive cells. This cryopreserved technique allows a long-term exposure to the radioligand but prevents cell proliferation that might mask the radioligand's cytotoxic effects.

These studies demonstrated that $^{125}$I-WOC-4a induced cytotoxicity in neuroblastoma cells that express SST-2 receptors. This implies that $^{125}$I-WOC-4a will be a potential therapeutic agent for SST-2-containing tumors.

EXAMPLE 9

Cellular Uptake of Steroid Hormone

To follow the time of uptake of a steroid hormone, three cell lines were incubated with a radiolabeled estrogen using procedures similar to those of Example 2. Three breast cancer cell lines were used; MCF-7 (ATCC No. HTB-22), T-47D (ATCC No. HTB-133), and ZR-75-1 (ATCC No. CRL-1500). The estrogen used was 17-β-estradiol, the major secreted estrogen in humans. The radiolabeled compound was $^{125}$I-17-β-estradiol, which was either purchased from New England Nuclear or synthesized by the following procedure: A 10 ml Sephadex G-10 column was equilibrated for 1 hr with 0.1 M PBS. A solution was prepared of 12.5 μg estradiol conjugate (BL-43), 25 μl methanol, 50 μl 0.05 M phosphate buffer pH 7.5, 3 mCi Na$^{125}$I, and 25 μl of a mixture of 10 mg chloramine-T and 10 ml 0.05 M phosphate buffer. After mixing for 40 sec, 25 μl of sodium metabisulfite 20 mg/10 ml 0.05 M Phosphate buffer was added and mixed an additional 40 sec. The mixture was then added to the Sephadex column and eluted first with 0.1 M PBS. Finally, the radiolabeled estradiol was eluted with 0.1 M PBS and 1,4 Dioxane (70:30).

The standard binding procedure described in Example 2 was used except that radiolabeled estradiol was used as the ligand with 1000× excess non-radioactive estradiol as the competitor. Unlike peptides that initially must bind on the plasma membrane, steroids bind only to intracellular receptors. Thus no radioactivity on the membrane should be found. Table 8 displays the data from this experiment.

TABLE 8

Specific Binding of 125 I-17-B-estradiol with Time

| Cell Line | 1 Hr (CPM) | 4 Hr (CPM) | 24 Hr (CPM) | 48 Hr (CPM) |
|---|---|---|---|---|
| T-47D | 401 | 506 | 532 | 455 |
| ZR-75-1 | 4102 | 4865 | 3370 | 3057 |
| MCF-7 | 1605 | 2253 | 4109 | 731 |

Figure 16A:
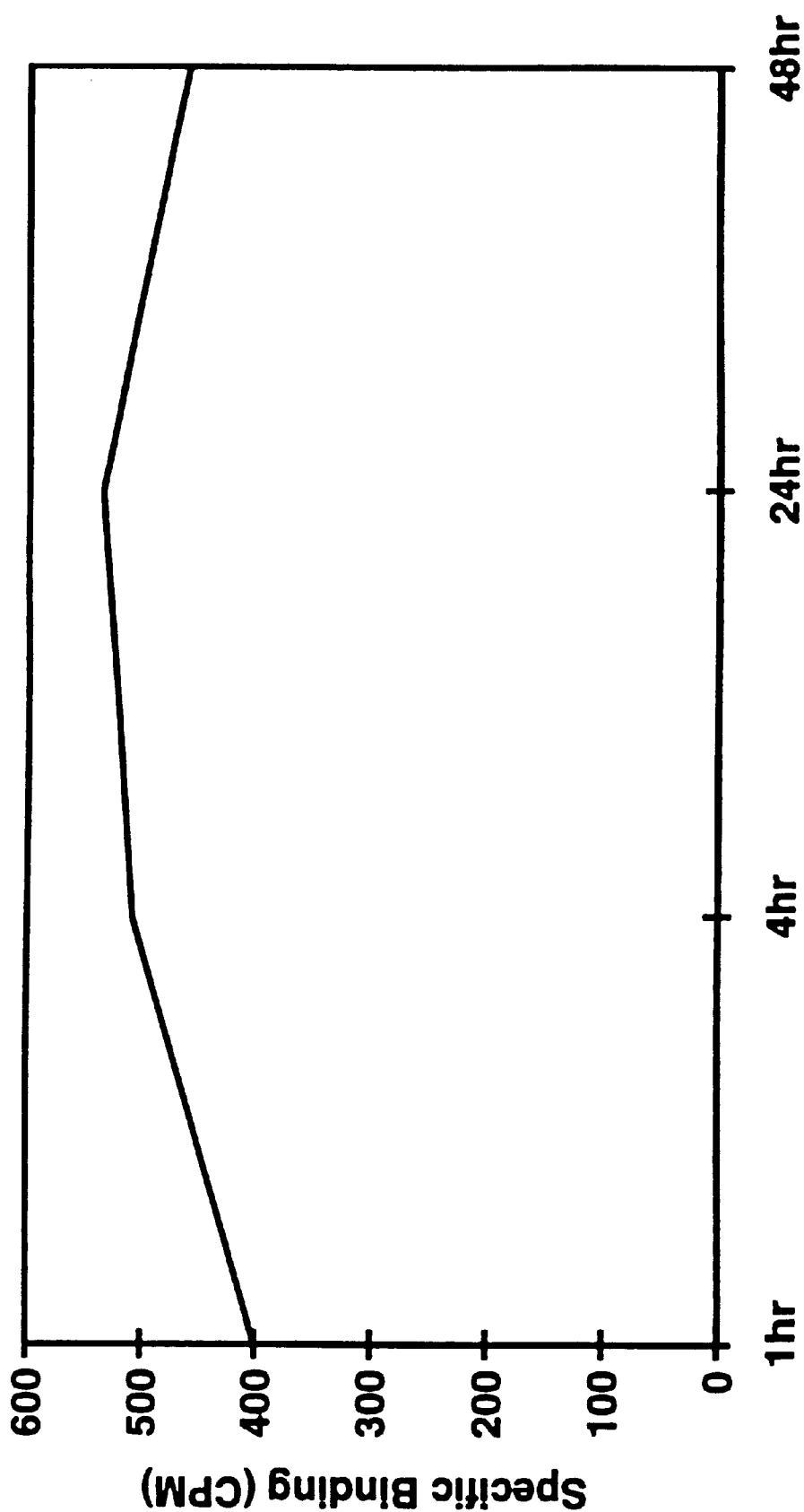
FIG. 16A illustrates the rate of binding of $^{125}$I-17-β-estradiol to the T-47-D cell line.
Figure 16B:
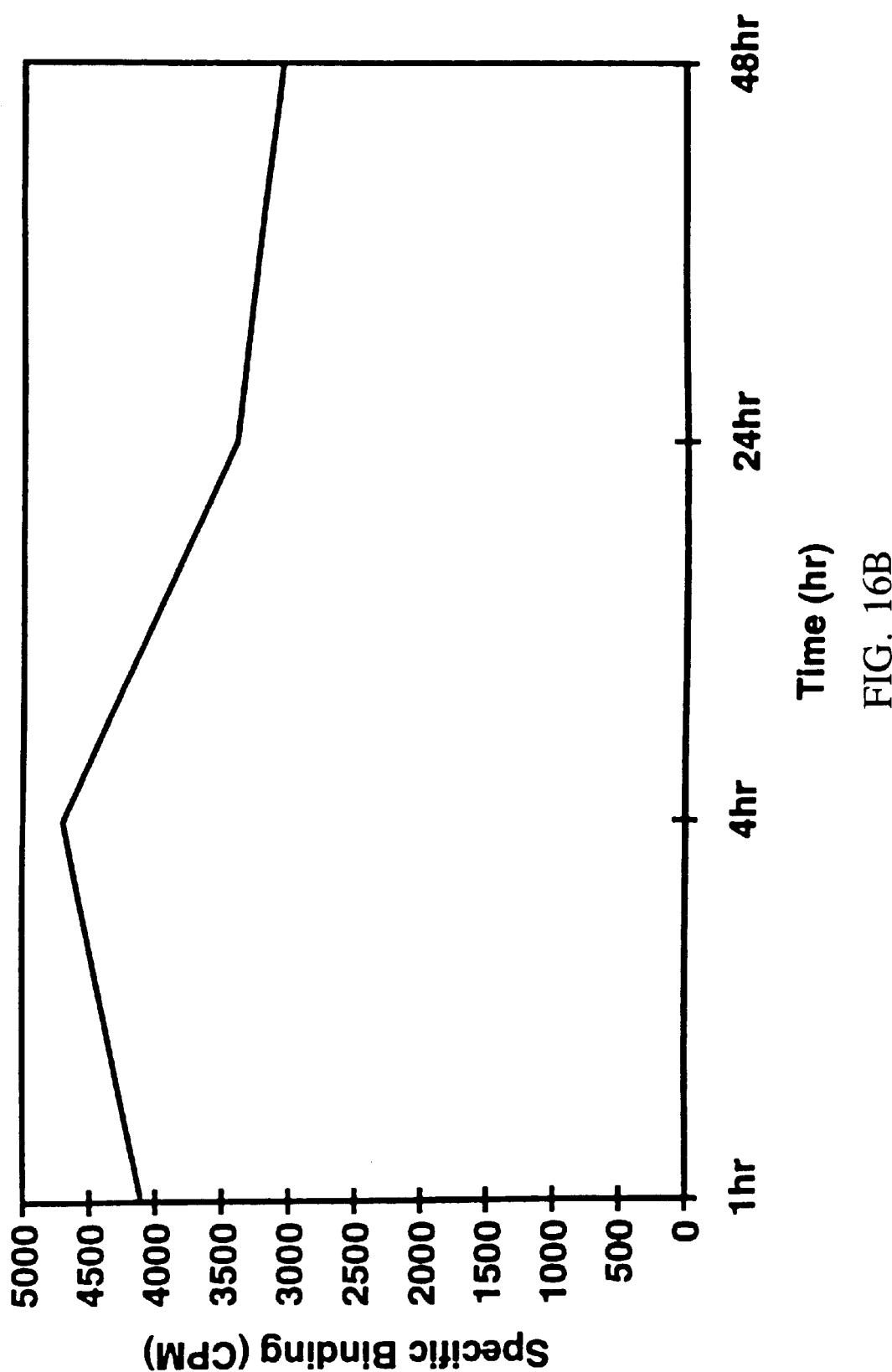
FIG. 16B illustrates the rate of binding of $^{125}$I-17-β-estradiol to the MCF-7 cell line.
Figure 16C:
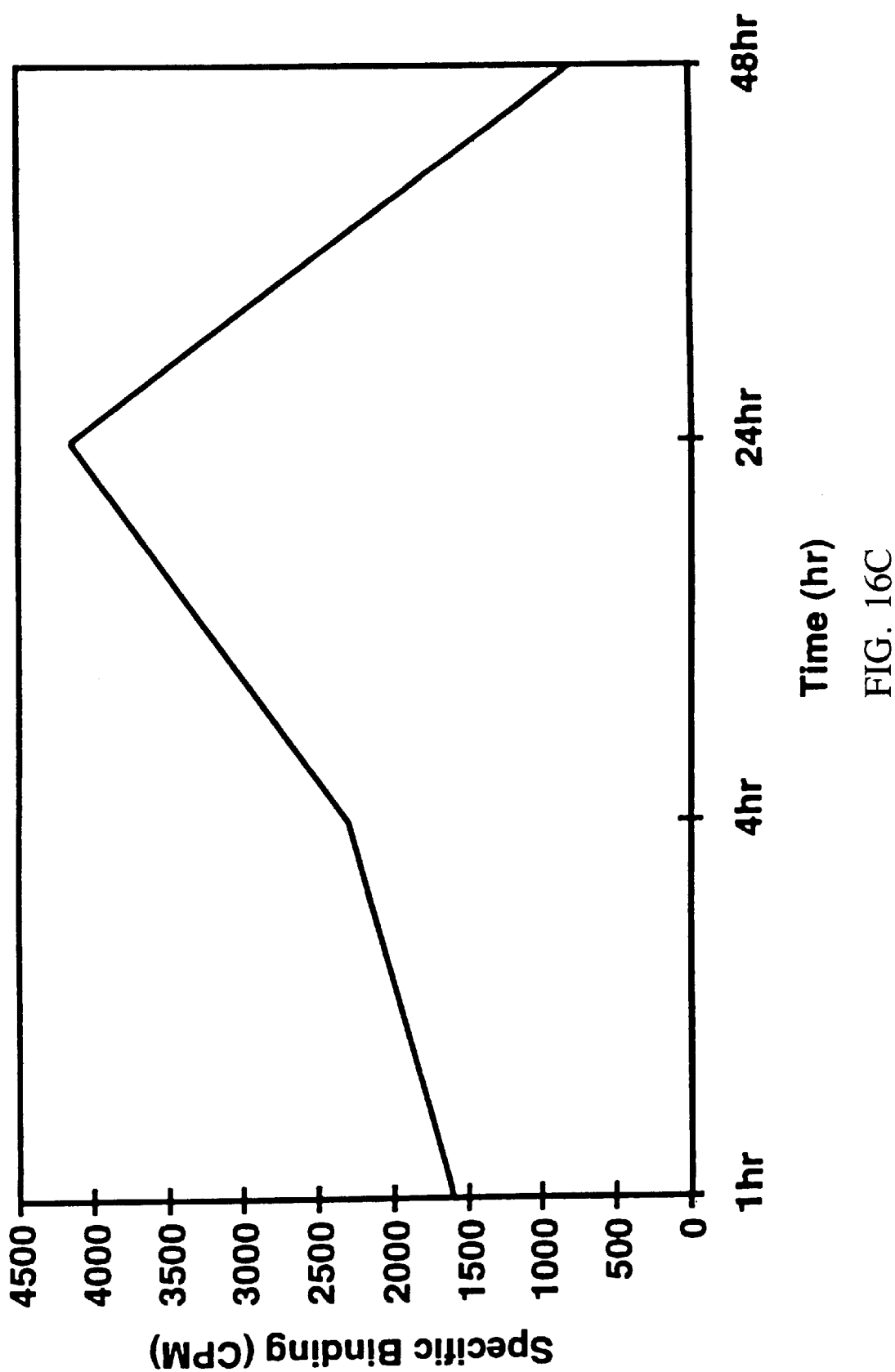
FIG. 16C illustrates the rate of binding of $^{125}$I-17-β-estradiol to the ZR-75-1 cell line.

The data demonstrate specific binding for all three cell lines at different densities. This binding and radioactivity was maintained for at least 24 hr. These data are similar to the uptake data for peptide hormones. The progressive accumulation of the radiolabeled steroid in the three cell lines is demonstrated in FIGS. 16A, 16B, and 16C. The rate of accumulation depends on the cell line. Thus infusion therapy would results in high rates of accumulation and retention of radiolabeled steroids.

EXAMPLE 10

Preliminary Results of a Pilot Clinical Trial of Monthly 180 mCi $^{111}$In-pentetreotide Infusions For six months, pilot clinical trials were conducted in ten human patients with progressive metastatic indolent and symptomatic neuroendocrine cancers expressing the somatostatin receptor. Ten patients were given from one to six doses of $^{111}$In-pentetreotide. The first monthly dose was a bolus injection of 180 mCi. The second monthly dose was infusion of 180 mCi over 72 hr. The third monthly dose was infusion of 180 mCi over 24 hr. Thereafter, all monthly doses were infusion of 180 mCi over 24 hr. Clinical benefits (as evidenced by reduced pain, weight gain, reduced malaise, etc.) occurred in 6 of the 10 neuroendocrine (carcinoid/islet cell) patients. Partial radiographic responses (greater than 50% reduction in the product of perpendicular tumor diameters) occurred in 2 patients, and significant tumor necrosis developed in 7 of the 10 neuroendocrine patients. Treatment-related toxicity included 2 Grade III platelet, 1 Grade II WBC, 1 Grade I WBC and 2 Grade I Hb on the NCI (National Cancer Institute) grading scale. This experiment demonstrated that $^{111}$In pentetreotide at 180 mCi monthly doses was an effective and well-tolerated antineoplastic agent in some subjects with somatostatin receptor-expressing neoplasms.

EXAMPLE 11

Overview of the trial design

Future clinical trials will begin with a nonrandomised trial to compare bolus to infusional administration of 180 mCi $^{111}$In-pentetreotide. Up to 30 participants will be recruited from approximately 100 patients with metastatic somatostatin receptor-expressing neuroendocrine cancers, as defined by a positive diagnostic 6 mCi $^{111}$In-pentetreotide (Octreoscan®) scan. The majority of these patients will have already received octreotide and still show signs of slow progression on the CT scan, biochemical markers and/or clinical symptoms (performance status, weight loss, increasing malaise, etc.).

Study population and eligibility

Subjects will have completed a "standard of care" therapy and still show signs of progressive disease. The majority of subjects with endocrine malignancies will have had at least one year of previous biotherapy with octreotide or interferon. Patients with non-endocrine malignancies will have had "standard of care" chemotherapy or radiation therapy. A subset of these patients will have received external beam radiotherapy to weight bearing bones and/or cytotoxic chemotherapy.

Following a dosimetric $^{111}$In-pentetreotide scan and CT scans, subjects who demonstrate pathologic uptake of the radioisotope in areas corresponding to sites of metastatic disease will be eligible for the trial. After the bolus and infusional doses, responding subjects will be eligible to continue receiving monthly treatments until the disease progression or regression warrants stopping this therapy.

Intervention $^{111}$In-pentetreotide will be given either as a rapid intravenous ("iv") bolus or as an iv infusion over 24 or 72 hr. Each subject will serve as his or her own control. An iv will be started and the radioactive dose administered either over several seconds, 24 hr, or 72 hr. Patients will receive iv hydration (100 cc/hr) with normal saline during therapy.

Some subjects will then enter the classical Phase I dose escalation portion of the trial. Three patients will be evaluated at the following doses of $^{111}$In-pentetreotide: 180, 360, 540, 720, 900, 1080, 1260 and 1440 mCi. It is anticipated that these doses will be administered as a continuous iv infusion over 24 hr.

Objectives

The first trial's major objective will be to determine the optimal rate of administration of 180 mCi doses of $^{111}$In-pentetreotide. Blood counts and blood chemistries will be analyzed prior to and weekly for 3 weeks after each treatment to identify any toxic effects. Nuclear scanning will occur daily for 3 days, and on days 7, 14, and 21 after the dose to determine uptake and excretion rates. Plasma samples will be collected and stored prior to therapy and monthly for 6 months for assay of tumor-related biomarkers. Additional plasma and urine samples will be collected daily to calculate clearance rates of the radioligand. Chest, abdominal, and pelvic CT scans (to determine radiographic response rate) will be performed prior to the first and third doses. Radioactive uptake ratios (tumor to background), therapeutic ratios (tumor to kidney), excretion rates, and radioactive dose (areas under the mRoentgen/hr vs time curve) will be calculated.

The second trial's major objective will be to determine the maximal tolerated amount of $^{111}$In-pentetreotide that can be given. The following doses of $^{111}$In-pentetreotide will be evaluated in groups of 3 patients: 180, 360, 540, 720, 900, 1080, 1260 and 1440 mCi. The same blood counts, chemistries, nuclear scanning and radiographic assessments as described above will be performed. Should at least two drug-related NCI Grade IV toxicities occur, treatment will be terminated at that level. The number of courses that can be administered will then be determined as dose limiting.

Patients will be examined prior to each treatment and monthly for 3 months following therapy. Their quality of life will be assessed by clinical benefits, including reduced pain, weight gain, or reduced malaise. Clinical responses will be determined as either present, no change, or absent. Biochemical responses will be assessed by the measurement of plasma chromogranin A and/or 24 hr urinary 5-HIAA or other elevated disease-related markers. A partial response is defined as a 50% or greater decrease in a tumor marker. Radiographic responses will be determined by comparing the product of the perpendicular tumor diameters using the following WHO criteria: (a) Complete response: the complete disappearance of disease; (b) Partial response: a 50% or greater decrease; (c) Stable response: less than a 50% decrease and less than a 20% increase; and (d) Progressive disease: greater than a 20% increase.

Data Analysis

The sample size for the phase I pilot study is determined by the objective of this study as stated above. In a preliminary trial, if the drug under investigation is 20% or more effective, one or more treatment successes should be seen in the first fourteen patients treated, with a confidence level of 95%. If a success is not seen in the first fourteen patients, the drug does not merit further investigational use. Thus, the sample size for this phase I study shall be fourteen evaluable patients. An additional 15 subjects will be studied after an interval analysis of the first 14 subjects. This latter group will assist in determining toxicity and efficacy. It is anticipated that indolent neuroendocrine neoplasms will dominate the first 15 slots since this population has shown the greatest potential of benefit.

To determine whether bolus or continuous $^{111}$In pentetreotide administration is optimal, areas under the 3 curves (mRoentgen/hr vs time) will be compared, and half-lives calculated. The optimal method of administration will be that method resulting in the largest area under the curve, with standard statistical tests to compare between and within subjects depending upon the distribution of the variance and whether parametric measures are indicated. The statistical software package NCSS or "Number Crunching Statistical Software" will be used.

EXAMPLE 12

Accumulation of Radiolabeled Somatostatin Analogs in Angiogenic Cells

To demonstrate that radiolabeled somatostatin analogs accumulate in angiogenic blood vessels, nude mice were implanted with SKNSH human neuroblastoma tumor cells lacking somatostatin receptors. The tumors were allowed to grow to about 1 cm in diameter, a period of approximately three to four weeks. The mice were then injected with 50 $\mu$Ci of $^{125}$I-WOC-4a. The radioligand was allowed to clear for 1 week. On Day 7 the mice were scanned on a photosensitive plate and a standard x-ray plate. The resulting photographs were superimposed in register to allow localization of the radioligand. The radioligand was localized in the tumor. Because the tumor cells did not have receptors for somatostatin analogs and could not bind the radioligand, it was concluded that the radioligand seen in the tumor area was bound by angiogenic blood vessels.

Human placental-derived vascular endothelial cells were used to assay for cell binding of the somatostatin analog, $^{125}$I-JIC-2D. The radioligand, a somatostatin analog, $^{125}$I-JIC-2D, was made by solid phase peptide synthesis as described in U.S. Pat. No. 5,597,894. This peptide has an amino acid sequence of the following: D-Lys-D-Tyr-D-Lys-D-Tyr-D-Lys-c[Cys-Phe-D-Trp-Lys-Thr-Cys]-Thr-NH$_2$. The cells were obtained by growing discs of human placental veins in fibrinclots for 14 days. In this method, a fraction of discs exhibit an angiogenic response. These discs and their angiogenic sprouts are harvested mechanically and dissociated by vortexing. The vein discs are then discarded and the endothelial cells pooled. Cells were harvested, counted with a hemocytometer, and resuspended in binding buffer (Minimum Essential Medium (MEM), 10 mM Hepes, 0.01% BSA). A standard assay used 500,000 cells in 1 ml of binding buffer. Radioactive ligand alone (500,000 cpm), or in combination with at least 1,000-fold molar excess ($10^{-6}$ M) non-radioactive compound (to calculate specific binding), was added to a final volume of 1 ml. At the termination of the experiment, the incubation medium was removed, the cells were rinsed twice with Hanks balanced salt solution (HBSS), and the radioactivity in the cells determined using a gamma counter. This level of radioactivity represents total binding, which includes both membrane-bound and internalized fractions. Specific binding was determined by calculating the difference in the levels of measured radioactivity without the unlabeled competitor minus the radioactivity with the unlabeled competitor.

To differentiate between membrane and intracellular binding, cells were subsequently incubated for 10 min at 4° C. with acidified HBSS (pH=4–5), rinsed in HBSS, and the radioactivity again determined using the gamma counter. Since the acid wash preferentially released the radioactive ligand from the external surface of the cell, remaining radioactivity was attributed to internalized fractions.

Figure 17:
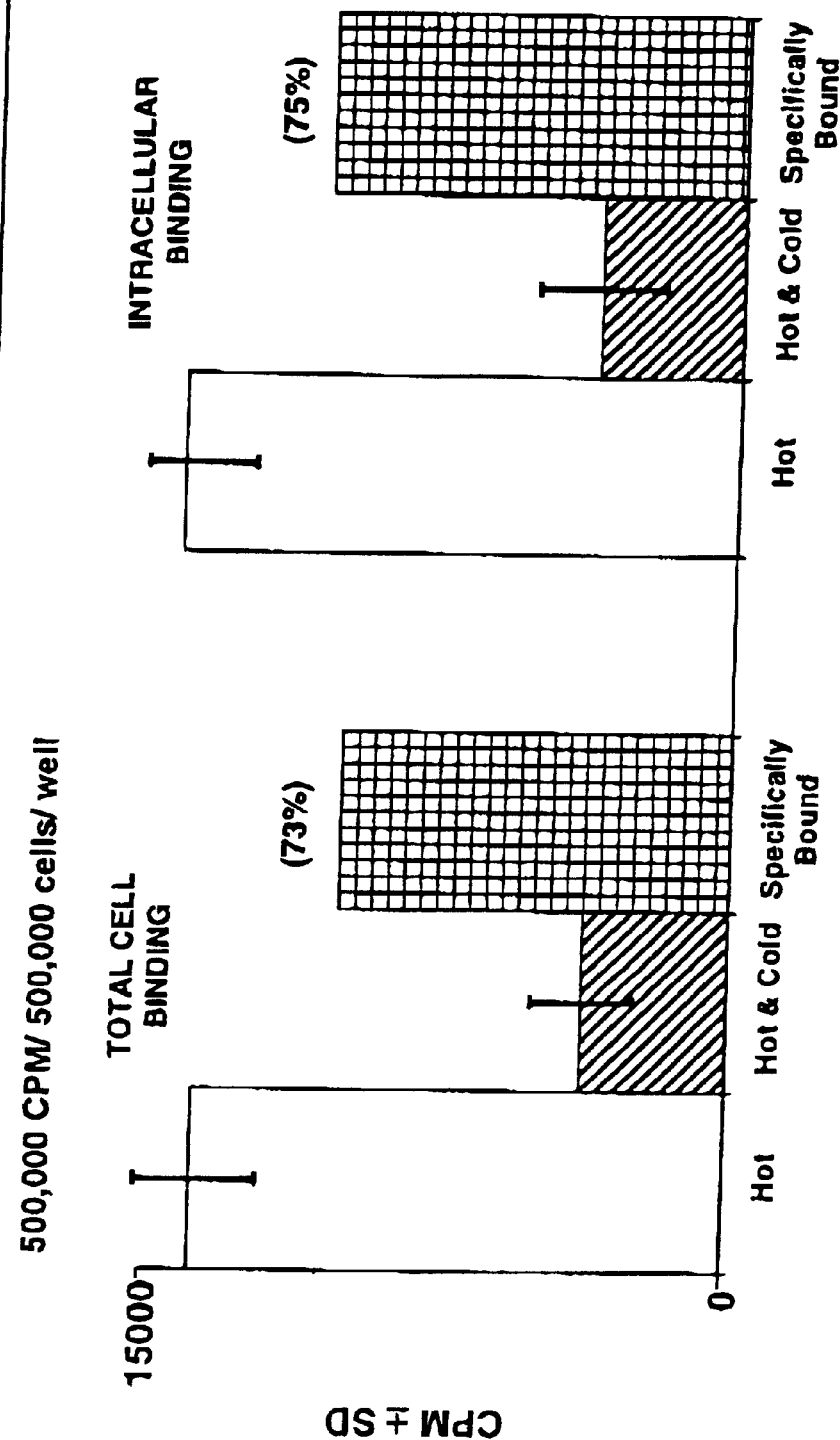
FIG. 17 illustrates the binding and internalization of $^{125}$I-JIC-2D in human angiogenic vascular endothelial cells.

As shown in FIG. 17, the radiolabeled somatostatin analog bound to the angiogenic cells and the vast majority of the radioligand was internalized into the cell.

EXAMPLE 13

Radiolabeled Somatostatin Analog Inhibition of Angiogenic Cell Growth

To demonstrate that radiolabeled somatostatin analogs inhibit angiogenic blood vessel growth, the Human Placental Vein Angiogenesis Model was used as described in J. C. Watson et al., "Up-Regulation of Somatostatin Receptor Subtype 2 (SST-2) mRNA Occurs During the Transformation of Human Endothelium to the Angiogenic Phenotype," Paper Presented at the 12th International Symposium on Regulatory Peptides, Copenhagen, Denmark, September 1996; J. C. Watson et al., "SST-2 Gene Expression Appears During Human Angiogenesis," Regulatory Peptides, vol. 64, p. 206 (Abstract) (1996); and J. C. Watson et al., "Breast Cancer Increases Initiation of Angiogenesis Without Accelerating Neovessel Growth Rate," Surgery, vol. 122, pp. 508–14 (1997). Human placental veins were cut into discs of 2 mm diameter and were incorporated into a 0.3% fibrinogen gel. This gel was then overlaid with tissue culture media containing 10–20% fetal calf serum (FCS). Under normal conditions, endothelial cords will begin to sprout from the transected cut edge of the vein discs within six days.

Figure 18:
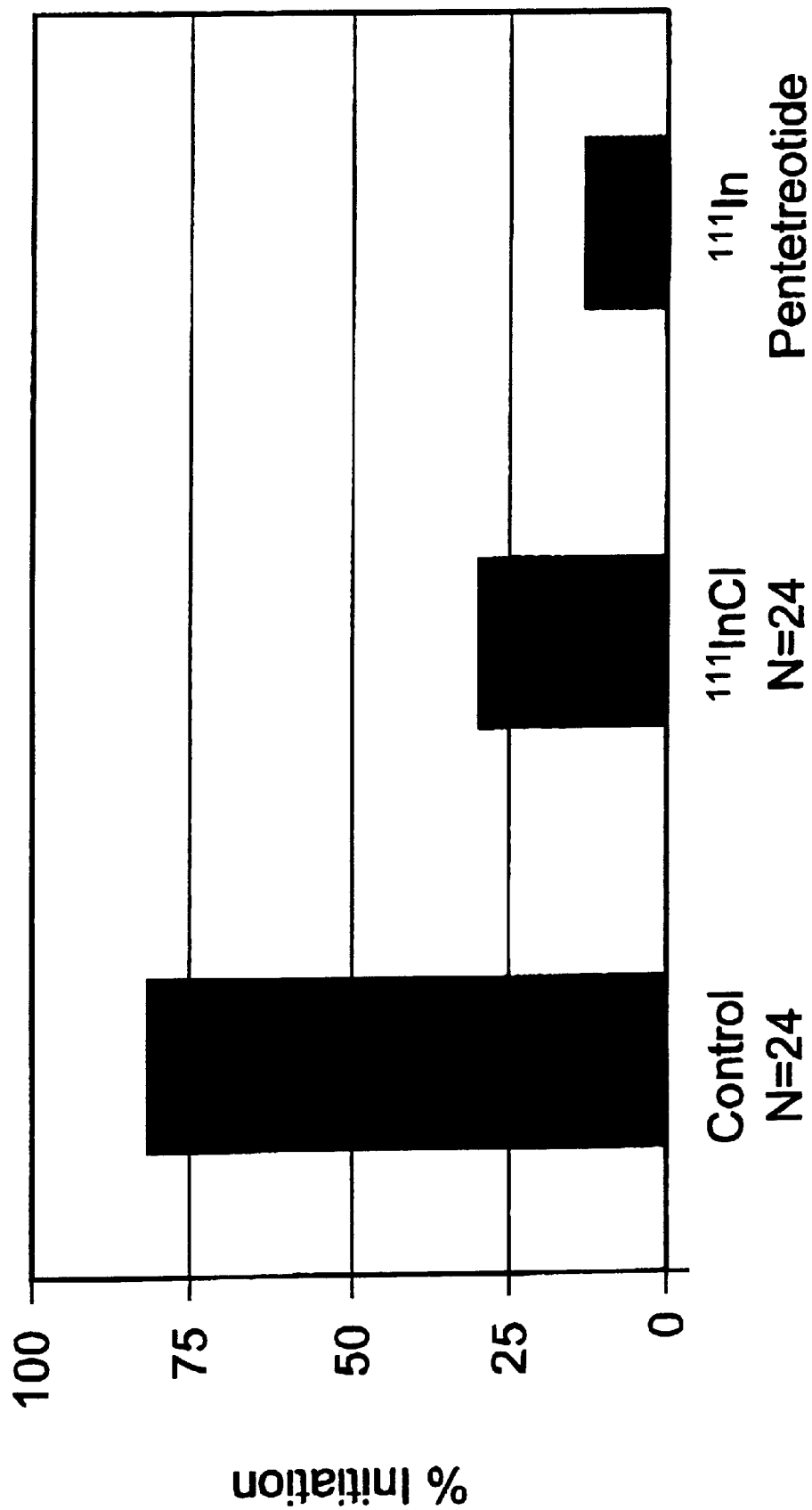
FIG. 18 illustrates the effect of an Auger emitter, $^{111}$In-pentetreotide, on initiation of human angiogenic vascular tissue.

These vein discs were placed into wells of three separate culture plates. One culture plate, the control sample, was allowed to grow without treatment. Another plate was treated with 50 $\mu$Ci/mL of the radiolabeled somatostatin analog, $^{111}$In-pentetreotide; and the third plate treated with equivalent amounts of $^{111}$In-Cl. The discs were then incubated for fourteen days. After 14 days the culture plates were examined for the number of wells in which angiogenic growth was initiated. The percentage initiation is shown in FIG. 18. The % initiation seen in both treated culture plates was substantially less than the control plate. The lowest % initiation was seen in the culture plate treated with $^{111}$In-pentetreotide. The molar concentration of the radiolabeled somatostatin analog added to the culture plates was in the femtomolar range ($10^{-15}$). This concentration is 1000× or more below the concentration of unlabeled somatostatin analog that is known to inhibit angiogenesis; a concentration of $10^{-5}$ M to $10^{-8}$ M. Thus any effect was due to the radiolabel and not just the presence of the somatostatin analog. Any difference between the $^{111}$In-Cl and $^{111}$In-pentetreotide is due to an effect of Auger emission on angiogenic cell growth through Auger effect on the DNA. Only the radiolabel connected to the somatostatin analog would be incorporated into the DNA. Thus the greater decrease is due to this incorporation and the Auger emission on DNA.

Figure 19:
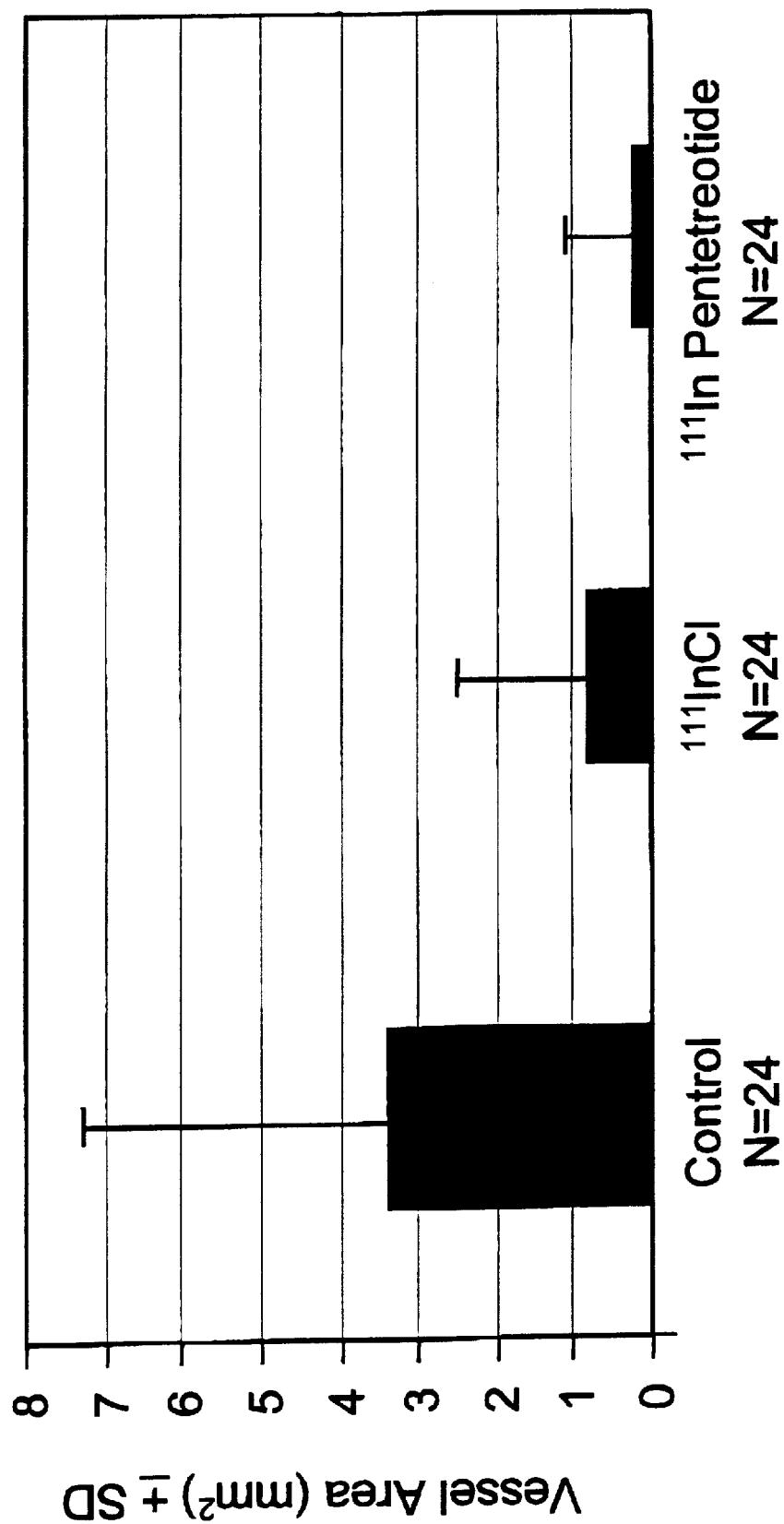
FIG. 19 illustrates the effect of an Auger emitter, $^{111}$In-pentetreotide, on vessel area of human angiogenic vascular tissue.

Using a digital image analyzer, the mean area of the sprouting tissue surrounding the discs was measured. As shown in FIG. 19, the vessel area (mm$^2$) was also substantially less in both treated culture plates. Again, the plate treated with the $^{111}$In-pentetreotide showed the least area of new growth.

Figure 20:
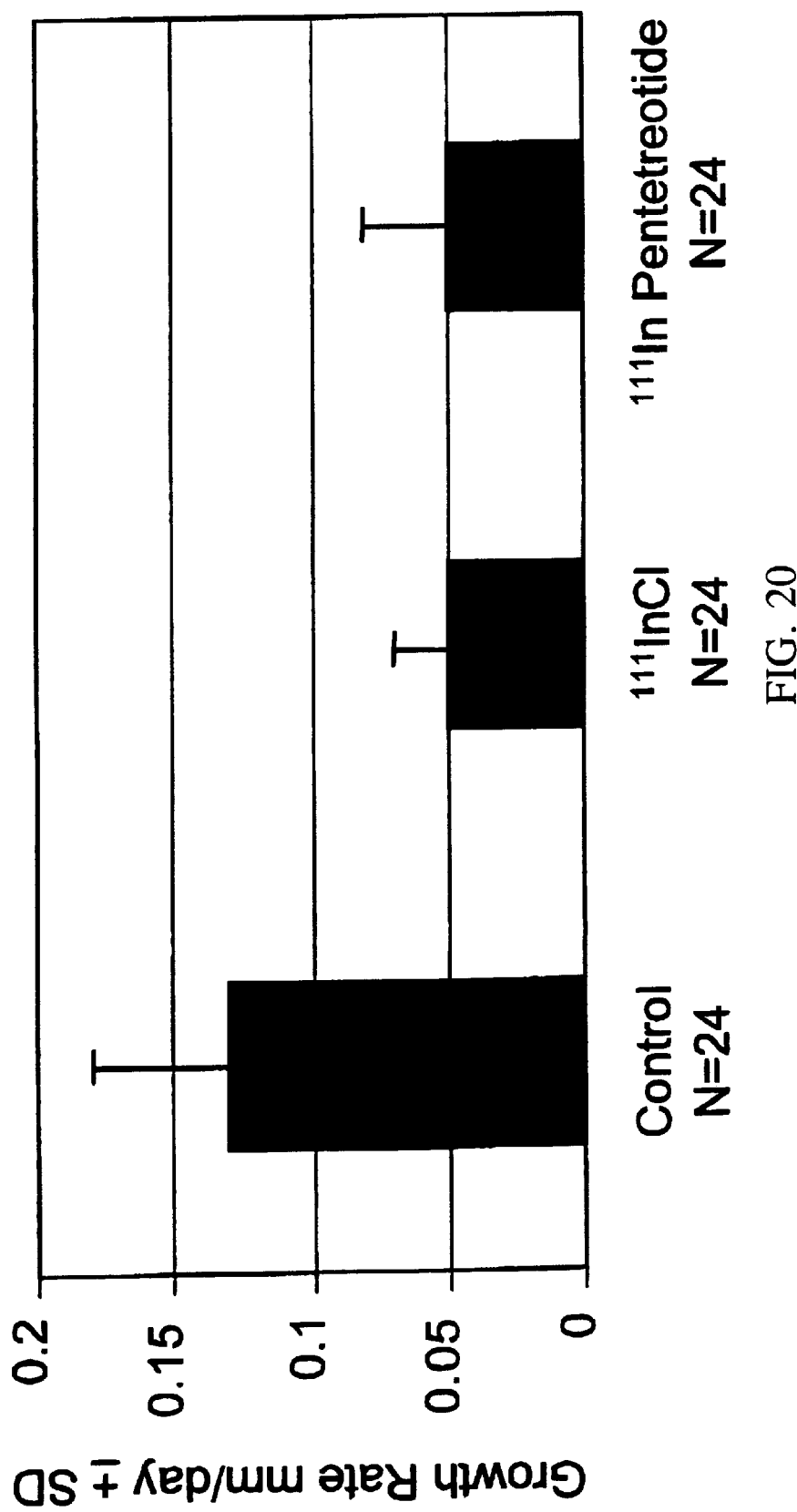
FIG. 20 illustrates the effect of an Auger emitter, $^{111}$In-pentetreotide, on growth rate of human angiogenic vascular tissue.

To measure the growth rate of angiogenic vascular tissue, every two days during the 14-day incubation period, the length of sprouts were measured. The growth rate as measured by mm/day for all three culture plates is given in FIG. 20. Again, the growth rate in the two treated culture plates is substantially below that of the control. However, there is no difference in the growth rate between the two treated samples.

Thus, the radiolabeled somatostatin analog inhibited angiogenic vascular growth even at concentrations far lower than that required for the unlabeled analog to inhibit angiogenic growth. This indicates that the gamma emission causes some inhibition and the Auger emission by the radiolabeled analog caused additional inhibition. The most effective inhibition was the radiolabeled analog, which included both effect of gamma and Auger emission.

Other somatostatin analogs will be tested using the same human placental vascular discs. These discs will be placed into wells of two separate culture plates. One culture plate will be allowed to grow to maturity without treatment. The other culture plate will be exposed to various treatments: (1) radiolabeled somatostatin analog ($^{125}$I-WOC-4a, $^{131}$I-WOC-4a, $^{111}$In-DPTA-WOC-4a, $^{111}$In-DPTA-JIC-2D, $^{125}$I-JIC-2D, or dual labelled $^{111}$In-DPTA-$^{125}$I-WOC-4a or $^{111}$In-DPTA-$^{125}$I-JIC-2D,); (2) cold, unlabeled somatostatin analog (WOC-4a or JIC-2D); (3) radioisotope alone ($^{125}$I or $^{131}$I); (4) a combination of the radiolabeled somatostatin analog and its corresponding unlabeled analog (e.g., $^{125}$I-WOC-4a and WOC-4a); or (5) a combination of the cold, unlabeled somatostatin analog and the unbound radioisotope (e.g., $^{125}$I and WOC-4a). The discs will be incubated for three days with the analog present in a dose ranging from 10 to 1,000,000 counts per well. After three days fresh media will be added and the discs observed until maturity. The percentage of wells that initiate an angiogenic response will be calculated for non-treated and treated wells. The results from the different treatments will be analyzed with ANOVA.

Alternatively, to amplify the degree of cell destruction caused by the radioactivity, the vein discs will be cryoprotected and kept frozen in liquid nitrogen after a three day exposure to the radioligand. Freezing will inhibit cell division but will not affect radioactivity. Another set of plates will be constructed with identically treated vein discs but no radiation source. At the end of three days of treatment, these vein discs will be harvested, washed, and cryopreserved in tissue culture media containing 10% dimethylsulfoxide (DMSO). These vein discs will be cryopreserved in a controlled-rate freezer and stored in liquid nitrogen for 2 months, or for a period that is six times the physical half-life of the radioisotope used. At this time, the vein discs will be thawed and re-planted in fibrinogen gel-containing wells and allowed to grow as described above. After two weeks of growth, the treated and non-treated wells will be compared.

These experiments demonstrate that radiolabeled somatostatin analogs will selectively inhibit initiation or promotion of the human angiogenic response in a manner similar to inhibition of tumor cell growth in tumor cells with somatostatin receptors. Thus, for use of radiolabeled somatostatin analogs in either radioimaging or radiotherapy for angiogenic blood vessels, administration by infusion will be more effective than a bolus injection.

EXAMPLE 14

Upregulation of PDGF Receptors in Human Angiogenic Cells

Using the in vitro human placental vein angiogenesis model described above, we substituted discs taken from human vascular endothelium from aorta and inferior vena cava to assay for presence of platelet-derived growth factor (PDGF) and its receptor. A similar angiogenic response was seen in fourteen days of incubating the 2 mm discs in a 0.3% fibrin clot, supplemented with fetal bovine serum. RNA was extracted from inferior vena cava and aorta that was obtained from organ donors and from the tissue-matched angiogenic explants cultured as above. Reverse transcription polymerase chain reactions (RT-PCR) were then conducted on each sample with primers specific for the PDGF A chain, B chain and the receptor using 500 ng of RNA per reaction. Primers were made according to published sequence data. RT-PCR products were analyzed by gel electrophoresis which revealed bands in the expected positions for these products in the angiogenic explants of both the aorta and inferior vena cava, but not in their native vessel counterparts. These results were repeated in blood vessel samples from three patients with identical results. This suggests both the PDGF A chain and B chain may play an important role in the regulation of the angiogenic response. This indicates that radiotherapy directed toward this growth factor or its receptor may be effective in limiting development of angiogenesis associated with tumor growth.

A person of ordinary skill in the art will recognize that by techniques similar to those described in the above examples, the efficacy of bolus versus infusion administration of other radiolabeled peptides and steroids for radiotherapy and radioimaging of tumors may be determined.

The complete disclosures of all references cited in this specification are hereby incorporated by reference. Also incorporated by reference is the complete disclosure of the following abstract which is not prior art: M. O. Meyers et al., "Gene Upregulation of PDGF in Human Angiogenesis," Paper Presented at the Association for Academic Surgery, Seattle, Wash., Nov. 19–22, 1998. In the event of an otherwise irreconcilable conflict, however, the present specification shall control.

We claim:

1. A method for selectively accumulating a receptor-dependent radiolabeled compound inside target cells in a patient, wherein the target cells are selected from the group consisting of tumor cells and angiogenic cells, wherein the target cells express receptors for the radiolabeled compound, comprising administering a dose of the radiolabeled compound to the patient by infusion during a period greater than two hours, wherein the resulting residence time of the radiolabeled compound in the target cells is at least one and one-half (1.5) times the residence time of the radiolabeled compound in the target cells that would result from a bolus administration of the same total dose of the same radiolabeled compound to the patient.

2. The method of claim 1, wherein the rate of infusion is approximately equal to the rate of cellular uptake and translocation to the nucleus of the radiolabeled compound by the tumor cells.

3. The method of claim 1, wherein the period of infusion is between about 4 hours and about 30 days.

4. The method of claim 1, wherein the period of infusion is between about 24 hours and about 5 days.

5. The method of claim 1, wherein said target cells are tumor cells.

6. The method of claim 1, wherein said target cells are angiogenic cells.

7. The method of claim 1, wherein said radiolabeled compound comprises a receptor-dependent peptide bound to a radioisotope.

8. The method of claim 7, wherein said receptor-dependent peptide is selected from the group consisting of nerve growth factor, fibroblast growth factor, epidermal growth factor, platelet-derived growth factor, vascular endothelial growth factor, cholecystokinin, vasoactive intestinal peptide, gastrin-releasing peptide, leukemia inhibitory factor, somatostatin, oxytocin, bombesin, calcitonin, arginine vasopressin, angiotensin II, atrial natriuretic peptide, insulin, glucagon, prolactin, growth hormone, gonadotropin, thyrotropin-releasing hormone, growth hormone-releasing hormone, gonadotropin-releasing hormone, corticotropin-releasing hormone, interleukins, interferons, transferrin, substance P, neuromedin, neurotensin, neuropeptide Y, and opioids.

9. The method of claim 7, wherein said receptor-dependent peptide is somatostatin.

10. The method of claim 7, wherein said receptor-dependent peptide is vascular endothelial growth factor and said target cells are angiogenic cells.

11. The method of claim 7, wherein said receptor-dependent peptide is platelet-derived growth factor and said target cells are angiogenic cells.

12. The method of claim 7, wherein said receptor-dependent peptide is a somatostatin analog.

13. The method of claim 12, wherein said somatostatin analog is selected from the group consisting of octreotide, pentetreotide, vapreotide, lanreotide, WOC-3b, WOC-4a, and JIC-2D.

14. The method of claim 12, wherein said somatostatin analog is pentetreotide.

15. The method of claim 12, wherein said somatostatin analog is WOC-4a.

16. The method of claim 12, wherein said somatostatin analog is WOC-3b.

17. The method of claim 12, wherein said somatostatin analog is JIC-2D.

18. The method of claim 7, wherein said radioisotope has a half-life between about 1 hour and about 60 days.

19. The method of claim 7, wherein said radioisotope has a half-life between about 2 hours and about 60 days.

20. The method of claim 7, wherein said radioisotope has a half-life between about 12 hours and about 60 days.

21. The method of claim 7, wherein said radioisotope is selected from the group consisting of $^{67}$Ga, $^{111}$In, $^{99m}$Tc, $^{90}$Y, $^{86}$Y, $^{169}$Yb, $^{188}$Re, $^{125}$I, $^{123}$I, $^{124}$I, $^{129}$I, $^{131}$I, and $^{77}$Br.

22. The method of claim 7, wherein said radioisotope is $^{111}$In.

23. The method of claim 7, wherein said radioisotope is $^{125}$I.

24. The method of claim 7, wherein said radioisotope is $^{131}$I.

25. The method of claim 1, wherein said radiolabeled compound is selected from the group consisting of $^{111}$In-pentetreotide ($^{111}$In-DTPA-D-Phe$^1$-octreotide), ($^{111}$In-DOTA$^0$-D-Phe$^1$-Tyr$^3$)-octreotide, ($^{90}$Y-DOTA$^0$-D-Phe$^1$-Tyr$^3$)-octreotide, ($^{86}$Y-DOTA$^0$-D-Phe$^1$-Tyr$^3$)-octreotide, $^{111}$In-DTPA-D-Phe$^1$-RC-160, $^{99m}$Tc-RC-160, $^{99m}$Tc-CPTA-RC-160, $^{123}$I-RC-160, $^{125}$-RC-160, $^{131}$I-RC-160, $^{99m}$Tc-octreotide, $^{188}$Re-RC-160, $^{123}$I-tyr$^3$-octreotide, $^{125}$I-tyr$^3$-octreotide, $^{131}$I-tyr$^3$-octreotide, $^{125}$I-lanreotide, $^{123}$I-lanreotide, $^{131}$I-lanreotide, $^{90}$Y-DOTA-lanreotide, $^{86}$Y-DOTA-lanreotide, $^{111}$In-DPTA-lanreotide, $^{111}$In-DOTA-lanreotide, $^{111}$In-DPTA-somatostatin, $^{90}$Y-DOTA-somatostatin, $^{86}$Y-DOTA-somatostatin, $^{125}$I-somatostatin, $^{131}$I-WOC-3b, $^{125}$I-WOC-3b, $^{131}$I-WOC-4a, $^{125}$I-WOC-4a, $^{125}$I-JIC-2D, $^{123}$I-JIC-2D, and $^{131}$I-JIC-2D.

26. The method of claim 25, wherein said radiolabeled compound is accumulated in cells of tumors selected from the group consisting of endocrine tumors, melanomas, breast carcinomas, Merkel cell tumors, lymphomas, small cell lung carcinomas, gastrointestinal tumors, astrocytomas, gliomas, meningiomas, carcinoid tumors, islet cell tumors, renal cell carcinomas, neuroblastomas, and pheochromocytomas.

27. The method of claim 25, wherein said radiolabeled compound is accumulated in angiogenic cells.

28. The method of claim 1, wherein said radiolabeled compound is $^{111}$In-pentetreotide.

29. The method of claim 28, wherein said radiolabeled compound is accumulated in tumor cells selected from the group consisting of pituitary tumors, endocrine pancreatic tumors, carcinoids, paragangliomas, pheochromocytomas, medullary thyroid carcinomas, small cell lung carcinomas, neuroblastomas, meningiomas, lymphomas, glucagonomas, breast carcinomas, renal cell carcinomas, gliomas, astrocytomas, and melanomas.

30. The method of claim 28, wherein said radiolabeled compound is accumulated in angiogenic cells.

31. The method of claim 28, wherein said radiolabeled compound is accumulated in neuroblastoma cells.

32. The method of claim 28, wherein said radiolabeled compound is accumulated in small cell-lung carcinoma cells.

33. The method of claim 28, wherein said radiolabeled compound is accumulated in endocrine tumor cells.

34. The method of claim 1, wherein said radiolabeled compound is $^{125}$I-WOC-4a.

35. The method of claim 34, wherein said radiolabeled compound is accumulated in neuroblastoma cells.

36. The method of claim 34, wherein said radiolabeled compound is accumulated in angiogenic cells.

37. The method of claim 1, wherein said radiolabeled compound is $^{131}$I-WOC-4a.

38. The method of claim 37, wherein said radiolabeled compound is accumulated in neuroblastoma cells.

39. The method of claim 37, wherein said radiolabeled compound is accumulated in angiogenic cells.

40. The method of claim 1, wherein said radiolabeled compound is $^{125}$I-WOC-3b.

41. The method of claim 40, wherein said radiolabeled compound is accumulated in neuroblastoma cells.

42. The method of claim 40, wherein said radiolabeled compound is accumulated in angiogenic cells.

43. The method of claim 1, wherein said radiolabeled compound is $^{125}$I-somatostatin.

44. The method of claim 1, wherein said radiolabeled compound is $^{125}$I-JIC-2D.

45. The method of claim 44, wherein said radiolabeled compound is accumulated in angiogenic cells.

46. The method of claim 5, wherein said radiolabeled compound comprises a receptor-dependent steroid bound to a radioisotope.

47. The method of claim 46, wherein said receptor-dependent steroid is selected from the group comprising estrogen, testosterone, progesterone, glucocorticosteriods, and mineralocorticoids.

48. The method of claim 46, wherein said receptor-dependent steroid is estradiol.

49. The method of claim 46, wherein said radioisotope has a half-life between about 1 hour and about 60 days.

50. The method of claim 46, wherein said radioisotope has a half-life between about 5 hours and about 60 days.

51. The method of claim 46, wherein said radioisotope has a half-life between about 12 hours and about 60 days.

52. The method of claim 46, wherein said radioisotope is selected from the group consisting of $^{67}$Ga, $^{111}$In, $^{99m}$Tc, $^{90}$Y, $^{86}$Y, $^{169}$Yb, $^{188}$Re, $^{125}$I, $^{123}$I, $^{124}$I, $^{129}$I, $^{131}$I, and $^{77}$Br.

53. The method of claim 46, wherein said radioisotope is $^{125}$I.

54. The method of claim 5, wherein said radiolabeled compound is $^{125}$I-17-β-estradiol.

55. The method of claim 54, wherein said radiolabeled compound is accumulated in breast cancer cells.

56. The method of claim 1, further comprising the step of imaging radioactivity in the area of said target cells by scintigraphy.

57. The method of claim 1, further comprising the step of repeating the process of claim 1 until there is at least a 50% decrease in a tumor marker as measured by biochemical and radiographical techniques.

* * * * *